United States Patent
Wagner, Jr. et al.

(10) Patent No.: US 12,428,465 B2
(45) Date of Patent: *Sep. 30, 2025

(54) THERAPEUTIC PEPTIDES AND METHODS FOR TREATING TYPE 2 DIABETES

(71) Applicant: OP-T LLC, Denver, CO (US)

(72) Inventors: David H. Wagner, Jr., Denver, CO (US); Martin G. Yussman, Denver, CO (US); Charles W. Henry, Denver, CO (US)

(73) Assignee: OP-T LLC, Aurora, CO (US)

( * ) Notice: Subject to any disclaimer, the term of this patent is extended or adjusted under 35 U.S.C. 154(b) by 73 days.

This patent is subject to a terminal disclaimer.

(21) Appl. No.: 17/365,881

(22) Filed: Jul. 1, 2021

(65) Prior Publication Data

US 2021/0332104 A1  Oct. 28, 2021

Related U.S. Application Data

(63) Continuation of application No. 16/240,630, filed on Jan. 4, 2019, now abandoned, which is a continuation-in-part of application No. 16/184,129, filed on Nov. 8, 2018, now abandoned.

(60) Provisional application No. 62/669,918, filed on May 10, 2018.

(51) Int. Cl.
| | | |
|---|---|---|
| C07K 14/705 | (2006.01) | |
| A61K 38/08 | (2019.01) | |
| A61K 38/17 | (2006.01) | |
| A61K 38/19 | (2006.01) | |
| A61K 40/42 | (2025.01) | |
| A61K 38/10 | (2006.01) | |

(52) U.S. Cl.
CPC ...... *C07K 14/70575* (2013.01); *A61K 38/191* (2013.01); *A61K 38/08* (2013.01); *A61K 38/10* (2013.01); *A61K 38/1774* (2013.01); *A61K 40/4215* (2025.01)

(58) Field of Classification Search
None
See application file for complete search history.

(56) References Cited

U.S. PATENT DOCUMENTS

| | | |
|---|---|---|
| 4,642,295 A | 2/1987 | Baker |
| 6,264,951 B1 | 7/2001 | Armitage |
| 6,319,671 B1 | 11/2001 | U'ren et al. |
| 6,812,203 B1 | 11/2004 | Pype et al. |
| 7,087,573 B1 | 8/2006 | Lazarus |
| 7,098,322 B2 | 8/2006 | Pype et al. |
| 7,189,518 B2 | 3/2007 | Schonbeck et al. |
| 7,601,335 B2 | 10/2009 | McCutcheon et al. |
| 7,741,280 B2 | 6/2010 | Guichard et al. |
| 8,476,008 B2 | 7/2013 | Nagalla et al. |
| 9,409,987 B2 | 8/2016 | Toporik et al. |
| 9,562,088 B2 * | 2/2017 | Wagner ............ C07K 14/70575 |
| 10,882,911 B2 | 1/2021 | Park et al. |
| 11,130,795 B2 | 9/2021 | Wagner |
| 11,744,875 B2 * | 9/2023 | Wagner, Jr. ............ A61K 38/10 |
| | | 514/6.9 |
| 11,793,854 B2 | 10/2023 | Wagner, Jr. et al. |
| 12,048,734 B2 | 7/2024 | Wagner, Jr. et al. |
| 2003/0078269 A1 | 4/2003 | Pearson et al. |
| 2004/0072750 A1 | 4/2004 | Phillips et al. |
| 2005/0101769 A1 | 5/2005 | Pype et al. |
| 2005/0202531 A1 | 9/2005 | Toporik |
| 2006/0234316 A1 | 10/2006 | Wagner |
| 2007/0041971 A1 | 2/2007 | Wagner |
| 2007/0243259 A1 | 10/2007 | Sung et al. |
| 2008/0050369 A1 | 2/2008 | Yellin et al. |
| 2008/0058360 A1 | 3/2008 | Schonbeck et al. |
| 2010/0062471 A1 | 3/2010 | Kantor et al. |
| 2010/0172869 A1 | 7/2010 | Masuoka |
| 2011/0177556 A1 | 7/2011 | Prussak et al. |
| 2011/0178000 A1 | 7/2011 | Freyberg et al. |
| 2011/0229495 A1 | 9/2011 | Wagner |
| 2012/0282291 A1 | 11/2012 | Berghman et al. |
| 2013/0203719 A1 | 8/2013 | Kalergis et al. |
| 2013/0209463 A1 | 8/2013 | Rotman et al. |
| 2013/0236495 A1 | 9/2013 | Wagner |

(Continued)

FOREIGN PATENT DOCUMENTS

| | | |
|---|---|---|
| WO | WO-1999/011263 A1 | 3/1999 |
| WO | WO-2005/006949 A2 | 1/2005 |

(Continued)

OTHER PUBLICATIONS

Nathan, Diabetes Advances in Diagnosis and Treatment. JAMA, 2015; 314(10):1052-1062. (Year: 2015).*
Mach et al. "Reduction of atherosclerosis in mice by inhibition of CD40 signalling", Nature, vol. 3694, pp. 200-203, Jul. 9, 1998.
Shi et al., "Ldlr-Deficient Mice with and Atherosclerosis-Resistant Background Develop Severe Hyperglycemia and Type 2 Diabetes on a Western-Type Diet," Biomedicines 10(6): 12 pages (2022).
"Society commits $19.4 Million for New MS Research Projects," National Multiple Sclerosis Society, 2013 retrieved from http://vitaminad.nositio.net/news/New_Research_Fall_2013.pdf, 28 pages.
Aarts et al., "Inhibition of CD4-TRAF6 interactions by the small molecule Inhibitor 6877002 reduces neuroinflammation," Journal of Neuroinflammation, 14(105): 105-118 (2017).

(Continued)

*Primary Examiner* — Daniel E Kolker
*Assistant Examiner* — Maureen Varina Driscoll
(74) *Attorney, Agent, or Firm* — Foley Hoag LLP; Brendan T. Jones; David E. Shore

(57) ABSTRACT

The present disclosure provides, among other things, small peptides that are capable of interacting with CD40, thereby interfering with the ability of CD40 to interact with CD154, which impacts, e.g., inflammation and atherosclerosis. The present disclosure further provides use of such peptides in the treatment of, e.g., type 2 diabetes and auto-inflammatory disease. In particular, small peptides that are capable of interacting with CD40, thereby interfering with the ability of CD40 to interact with CD154, impact inflammation and type 2 diabetes.

20 Claims, 25 Drawing Sheets

Specification includes a Sequence Listing.

(56) References Cited

U.S. PATENT DOCUMENTS

| | | |
|---|---|---|
| 2013/0306034 A1 | 11/2013 | Hamedovic et al. |
| 2014/0044641 A1 | 2/2014 | Toporik et al. |
| 2014/0135684 A1 | 5/2014 | Kuo et al. |
| 2014/0170141 A1 | 6/2014 | Toporik et al. |
| 2015/0366946 A1 | 12/2015 | Vol et al. |
| 2016/0200823 A1 | 7/2016 | Burkly et al. |
| 2016/0296609 A1 | 10/2016 | Oh et al. |
| 2016/0347816 A1 | 12/2016 | Toporik et al. |
| 2016/0356771 A1 | 12/2016 | Smith et al. |
| 2017/0108514 A1 | 4/2017 | Wagner |
| 2017/0232062 A1 | 8/2017 | Rotman et al. |
| 2017/0306034 A1 | 10/2017 | Honczarenko et al. |
| 2017/0319671 A1 | 11/2017 | Faulkner et al. |
| 2017/0355747 A1 | 12/2017 | Wagner |
| 2018/0194829 A1 | 7/2018 | Toporik et al. |
| 2018/0194847 A1 | 7/2018 | Park et al. |
| 2019/0194290 A1 | 6/2019 | Wagner, Jr. et al. |
| 2019/0231848 A1 | 8/2019 | Rotman et al. |
| 2019/0263888 A1 | 8/2019 | Wagner, Jr. et al. |
| 2020/0072837 A1 | 3/2020 | Wagner, Jr. et al. |
| 2020/0297795 A1 | 9/2020 | Wagner, Jr. et al. |
| 2020/0326333 A1 | 10/2020 | Wagner, Jr. et al. |
| 2021/0008162 A1 | 1/2021 | Wagner, Jr. et al. |
| 2021/0332104 A1 | 10/2021 | Wagner, Jr. et al. |
| 2022/0000979 A1 | 1/2022 | Wagner, Jr. et al. |
| 2022/0106381 A1 | 4/2022 | Wagner |
| 2023/0101772 A1 | 3/2023 | Wagner, Jr. et al. |
| 2024/0115651 A1 | 4/2024 | Wagner, Jr. et al. |

FOREIGN PATENT DOCUMENTS

| | | |
|---|---|---|
| WO | WO-2007/090280 A1 | 8/2007 |
| WO | WO-2008/036675 A2 | 3/2008 |
| WO | WO-2010/055510 A2 | 5/2010 |
| WO | WO-2012/054584 A2 | 4/2012 |
| WO | WO-2012/154215 A1 | 11/2012 |
| WO | WO-2015/148389 A2 | 10/2015 |
| WO | WO-2019/032945 A1 | 2/2019 |
| WO | WO-2019/094581 A1 | 5/2019 |
| WO | WO-2019/136307 A1 | 7/2019 |
| WO | WO-2020/210726 A1 | 10/2020 |
| WO | WO-2021/011437 A1 | 1/2021 |
| WO | WO-2021/212013 A2 | 10/2021 |
| WO | WO-2021/231898 A2 | 11/2021 |

OTHER PUBLICATIONS

Aarts et al., "The CD40-CD40L dyad in Experimental Autoimmune Encephalomyelitis and Multiple Sclerosis," Chapter 2 Front. Immunol., 8(1791): 24-45 (2017).

Abdelhak et al., "Primary Progressive Multiple Sclerosis: Putting Together the Puzzle," Frontiers in Neurology, 8:234 (2017).

Alaoui-Ismaili et al., "Design of second generation therapeutic recombinant bone morphogenetic proteins," Cytokine & Growth Factor Reviews, 20: 501-507 (2009).

Allen et al., "Therapeutic peptidomimetic strategies for autoimmune diseases: costimulation blockade," The Journal of Peptide Research, 65(6): 591-604 (2005).

Anderson et al., "Multiple sclerosis, seizures, and antiepileptics: role of IL-18, IDO, and melatonin," European Journal of Neurology, 18(5): 680-685 (2011).

Angelini et al., "Analysis of HLA DP, DQ, and DR alleles in adult Italian rheumatoid arthritis patients," Human Immunology, 34(2): 135-141 (1992).

Arbour et al., "A new clinically relevant approach to expand myelin specific T cells," Journal of Immunological Methods, 310(1-2): 53-61 (2006).

Armitage et al., "CD40L: a multi-functional ligand," Seminars in Immunology, 5: 401-412 (1993).

Aruffo et al., "The CD40 Ligand, gp39, is Defective in Activated T Cells from Patients with X-Linked Hyper-IgM Syndrome," Cell, 72: 291-300 (1993).

Attwood et al., "The Babel of Bioinformatics," Science, 290(5491): 471-473 (2000).

Bai et al., "Cerebrospinal Fluid and Blood Cytokines as Biomarkers for Multiple Sclerosis: A Systematic Review and Meta-Analysis of 226 Studies With 13,526 Multiple Sclerosis Patients," *Front. Neurosci.*, 2019, 13: 1026.

Baker et al., "CD40 on NOD CD4 T cells contributes to their activation and pathogenicity," Journal of Autoimmunity, 31(4): 385-392 (2008).

Balasa et al., "CD40 Ligand-CD40 Interactions are Necessary for the Initiation of Insulitis and Diabetes in Nonobese Diabetic Mice," The Journal of Immunology, 159: 4620-4627 (1997).

Barker et al., "Prediction of Autoantibody Positivity and Progression to Type 1 Diabetes: Diabetes Autoimmunity Study in the Young (DAISY)," Journal of Clinical Endocrinology & Metabolism, 89(8):3896-3902 (2004).

Becker et al., "CD40, an extracellular receptor for binding and uptake of Hsp70-peptide complexes," The Journal of Cell Biology, 158(7): 1277-1285 (2002).

Bee et al., "Exploring the Dynamic Range of the Kinetic Exclusion Assay in Characterizing Antigen-Antibody Interactions," Plos One, 7(4): e36261 (2012).

Benveniste et al., "Molecular regulation of CD40 gene expression in macrophages and microglia," Brain, Behavior, and Immunity, 18(1): 7-12 (2004).

Bojadzic et al., "CD40-targeting KGYY15 peptides do not efficiently block the CD40-CD40L interaction," Diabetologia, 62: 2158-2160 (2019).

Bonifacio, "Predicting Type 1 Diabetes Using Biomarkers," Diabetes Care, 38: 989-996 (2015).

Boon et al., "Prevention of Experimental Autoimmune Encephalomyelitis in the Common Marmoset (*Allithrix jacchus*) Using a Chimeric Antagonist Monoclonal Antibody Against Human CD40 is Associated with Altered B Cell Response," J. Immunol., 167: 2942-2949 (2001).

Bourgeois et al., "A Role for CD40 Expression on CD8+ T cells in the Generation of CD8+ T Cell Memory," Science, 297: 2060-2063 (2002).

Bowie et al., "Deciphering the Message in Protein Sequences: Tolerance to Amino Acid Substitutions," Science, 247(4948): 1306-1310 (1990).

Bretscher, "The two-signal model of lympocyte activation twenty-one years later," Immunology Today, 13(2): 74-76 (1992).

Burge et al., "The Role of a Coronary Artery Calcium Scan in Type 1 Diabetes," Diabetes Technology & Therapeutics, 18(9): 594-603 (2016).

Burgess et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," The Journal of Cell Biology, 111:2129-2138 (1990).

Buzzard et al., "Multiple Sclerosis: Basic and Clinical," Adv. Neurobiol., 2017, 15: 211-252.

Campean et al., "CD40-CD154 expression in calcified and non-calcified coronary lesions of patients with chronic renal failure," Atherosclerosis, 190(1): 156-166 (2007).

Carter et al., "CD40 engagement of CD4+CD40+ T cells in a neo-self antigen disease model ablates CTLA-4 expression and indirectly impacts tolerance," European Journal of Immunology, 42: 424-435 (2012).

Ceccarelli et al., "Microglia extracellular vesicles: focus on molecular composition and biological function," *Biochem. Soc. Trans.*, 2021, 49(4): 1779-1790.

Chatzigeorgiou et al., "Blocking CD40-TRAF6 signaling is a therapeutic target in obesity-associated insulin resistance," PNAS, 111(7): 2686-2691 (2014).

Chen et al., "CD40/CD40L dyad in the inflammatory and immune responses in the central nervous system," *Cell Mol. Immunol.*, 2006, 3(3): 163-169.

Christensen et al., "Systemic Inflammation in Progressive Multiple Sclerosis Involves Follicular T-Helper, Th17- and Activated B-Cells and Correlates with Progression," PLOS ONE, 8(3): e57820 (2013).

(56) References Cited

OTHER PUBLICATIONS

Cipollone et al., "Enhanced soluble CD40 ligand contributes to endothelial cell dysfunction in vitro and monocyte activation in patients with diabetes mellitus: effect of improved metabolic control," Diabetologia, 48: 1216-1224 (2005).
Cooper et al., "Cutting Edge: TCR Revision Occurs in Germinal Centers," The Journal of Immunology, 173: 6532-6536 (2004).
Davidson et al., "Co-Stimulatory Blockade in the Treatment of Murine Systemic Lupus Erythematosus," Ann. NY Acad. Sci, 987: 188-198 (2003).
De Ramon et al., "CD154-CD40 T-cell co-stimulation pathway is a key mechanism in kidney ischemia-reperfusion injury," Kidney International, 88: 538-549 (2015).
Deambrosis et al., "Inhibition of CD40-CD154 costimulatory pathway by a cyclic peptide targeting CD154," J. Mol. Med., 87: 181-197 (2009).
DeGraba et al., "Efficacy of an Interdisciplinary Intensive Outpatient Program in Treating Combat-Related Traumatic Brain Injury and Psychological Health Conditions," *Front Neurol*, 2020, 11: 580182.
Devaraj et al., "Increased Monocytic Activity and Biomarkers of Inflammation in Patients With Type 1 Diabetes," Diabetes, 55: 774-779 (2006).
Druzd et al., "Lymphocyte Circadian Clocks Control Lymph Node Trafficking and Adaptive Immune Responses," Immunity, 2017; 46: 120-32 [PubMed: 28087238].
Durie et al., "Prevention of Collagen-Induced Arthritis with an Antibody to gp39, the Ligand for CD40," Science, 261: 1328-1330 (1993).
Edwards et al., "Interleukin-6 is associated with acute concussion in military combat personnel," *BMC Neurol.*, 2020, 20(1): 209.
Elliott et al., "Chronic white matter lesion activity predicts clinical progression in primary progressive multiple sclerosis," *Brain a Journal of Neurology*, 2019, 142(9): 2787-2799.
Ellmark et al., "Modulation or the CD40-CD40 ligand interaction using human anti-CD40 single-chain antibody fragments obtained from the n-CoDeR phage display library," Immunology, 106: 456-463 (2002).
Eshaghi et al., "Progression of regional grey matter atrophy in multiple sclerosis," *Brain a Journal of Neurology*, 2018, 141(6): 1665-1677.
Fan et al., "The emerging role of exosome-derived non-coding RNAs in cancer biology," *Cancer Lett.*, 2018, 414: 107-115.
Fanslow et al., "Recombinant CD40 Ligand Exerts Potent Biologic Effect on T Cells," Journal of Immunology, 152: 4262-4269 (1994).
Fisniku et al., "Disability and T2 MRI lesions: a 20-year follow-up of patients with relapse onset of multiple sclerosis," Brain, 131(3): 808-817 (2008).
Fox, "Clinical features, pathogenesis, and treatment of Sjogren's syndrome," Current Opinion in Rheumatology, 8(5): 438-445 (1996) (Abstract Only).
Garlichs et al., "Upregulation of CD40 and CD40 ligand (CD154) in patients with moderate hypercholesterolemia," Circulation, 104: 2395-2400 (2001).
Gerritse et al., "CD40-CD40 ligand interactions in experimental allergic encephalomyelitis and multiple sclerosis," PNAS, 93: 2499-2504 (1996).
Girvin et al., "CD40/CD40L Interaction is Essential for the Induction of EAE in the Absence of CD28-Mediated Co-stimulation," Journal of Autoimmunity, 18(2): 83-94 (2002).
Giuliani et al., "Minocycline attenuates T cell and microglia activity to impair cytokine production in T cell-microglia interaction," Journal of Leukocyte Biology, 78: 135-143 (2005).
Goetzl et al., "Altered levels of plasma neuron-derived exosomes and their cargo proteins characterize acute and chronic mild traumatic brain injury," *FASEB Jour.*, 2019, 33(4): 5082-5088.
Goetzl et al., "Traumatic brain injury increases plasma astrocyte-derived exosome levels of neurotoxic complement proteins," *FASEB Jour.*, 2020, 34(2): 3359-3366.

Goodnow, "Pathways for self-tolerance and the treatment of autoimmune diseases," Lancet, 357: 2115-2121 (2001).
Goverman et al., "Transgenic mice that express a myelin basic protein-specific T cell receptor develop spontaneous autoimmunity," Cell, 72(4): 3018-3027 (1993).
Graber et al., "Interleukin-17 in transverse myelitis and multiple sclerosis," Journal of Neuroimmunology, 196(1-2): 124-132 (2008).
Grabstein, "The Regulation or T Cell-Dependent Antibody Formation in Vitro by CD40 Liqand and IL-2," The Journal of Immunology, 150(8): 3141-3147 (1993).
Grossman, "Avoiding Tolerance Against Prostatic Antigens With Subdominant Peptide Epitopes," Journal of Immunotherapy, 23(3): 237-241 (2001).
Guo et al., "CD40L-Dependant Pathway is Active at Various Stages of Rheumatoid Arthritis Disease Progression," The Journal of Immunology, 198: 4490-4501 (2017).
Guo et al., "Protein tolerance to random amino acid change," PNAS, 101(25): 9205-9210 (2004).
Hafler et al., "Risk alleles for multiple sclerosis identified by a genomewide study," New England Journal of Medicine, 357(9): 851-862 (2007).
Hamlett et al., "Neuronal exosomes reveal Alzheimer's disease biomarkers in Down syndrome," *Alzheimers Dement.*, 2017, 13(5): 541-549.
Harrington et al., "Differential tolerance is induced in T cells recognizing distinct epitopes of myelin basic protein," Immunity, 8(5): 571-580 (1998).
Hart et al., "Preclinical assessment of therapeutic antibodies against human CD40 and human interleukin-12/23p40 in a nonhuman primate model of multiple sclerosis," *Neurodegener. Dis.*, 2008, 5(1): 38-52.
Hartung et al., "Diagnosis of multiple sclerosis: revisions of the McDonald criteria 2017—continuity and change," *Curr. Opin. Neurol.*, 2019, 32(3): 327-337.
Heath et al., "Monoclonal antibodies to murine CD40 define two distinct functional epitopes," Eur. J. Immunol., 24: 1828-1834 (1994).
Hemmer et al., "New concepts in the immunopathogenesis of multiple sclerosis," Nature Reviews Neuroscience, 3(4): 291-301 (2002).
Hernandez et al., "CD40-CD40 Ligand Interaction between Dendritic Cells and CDS+ T Celis is Needed to Stimulate Maximal T Cell Responses in the Absence of CD4+ T Cell Help," The Journal of Immunology, 178: 2844-2852 (2007).
Hoffjan et al., "The genetics of multiple sclerosis: an update 2010," Molecular and Cellular Probes, 24(5): 237-243 (2010).
Homann et al., "CD40L Blockade Prevents Autoimmune Diabetes by Induction of Bitypic NK/DC Reaulatorv Geils," Immunity, 16: 403-415 (2002).
Howard et al., "Immunotherapy Targeting the CD40/CD154 Costimulatory Pathway for Treatment of Autoimmune Disease," Autoimmunity, 37(5): 411-418 (2004).
Huseby et al., "A pathogenic role for myelin-specific CD8+ T cells in a model for multiple sclerosis," Journal of Experimental Medicine, 194(5): 669-676 (2001).
Ichikawa et al., "Increased Fas antigen on T cells in multiple sclerosis," Journal of Neuroimmunology, 71(1-2): 125-129 (1996).
Iezzi et al., "CD40-CD40L cross-talk integrates strong antigenic signals and microbial stimuli to induce development of IL-17-producing CD4+ T cells," Proc Natl Acad Sci USA, 106: 876-881 (2009).
Ilonen et al., "Abnormalities within CD4 and CD8 T lymphocyte subsets in type 1 (insulin-dependent) diabetes," Clin. exp. Immunol., 85(2): 278-281 (1991).
Jensen et al., "Increased T cell expression of CD154 (CD40-ligand) in multiple sclerosis," European Journal of Neurology, 8: 321-328 (2001).
Kalatha et al., "Glial and neuroaxonal biomarkers in a multiple sclerosis (MS) cohort," *Hell. J. Nucl .Med.*, 2019, 22 Suppl 2: 113-121.
Karpusas et al., "2 .ANG. crystal structure of an extracellular fragment of human CD40 ligand," Structure, 3,(10): 1031-1039 (1995).

(56) References Cited

OTHER PUBLICATIONS

Kennedy et al., "Acute Exercise Induces GLUT4 Translocation in Skeletal Muscle of Normal Human Subjects and Subjects With Type 2 Diabetes," Diabetes, 48: 1-6 (1999).
Kent et al., "Expanded T cells from pancreatic lymph nodes of type 1 diabetic subjects recognize an insulin epitope," Nature, 435(7039): 224-228 (2005).
Khambhati et al., "Immunotherapy for the prevention of atherosclerotic cardiovascular disease: Promise and possibilities," Atherosclerosis 276: 1-9 (2018).
Khan et al., "Differential peptide binding to CD40 evokes counteractive responses," Human Immunology, 73: 465-469 (2012).
King et al., "The Use of Animal Models in Diabetes Research," British Journal of Pharmacology, 166: 877-894 (2012).
Kitagawa et al., "Identification of three novel peptides that inhibit CD40-CD154 interaction," Mod. Rheumatol, 15: 423-426 (2005).
Kobata et al., "Role of costimulatory molecules in autoimmunity," Reviews in Immunogenetics, 2: 74-80 (2000).
Kuo et al., "IL-17 and CD40 ligand synergistically stimulate the chronicity of diabetic nephropathy," Nephrol Dial Transplant, 33: 248-256 (2018).
Kutzelnigg et al., "Cortical demyelination and diffuse white matter injury in multiple sclerosis," *Brain a Journal of Neurology*, 2005, 128(Pt 11): 2705-2712.
Laemmli ., "Cleavage of Structural Proteins during the Assembly of the Head of Bacteriophage T4," Nature, 227: 680-685 (1970).
Laman et al., "Protection of marmoset monkeys against EAE by treatment with a murine antibody blocking CD40 (mu5D12)," Eur. J. Immunol., 32: 2218-2228 (2002).
Laman et al., "Therapy with antibodies against CD40L (CD154) and CD44-variant isoforms reduces experimental autoimmune encephalomyelitis induced by a proteolipid protein peptide," Multiple Sclerosis, 4: 147-153 (1998).
Lederman et al., "Identification of a Novel Surface Protein on Activated CD4+ T Cells That Induces Contact-dependant B Cell Differentiation (Help)," J. Exp. Med., 175: 1091-1101 (1992).
Lederman et al., "Molecular Interactions Mediating T-B Lymphocyte Collaboration in Human Lymphoid Follicles: Roles of T Cell-B Cell-Activating Molecule (5c8 Antigen) and CD40 in Contact-Dependent Help," The Journal of Immunology, 149(12): 3817-3826 (1992).
Ledreux et al., "Assessment of Long-Term Effects of Sports-Related Concussions: Biological Mechanisms and Exosomal Biomarkers," *Front. Neurosci.* 2020, 14: 761.
Ledreux et al., "Small Neuron-Derived Extracellular Vesicles from Individuals with Down Syndrome Propagate Tau Pathology in the Wildtype Mouse Brain," *J. Clin. Med.*, 2021, 10(17): 3931.
Lee et al., "Mouse models of atherosclerosis: a historical perspective and recent advances," Lipids in Health and Disease, 16: 1-11 (2017).
Liu et al., "CD127 expression inversely correlates with FoxP3 and suppressive function of human CD4+T reg cells," Journal of Experimental Medicine, 203(7): 1701-1711 (2006).
Liu et al., "NG2 glia are required for maintaining microglia homeostatic state," *Glia*, 2020, 68(2): 345-355.
Liu et al., "Targeted exosome-mediated delivery of opioid receptor Mu siRNA for the treatment of morphine relapse," *Sci. Rep.*, 2015, 5: 17543.
Lovett-Racke et al., "Decreased dependence of myelin basic protein-reactive T cells on CD28-mediated costimulation in multiple sclerosis patients," Journal of Clincial Investigation, 101(4): 725-730 (1998).
Lucchinetti et al., "Inflammatory Cortical Demyelination in Early Multiple Sclerosis," New England Journal of Medicine, 365(23): 2188-2197 (2011).
Lutgens et al., "Long-term reversal of hypercholesterolemia in low density lipoprotein receptor (LDLR)-deficient mice by adenovirus-mediated LDL54 gene transfer combined with CD154 blockade," Nature Medicine, 5: 1313-1316 (1999).

Lutterotti et al., "Antigen-specific tolerance by autologous myelin peptide-coupled cells: a phase 1 trial in multiple sclerosis," Science Translational Medicine, 5(188) 20 pages (2013).
Macaron et al., "Diagnosis and Management of Progressive Multiple Sclerosis," *Biomedicines*, 2019, 7(56): 23 pages.
Mackey et al., "Calcifications, arterial stiffness, and atherosclerosis," Atherosclerosis, Large Arteries and Cardiovascular Risk. Adv Cardiol., 44: 234-244 (2008).
Maggi et al., "Chronic White Matter Inflammation and Serum Neurofilament Levels in Multiple Sclerosis," *Neurology* 2021, 97(6): e543-e553.
Marsh, "Nomenclature for factors of the HLA system, updated Jan. 2012," Human Immunology, 73: 593-596 (2012).
Mayo Clinic Diabetes, mayoclinic.org/diseases-conditions/diabetes/symptoms-causes/syc-2037 1444?; pp. 1-7; mayoclinic.org/diseases-conditions/diabetes/diagnosis-treatment/drc-20371451?p=1; pp. 1-1 1, downloaded Feb. 20, 2012. (Year: 2012).
Mayo Clinic: Arteriosclerosis / Athersclerosis, mayoclinic.org/diseases-conditions/arteriosclerosis atherosclerosis/symptoms-causes /syc-20350569?, pp. 1-4; mayoclinic.org/diseases-conditions/arteriosclerosis- atherosclerosis/diagnosis-treatment/drc-20350575 ?p=1; pp. 1-7; downloaded Feb. 10, 2021. (Year: 2021).
McMahon et al., "Epitope spreading initiates in the CNS in two mouse models of multiple sclerosis," Nature Medicine, 11(3): 335-339 (2005).
Mcwhirter et al., "Crystallographic analysis of CD40 recognition and signaling by human TRAF2," Proc. Natl. Acad. Sci. USA, 96: 8408-8413 (1999).
Miller et al., "Antigen presentation in the CNS by myeloid dendritic cells drives progression of relapsing experimental autoimmune encephalomyelitis," Annals of the New York Academy of Sciences, 1103: 179-191 (2007).
Miller et al., "Clinically isolated syndromes," Lancet Neurology, 11(2): 157-169 (2012).
Miller et al., "The role of magnetic resonance techniques in understanding and managing multiple sclerosis," Brain, 121: 3-24 (1998).
Miller et al., "Virus-induced autoimmunity: epitope spreading to myelin autoepitopes in Theiler's virus infection of the central nervous system," Advances in Virus Research, 56: 199-217 (2001).
Munroe et al., "Pro-Inflammatory• Adaptive Cytokines and Shed Tumor Necrosis Factor Receptors are Elevated Preceding Systemic Lupus Erythematosus Disease Flare," Arthritis Rheumatol., 66(7): 1888-1899 (2014).
Najafian et al., "T cell costimulatory pathways: blockade for auto-immunity," *Expert Opin. Biol. Ther.*, 2003, 3(2): 227-236.
Nguyen et al., "CD+CD40+ T cell levels predict risk of developing type I diabetes pre-diabetics," J Invest Med, Abstract, 62(1): 151-152 (2014).
Nyakeriga et al., "TCR-induced T cell activation leads to simultaneous phosphorylation at Y505 and Y394 of p56(1ck) residues," Cytometry A, 81(9): 797-805 (2012).
O'Connor et al., "Antibodies from inflamed central nervous system tissue recognize myelin oligodendrocyte glycoprotein," Journal of Immunology, 175(3): 1974-1982 (2005).
Ontaneda., "Progressive Multiple Sclerosis," *Continuum (Minneap Minn)*, 2019, 25(3): 736-752.
Pawson et al., "Assembly of Cell Regulatory Systems Through Protein Interaction Domains," Science, 300: 445-452 (2003).
Peng et al., "Microglia-Derived Exosomes Improve Spinal Cord Functional Recovery after Injury via Inhibiting Oxidative Stress and Promoting the Survival and Function of Endothelia Cells," *Oxid. Med. Cell Longev.*, 2021, 2021: 1695087.
Poggi et al., "The inflammatory receptor CD40 is expressed on human adipocytes: contribution to crosstalk between lymphocytes and adipocytes," Diabetologia, 52: 1152-1163 (2009).
Polman et al., "Diagnostic criteria for multiple sclerosis: 2010 revisions to the McDonald criteria," Annals of Neurology, 69(2): 292-302 (2011).
Polman et al., "Drug treatment of multiple sclerosis," Medicine Cabinent, 173: 398-402 (2000).
Polman et al., "Multiple sclerosis diagnostic criteria: three years later," Multiple Sclerosis Journal, 11(1): 5-12 (2005).

(56) References Cited

OTHER PUBLICATIONS

Pullen et al., "CD40 Signaling through Tumor Necrosis Factor Receptor-associated Factors (TRAFs)," The Journal of Biological Chemistry, 274(20): 14246-14254 (1999).
Pulliam et al., "Plasma neuronal exosomes serve as biomarkers of cognitive impairment in HIV infection and Alzheimer's disease," J. Neurovirol., 2019, 25(5): 702-709.
Quezada et al., "Distinct Mechanisms of Action of Anti-CD154 in Early Versus Late Treatment of Murine Lupus Nephritis," Arthritis & Rheumatism, 48(9): 2541-2554 (2003).
Ramsdell et al., "CD40 Ligand Acts as a Costimulatory Signal for Neonatal Thymic Gamma Delta T Cells," The Journal of Immunology, 152: 2190-2197 (1994).
Resetkova et al., "Antibody to gp39, the Ligand for CD40 Significantly Inhibits the Humoral Response from Graves' Thyroid Tissues Xenografted into Severe Combined Immunodeficient (SCID) Mice," Thyroid, 6(4): 267-273 (1996).
Richards et al., "A peptide containing a novel FPGN CD40-binding sequence enhances adenoviral infection of murine and human dendritic cells," Eur. J. Biochem., 270: 2287-2294 (2003).
Rolink et al., "The SCID but Not the RAG-2 Gene Product is Required for S?- S? Heavy Chain Class Switching," Immunity, 5(4): 319-330 (1996).
Rosetti et al., "The many faces of Mac-1 in autoimmune disease," Immunological Reviews, 269: 175-193 (2016).
Ruiz et al., "Resolution of inflammation during multiple sclerosis," Semin. Immunopathol., 2019, 41(6): 711-726.
Russo et al., "Platelet-Activating Factor Mediates CD40-Dependent Angiogenesis and Endothelial-Smooth Muscle Cell Interaction," The Journal of Immunology, 5489-5497 (2003).
Santilli et al., "CD40/CD40L system and vascular disease," Intern. Emerg. Med., 2007, 2(4): 256-268.
Sarawar et al., "Stimulation via CD40 can substitute for CD4 T cell function in preventing reactivation of latent herpesvirus," PNAS, 98: 6325-6329 (2001).
Sawcer et al., "Genetic risk and a primary role for cell-mediated immune mechanisms in multiple sclerosis," Nature, 476(7359): 214-219 (2011).
Sawcer, "The complex genetics of multiple sclerosis: pitfalls and prospects," Brain, 131: 3118-3131 (2008).
Schonbeck et al., "Molecules in focus, CD154 (CD40 ligand)," The International Journal of Biochemistry & Cell Biology 32: 687-693 (2000).
Schonbeck et al., "The CD40/CD154 receptor/ligand dyad," CMLS—Cellular and Molecular Life Sciences, 58: 4-43 (2001).
Schuh et al., "Features of Human CD3+CD20+ T Cells," J. Immunol., 2016, 197(4): 1111-1117.
Seijkens et al., "CD40-CD40L: linking pancreatic, adipose tissue and vascular inflammation in type 2 diabetes and its complications," Diab Vasc Dis Res, 10: 115-122 (2012).
Seko et al., "Expression of Tumor Necrosis Factor (TNF) Receptor/Ligand Superfamily Co-Stimulatory Molecules CD40, CD30L, CD27L, and Ox40L in Murine Hearts with Chronic Ongoing Myocarditis Caused by Coxsackie Virus B3," J. Pathol., 188: 423-430 (1999).
Sharma et al., "Glioma-derived exosomes drive the differentiation of neural stem cells to astrocytes," PLoS One 2020, 15(7): e0234614.
Siebert et al., "An analytical workflow for investigating cytokine profiles," Cytometry A, 73(4): 289-298 (2008).
Siracusa et al., "Astrocytes: Role and Functions in Brain Pathologies," Front. Pharmacol. 2019, 10: 1114.
Skolnick et al., "From genes to protein structure and function: novel applications of computational approaches in the genomic era," Trends in Biotech, 18: 34-39 (2000).
Smith et al., "Multi-peptide coupled-cell tolerance ameliorates ongoing relapsing EAE associated with multiple pathogenic autoreactivities," Journal of Autoimmunity, 27(4): 218-231 (2007).
Steck et al., "Genetics of type 1 cliabetes," Clinical Chemistry, 57(2): 176-185 (2011).
Stein et al., "Long-term reversal of hypercholesterolemia in low density lipoprotein receptor (LDLR)-deficient mice by adenovirus-mediated LDLR gene transfer combined with CD154 blockade," The Journal of Gene Medicine, 2(1): 41-51 (2000).
Stumpf et al., "Enhanced levels or CD154 (CD40 ligand) on platelets in patients with chronic heart failure," The European Journal of Heart Failure, 5: 629-637 (2003).
Stys et al., "Recent advances in understanding multiple sclerosis," F1000Res, 2019, 8: 8 pages.
Sun et al., "Characterization and Biomarker Analyses of Post-COVID-19 Complications and Neurological Manifestations," Cells, 2021, 10(386): 17 pages.
Sun et al., "Co-stimulation agonists as a new immunotherapy for autoimmune diseases," TRENDS in Molecular Medicine, 9(11): 483-489 (2003).
Takada et al., "Integrin Binding to the Trimeric Interface of CD40L Plays a Critical Role in CD40/CD40L Signaling," J. Immunol., 203: 1383-1391 (2019).
Takahashi et al., "The role of extracellular vesicle microRNAs in cancer biology," Clin. Chem. Lab Med., 2017, 55(5): 648-656.
Takeda et al., "Neuronal Differentiation of Human Mesenchymal Stem Cells Using Exosomes Derived from Differentiating Neuronal Cells," PLoS One, 2015, 10(8): e0135111.
Thorsby et al., "Particular HLA-DQ molecules play a dominant role in determining susceptibility or resistance to Type 1 (insulin-dependent) diabetes mellitus," Diabetologia, 36(5): 371-377 (1993)(Abstract Only).
Thouvenot., "Update on clinically isolated syndrome," Presse Med., 2015, 44(4 Pt 2): e121-136.
Toubi et al., "The Role of CD40-CD154 Interactions in Autoimmunity and the Benefit of Disrupting this Pathway," Autoimmunity, 37: 457-464 (2004).
Townsend et al., "CD40 signaling regulates innate and adaptive activation of microglia in response to amyloid b-peptide," Eur. J. Immunol., 35: 901-910 (2005).
Vaitaitis et al, "Cutting Edge: CD40-Induced Expression of Recombination Activating Gene (RAG) 1 and RAG2: A Mechanism for the Generation of Autoaggressive T Cells in the Periphery," The Journal of Immunology, 170: 3455-3459 (2003).
Vaitaitis et al., "A CD40 targeting peptide prevents severe symptoms in experimental autoimmune encephalomyelitis," J. Neuroimmunol., 2019, 332: 8-15.
Vaitaitis et al., "A CD40-targeted peptide controls and reverses type 1 diabetes in NOD mice," Diabetologia, 57: 2366-2373 (2014).
Vaitaitis et al., "An Alternative Role for Foxp3 as an Effector T Cell Regulator Controlled through CD40," The Journal of Immunology, 191: 717-725 (2013).
Vaitaitis et al., "Biomarker discovery in pre-Type 1 Diabetes; Th40 cells as a predictive risk factor," J. Clin. Endocrinol. Metab., 2019, 104(9): 4127-4142.
Vaitaitis et al., "CD40 glycoforms and TNF-receptors 1 and 2 in the formation of CD40 receptor(s) in autoimmunity," Molecular Immunology, 47: 2303-2313 (2010).
Vaitaitis et al., "CD40 interacts directly with RAG1 and RAG2 in autoaggressive T cells and Fas prevents CD40 induced RAG expression," Cellular and Molecular Immunology, 10(6): 483-489 (2013).
Vaitaitis et al., "CD40-mediated signalling influences trafficking, T-cell receptor expression, and T-cell pathogenesis, in the NOD model of type 1 diabetes," Immunology, 152: 243-254 (2017).
Vaitaitis et al., "CD40-targeted peptide proposed for type 1 diabetes therapy lacks relevant binding affinity to its cognate receptor Reply to Pagni PP, Wolf A, Lo Conte M et al [letter]," Diabetologia, 62: 1730-1731 (2019).
Vaitaitis et al., "Galectin-9 Controls CD40 Signaling through a Time Independent Mechanism and Redirects the Cytokine Profile of Pathogenic T Cells in Autoimmunity," PLoS ONE, 7(6): e38708:1-13 (2012).
Vaitaitis et al., "High Distribution of CD40 and TRAF2 in TMO T Cell Rafts Leads to Preferential Survival of this Auto-Aggressive Population in Autoimmunity," PLoS ONE, 3(4): e2076: 1-11 (2008).

(56) References Cited

OTHER PUBLICATIONS

Vaitaitis et al., "Th40 cells (CD4+CD40+ Tcells) drive a more severe form of Experimental Autoimmune Encephalomyelitis than conventional CD4 T cells," PLoS ONE, 12: e0172037 pp. 1-24 (2017).
Vaitaitis et al., "The Expanding Role of TNF-Receptor Super Family Member CD40 (tnfrsf5) in Autoimmune Disease: Focus on Th40 Cells," Current Immunology Reviews, 6(2): 130-136 (2010).
Van Kooten et al., "CD40-CD40 ligand," J. Leukoc. Biol., 2000, 67(1): 2-17.
Varo et al., "Soluble CD40L—Risk Prediction After Acute Coronary Syndromes," Circulation, 108: 1049-1052 (2003).
Vaz et al., "Phenotypic Effects of Wild-Type and Mutant SOD1 Expression in N9 Murine Microglia at Steady State, Inflammatory and Immunomodulatory Conditions," Front. Cell. Neurosci., 2019, 13: 109.
Verma et al., "Not Just an Adhesion Molecule: LFA-1 Contact Tunes the T Lymphocyte Program," The Journal of Immunology, 199: 1213-1221 (2017).
Wagner et al., "Expression of CD40 identifies a unique pathogenic T cell population in type 1 diabetes," PNAS, 99(6): 3782-3787 (2002).
Wagner et al., "Increased expression of CD40 on thymocytes and peripheral T cells in autoimmunity: A mechanism for acquiring changes in the peripheral T cell receptor repertoire," International Journal of Molecular Medicine, 4: 231-242 (1999).
Waid et al., "A unique T cell subset described as CD4loCD40+ T cells (TCD40) in human type 1 diabetes," Clinical Immunology, 124: 138-148 (2007).
Waid et al., "A unique T cell subset, Th40, are pathogenic and diagnostic in mulitple sclerosis," Journal of Immunology, 186(1): Meeting Abstract (2011).
Waid et al., "Defining a New Biomarker for the Autoimmune Component of Multiple Sclerosis: Th40 cells," J. Neuroimmunol., 270: 75-85 (2014).
Waid et al., "Disruption of the homeostatic balance between autoaggressive (CD4+CD40+) and regulatory (CD4+CD25+FoxP3+) T cells promotes diabetes," Journal of Leukocyte Biology, 84: 431-439 (2008).
Waid et al., "Peripheral CD4loCD40+ auto-aggressive T cell expansion during insulin-dependent diabetes mellitus," Eur. J. Immunol, 34: 1488-1497 (2004).
Walling et al., "LFA-1 in T Cell Migration and Differentiation," Frontiers in Immunology, 9: Article 952 (2018).
Winer et al., "B Lymphocytes promote insulin resistance through modulation of T Lymphocytes and production of pathogenic IgG antibody," Nat Med, 17: 610-617 (2011).
Winston et al., "Assessing Neuronal and Astrocyte Derived Exosomes From Individuals With Mild Traumatic Brain Injury for Markers of Neurodegeneration and Cytotoxic Activity," Front. Neurosci., 2019, 13: 1005.
Wucherpfennig et al., "A Review of T-Cell Receptors in Multiple Sclerosis: Clonal Expansion and Persistence of Human T-Cells Specific for an Immunodominant Myelin Basic Protein Peptidea," Annals of the New York Academy of Sciences, 756(1): 241-258 (1995).
Yu et al., "Reduced oligodendrocyte exosome secretion in multiple system atrophy involves SNARE dysfunction," Brain a Journal of Neurology,, 2020, 143(6): 1780-1797.
Yu et al., "Targeting CD40 with a Selective Phage Display Derived Peptide," pp. 61-74.
Zhang et al., "T cell and antibody responses in remitting-relapsing experimental autoimmune encephalomyelitis in (C57BL/6 x SJL) F1 mice," Journal of Neuroimmunology, 148(1-2): 1-10 (2004).
Zhang et al., "The regulation of integrin function by divalent cations," Cell Adhesion & Migration, 6(1): 20-29 (2012).
Amer. Diabetes Association Diagnosis and Classification of Diabetes Mellitus, Diabetes Care, 2014, 37, Suppl.I :S8 I-S90.
Bak et al., "Physicochemical and Formulation Developability Assessment for Therapeutic Peptide Delivery—A Primer," The AAPS Journal, 17(1): 144-155 (2015).
Biosyn., "Why acetylate and amidate a peptide," accessed on Mar. 22, 2021 at <https://biosyn.com/faq/why-acetylate-and-amidate-apeptide.aspx>: 1 page (2008).
Catchpole et al., "Canine diabetes mellitus: can old dogs teach us new tricks?," Diabetologia, 48: 1948-1956 (2005).
Gottlieb et al., "Managing feline diabetes: current perspectives," Vet Med (Auckl), 9: 33-42 (2018).
Grant application entitled "Developing a small peptide to control autoimmune inflammation in type 1 diabetes" by PI: David H, Wagner and received on Sep. 2, 2016 and publicly available on Jan. 5, 2018, p. 1-46 (2018).
Grossman, "Avoiding Tolerance Against Prostatic Antigens With Subdominant Peptide Epitopes," Journal of Immunotherapy, 24(3): 237-241 (2001).
Hancock., "Preventing and managing diabetes: an exemplar for NCDS," C3 Collaborating for Health: pp. 1-8 (2012).
Harigai, "Involvement of CD40-D154 interaction in immunopathogenesis of collagen diseases and its application to a novel therapeutic strategy", Jpn. J. Clin. Imnunol., 27 (6) 379-388 (2004).
Huang et al., Resolving the Conundrum of Islet Transplantation by Linking Metabolic Dysregulation, Inflammation, and Immune Regulation, Endocrine Reviews, 29(5): 603-630 (2008).
Johnson et al., "Diabetes, Insulin Resistance, and Metabolic Syndrome in Horses," J Diabetes Sci Technol, 6(3): 534-540 (2012).
Leighton et al., "A Practical Review of C-Peptide Testing in Diabetes," Diabetes Ther, 8(3): 475-487 (2017).
Matthews et al., "Utility of murine models for the study of spontaneous autoimmune type 1 diabetes," Pediatric Diabetes, 6: 165-177 (2005).
Nelson et al., "Classification and etiology of diabetes in dogs and cats," Thematic Review, T1-T9 (2014).
O'Kell et al., "Comparative Pathogenesis of Autoimmune Diabetes in Humans, NOD Mice, and Canines: Has a Valuable Animal Model of Type 1 Diabetes Been Overlooked?," Diabetes, 66(7): 1443-1452 (2017).
Partial Supplementary European Search Report for EP Application No. EP 20840056.4 dated Mar. 23, 2023.
Patel et al., "Recent developments in protein and peptide parenteral delivery approaches," Ther. Deliv., 5(3): 337-365 (2014).
Poggi et al., "OP 27 New pathways involved in the cross talk between immune cells and metabolic tissues" Diabelologia 55:[Suppll JS1-S538 (2012).
Pullen et al., "CD40 Signaling through Tumor Necrosis Factor Receptor-associated Factors (TRAFs): Binding Site Specificity and Activation of Downstream Pathways by Distinct TRAFs," J Biol Chem, 274(20): 14246-14254 (1999).
Shukshith et al., "Water for Pharmaceutical Use," Int. J. Pharm. Sci. Rev. Res., 36(1): 199-204 (2016).
Vaitaitis, G.M. et al.—2012—PlosOne—vol. 7, e38708, p. 1-13.
Wang et al., "Parenteral Formulations of Proteins and Peptides: Stability and Stabilizers," Journal of Parenteral Science and Technology, 42(2S): S3-S25 (1988).
Wikipedia, "Phosphate-buffered saline," <https://en.wikipedia.org/wiki/Phosphate-buffered saline>: Accessed on Mar. 25, 2022 (Year: 2022).
Balla et al., "Iron Homeostasis in chronic inflammation" Acta Physiolgica Hungarica, vol. 94, Issue 1-2, pp. 95-106 (2007).
Barichello et al., "Biomarkers for sepsis: more than just fever and leukocytosis—a narrative review" Critical Care, 26:14 (2022).
Barichello et al., "Neurochemical effects of sepsis on the brain" Clinical Science, vol. 137, p. 401-414 (2023).
Barichello et al., "The blood-brain barrier dysfunction in sepsis" Tissue Barriers, vol. 9, No. 1. (2021).
Chew et al., "Soluble CD40L (CD154) is increased in patients with shock" Inflammation Research, vol. 59, p. 979-982 (2010).
Extended European Search Report for EP Application No. 23181309.8 dated Sep. 19, 2023.

(56) References Cited

OTHER PUBLICATIONS

Gambichler et al., "Prognostic Performance of Inflammatory Biomarkers Based on Complete Blood Counts in COVID-19 Patients" Viruses, vol. 15 (2023).

Hager et al., "Affinity and Epitope Profiling of Mouse Anti?CD40 Monoclonal Antibodies", Scandinavian journal of immunology 57.6: 517-524 (2003).

Hao et al., "Increased inflammatory mediators levels are associated with clinical outcomes and prolonged illness in severe COVID-19 patients" International Immunopharmacology, vol. 123 (2023).

Liu et al., "CD11b is a Novel Alternate Receptor for CD154 during Alloimmunity" Am J Transplant, vol. 20, No. 8, p. 2216-2225 (2020).

Matsumoto et al., "The clinical importance of a cytokine network in the acute phase of sepsis" Scientific Reports, vol. 8 (2018).

Michels et al., "CD40-CD40 Ligand Pathway Is a Major Component of Acute Neuroinflammation and Contributes to Long-term Cognitive Dysfunction after Sepsis" Molecular Medicine, vol. 21 (2015).

Nolan et al., "CD40 but Not CD154 Knockout Mice Have Reduced Inflammatory Response in Polymicrobial Sepsis: A Potential Role for *Escherichia coli* Heat Shock Protein 70 in CD40-Mediated Inflammation In Vivo" Shock, vol. 22, No. 6, p. 538-542 (2004).

Sekino et al., "Sepsis-associated brain injury: underlying mechanisms and potential therapeutic strategies for acute and long-term cognitive impairments" Journal of Neuroinflammation, vol. 19 (2022).

Tang et al., "Molecular basis and therapeutic implications of CD40/CD40L immune checkpoint" Pharmacol Ther, vol. 219 (2021).

Urbanski et al., "Serum ferritin/C-reactive protein ratio is a simple and effective biomarker for diagnosing iron deficiency in the context of systemic inflammation" QJM: An International Journal of Medicine (2023).

Yao et al., "Neutrophil to lymphocyte ratio (NLR), platelet to lymphocyte ratio (PLR), and systemic immune inflammation index (SII) to predict postoperative pneumonia in elderly hip fracture patients" Journal of Orthopaedic Surgery and Research (2023).

\* cited by examiner

Figure 24

|  | Observed (Peptide) | Normal |
|---|---|---|
| Clot Time: | 5.8 mins. | (5 - 10 mins.) |
| K: | 2.0 mins. | (1 - 3 mins.) |
| Angle: | 62.5 deg. | (53 - 72 deg.) |
| MA: | 60.0 mm | (50 - 70 mm) |
| LY30: | 5.5% | (0 - 8 %) |
| LY60: | 13.7% | (0 - 15 %) |
| TMA: |  | 6 min. |
| G: | 7.5 K d/sc | (4.5 K - 11.0 K) |
| CI: | -0.9 | (-3 - 3) |
| TPI: | 37.5 / sec. | (5 - 90 sec) |

Figure 25A

| SEQ ID NO: 32 | 24-mer | AASVLQWAKKGYYTMKSNLVMLEN | 4.4 hrs. |
| --- | --- | --- | --- |
| SEQ ID NO: 7 | 15-mer | VLQWAKKGYYTMKSN | >100 hrs. |
| SEQ ID NO: 25 | 13-mer | VLQWAKKGYYTMK | 100 hrs. |
| SEQ ID NO: 24 | 10-mer | WAKKGYYTMK | 2.8 hrs. |
| SEQ ID NO: 5 | 8-mer | AKKGYYTM | 4.4 hrs. |
| SEQ ID NO: 29 | 6-mer | AKKGYY | 4.4 hrs. |

Figure 25B

| SEQ ID NO | AA Sequence | Description | ExPASy Expected Half-Life |
| --- | --- | --- | --- |
| SEQ ID NO:4 | KKGYYT | 6-mer (Form 1) | 1.3 hrs. |
| SEQ ID NO:27 | KGYYTM | 6-mer (Form 2) | 1.3 hrs. |
| SEQ ID NO:28 | AEKGYY | 6-mer (Form 3) | 4.4 hrs. |
| SEQ ID NO: 29 | AKKGYY | 6-mer (Form 4) | 4.4 hrs. |
| SEQ ID NO: 30 | AKGYYT | 6-mer (Form 5) | 4.4 hrs. |

Figure 26

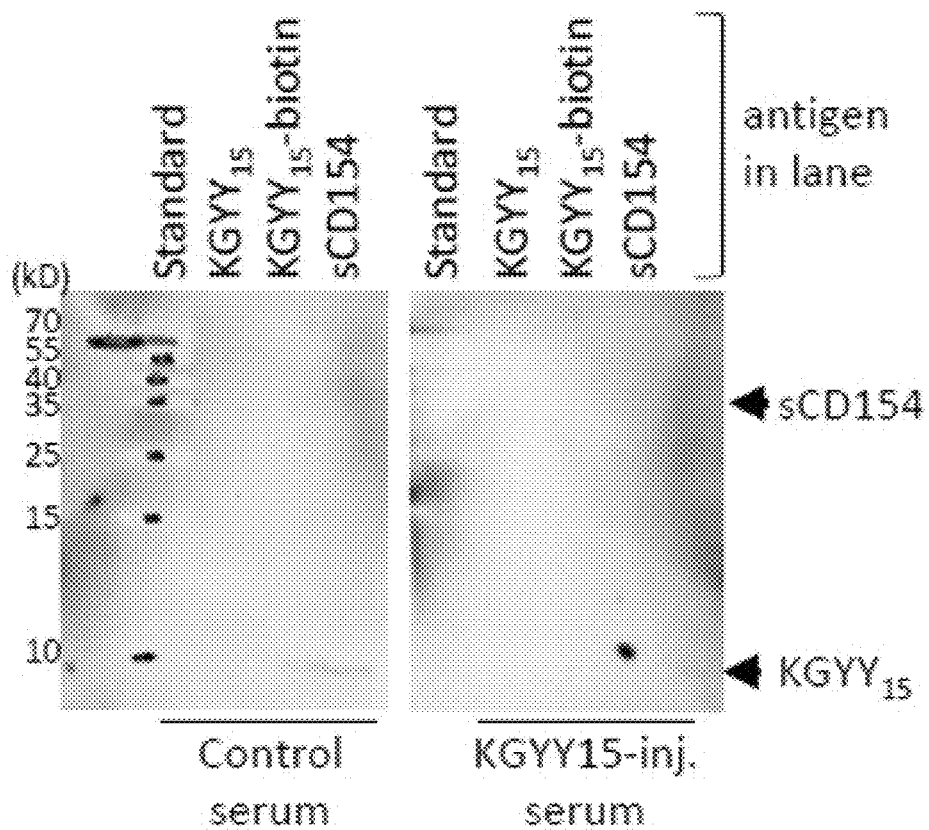

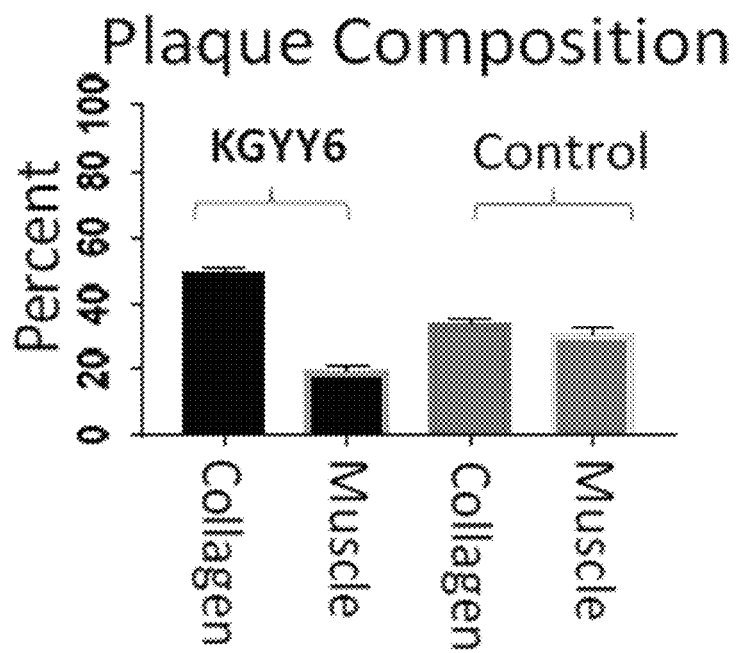
Figure 31
Figure 32A
Figure 32B
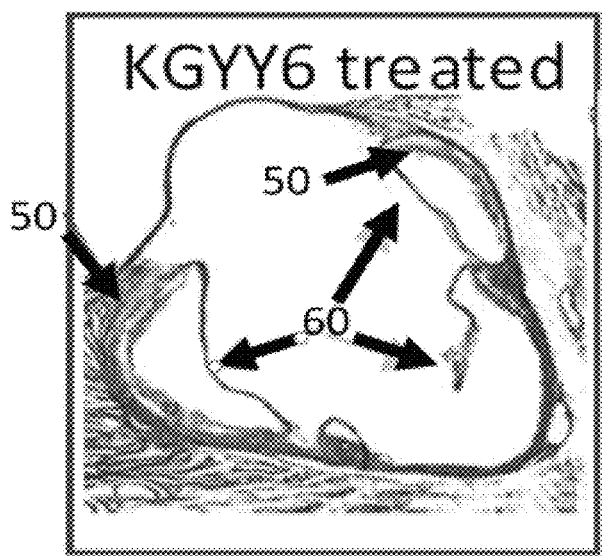
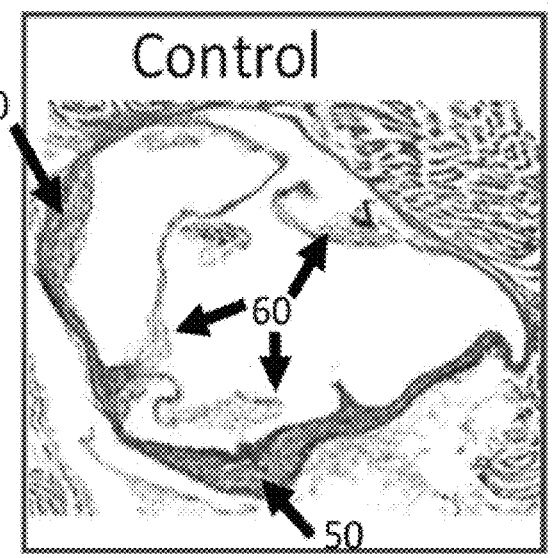

Glut4 Western
6-mer vs Control

SEQUENCE LISTING

```
<160> NUMBER OF SEQ ID NOS: 32

<210> SEQ ID NO 1
<211> LENGTH: 260
<212> TYPE: PRT
<213> ORGANISM: Mus musculus

<400> SEQUENCE: 1

Met Ile Glu Thr Tyr Ser Gln Pro Ser Pro Arg Ser Val Ala Thr Gly
1               5                   10                  15

Leu Pro Ala Ser Met Lys Ile Phe Met Tyr Leu Leu Thr Val Phe Leu
            20                  25                  30

Ile Thr Gln Met Ile Gly Ser Val Leu Phe Ala Val Tyr Leu His Arg
        35                  40                  45

Arg Leu Asp Lys Val Glu Glu Val Asn Leu His Glu Asp Phe Val
    50                  55                  60

Phe Ile Lys Lys Leu Lys Arg Cys Asn Lys Gly Glu Gly Ser Leu Ser
65                  70                  75                  80

Leu Leu Asn Cys Glu Glu Met Arg Arg Gln Phe Glu Asp Leu Val Lys
                85                  90                  95

Asp Ile Thr Leu Asn Lys Glu Glu Lys Lys Glu Asn Ser Phe Glu Met
            100                 105                 110

Gln Arg Gly Asp Glu Asp Pro Gln Ile Ala Ala His Val Val Ser Glu
        115                 120                 125

Ala Asn Ser Asn Ala Ala Ser Val Leu Gln Trp Ala Lys Lys Gly Tyr
    130                 135                 140

Tyr Thr Met Lys Ser Asn Leu Val Met Leu Glu Asn Gly Lys Gln Leu
145                 150                 155                 160
```

```
Thr Val Lys Arg Glu Gly Leu Tyr Tyr Val Tyr Thr Gln Val Thr Phe
            165                 170                 175

Cys Ser Asn Arg Glu Pro Ser Ser Gln Arg Pro Phe Ile Val Gly Leu
            180                 185                 190

Trp Leu Lys Pro Ser Ser Gly Ser Glu Arg Ile Leu Leu Lys Ala Ala
            195                 200                 205

Asn Thr His Ser Ser Ser Gln Leu Cys Glu Gln Gln Ser Val His Leu
            210                 215                 220

Gly Gly Val Phe Glu Leu Gln Ala Gly Ala Ser Val Phe Val Asn Val
225                 230                 235                 240

Thr Glu Ala Ser Gln Val Ile His Arg Val Gly Phe Ser Ser Phe Gly
            245                 250                 255

Leu Leu Lys Leu
            260

<210> SEQ ID NO 2
<211> LENGTH: 261
<212> TYPE: PRT
<213> ORGANISM: Homo sapiens

<400> SEQUENCE: 2

Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
            20                  25                  30

Ile Thr Gln Met Ile Gly Ser Ala Leu Phe Ala Val Tyr Leu His Arg
            35                  40                  45

Arg Leu Asp Lys Ile Glu Asp Glu Arg Asn Leu His Glu Asp Phe Val
50                  55                  60

Phe Met Lys Thr Ile Gln Arg Cys Asn Thr Gly Glu Arg Ser Leu Ser
65                  70                  75                  80

Leu Leu Asn Cys Glu Glu Ile Lys Ser Gln Phe Glu Gly Phe Val Lys
            85                  90                  95

Asp Ile Met Leu Asn Lys Glu Glu Thr Lys Lys Glu Asn Ser Phe Glu
            100                 105                 110

Met Gln Lys Gly Asp Gln Asn Pro Gln Ile Ala Ala His Val Ile Ser
            115                 120                 125

Glu Ala Ser Ser Lys Thr Thr Ser Val Leu Gln Trp Ala Glu Lys Gly
            130                 135                 140

Tyr Tyr Thr Met Ser Asn Asn Leu Val Thr Leu Glu Asn Gly Lys Gln
145                 150                 155                 160

Leu Thr Val Lys Arg Gln Gly Leu Tyr Tyr Ile Tyr Ala Gln Val Thr
            165                 170                 175

Phe Cys Ser Asn Arg Glu Ala Ser Ser Gln Ala Pro Phe Ile Ala Ser
            180                 185                 190

Leu Cys Leu Lys Ser Pro Gly Arg Phe Glu Arg Ile Leu Leu Arg Ala
            195                 200                 205

Ala Asn Thr His Ser Ser Ala Lys Pro Cys Gly Gln Gln Ser Ile His
            210                 215                 220

Leu Gly Gly Val Phe Glu Leu Gln Pro Gly Ala Ser Val Phe Val Asn
225                 230                 235                 240

Val Thr Asp Pro Ser Gln Val Ser His Gly Thr Gly Phe Thr Ser Phe
            245                 250                 255

Gly Leu Leu Lys Leu
            260
```

<210> SEQ ID NO 3
<211> LENGTH: 4
<212> TYPE: PRT
<213> ORGANISM: Mus musculus

<400> SEQUENCE: 3

Lys Gly Tyr Tyr
1

<210> SEQ ID NO 4
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 4

Lys Lys Gly Tyr Tyr Thr
1               5

<210> SEQ ID NO 5
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 5

Ala Lys Lys Gly Tyr Tyr Thr Met
1               5

<210> SEQ ID NO 6
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 6

Ala Glu Lys Gly Tyr Tyr Thr Met
1               5

<210> SEQ ID NO 7
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 7

Val Leu Gln Trp Ala Lys Lys Gly Tyr Tyr Thr Met Lys Ser Lys
1               5                   10                  15

<210> SEQ ID NO 8
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 8

Val Leu Gln Trp Ala Glu Lys Gly Tyr Tyr Thr Met Ser Asn Asn
1               5                   10                  15

<210> SEQ ID NO 9

```
<211> LENGTH: 24
<212> TYPE: PRT
<213> ORGANISM: Artificial Sequence
<220> FEATURE:
<223> OTHER INFORMATION: Synthetic Peptide

<400> SEQUENCE: 9

Asn Ala Ala Ser Val Leu Gln Trp Ala Lys Lys Gly Tyr Tyr Thr Met
1               5                   10                  15

Lys Ser Asn Leu Val Met Leu Glu
            20

<210> SEQ ID NO 10
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 10

Ile Ser Gln Ala Val His Ala Ala His Ala Glu Ile Asn Glu Ala Gly
1               5                   10                  15

Arg

<210> SEQ ID NO 11
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 11

Gly Leu Gln Trp Ala Lys Lys Gly Tyr Tyr Thr Met Lys Ser Asn
1               5                   10                  15

<210> SEQ ID NO 12
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 12

Val Gly Gln Trp Ala Lys Lys Gly Tyr Tyr Thr Met Lys Ser Asn
1               5                   10                  15

<210> SEQ ID NO 13
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 13

Val Leu Gly Trp Ala Lys Lys Gly Tyr Tyr Thr Met Lys Ser Asn
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 14

Val Leu Gln Gly Ala Lys Lys Gly Tyr Tyr Thr Met Lys Ser Asn
```

<210> SEQ ID NO 15
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 15

Val Leu Gln Trp Gly Lys Lys Gly Tyr Tyr Thr Met Lys Ser Asn
1               5                   10                  15

<210> SEQ ID NO 16
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 16

Val Leu Gln Trp Ala Gly Lys Gly Tyr Tyr Thr Met Lys Ser Asn
1               5                   10                  15

<210> SEQ ID NO 17
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 17

Val Leu Gln Trp Ala Lys Gly Gly Tyr Tyr Thr Met Lys Ser Asn
1               5                   10                  15

<210> SEQ ID NO 18
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 18

Val Leu Gln Trp Ala Lys Lys Gly Gly Tyr Thr Met Lys Ser Asn
1               5                   10                  15

<210> SEQ ID NO 19
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 19

Val Leu Gln Trp Ala Lys Lys Gly Tyr Gly Thr Met Lys Ser Asn
1               5                   10                  15

<210> SEQ ID NO 20
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 20

Val Leu Gln Trp Ala Lys Lys Gly Tyr Tyr Gly Met Lys Ser Asn
1               5                   10                  15

<210> SEQ ID NO 21
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 21

Val Leu Gln Trp Ala Lys Lys Gly Tyr Tyr Thr Gly Lys Ser Asn
1               5                   10                  15

<210> SEQ ID NO 22
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 22

Ile Ser Gln Ala Val His Ala Ala His Ala Glu Ile Asn Glu Ala Gly
1               5                   10                  15

Arg

<210> SEQ ID NO 23
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 23

Tyr Val Gln Gly Lys Ala Asn Leu Lys Ser Lys Leu Met Tyr Thr
1               5                   10                  15

<210> SEQ ID NO 24
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 24

Trp Ala Lys Lys Gly Tyr Tyr Thr Met Lys
1               5                   10

<210> SEQ ID NO 25
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 25

Val Leu Gln Trp Ala Lys Lys Gly Tyr Tyr Thr Met Lys
1               5                   10

<210> SEQ ID NO 26
<211> LENGTH: 24
<212> TYPE: PRT
<213> ORGANISM: Artificial Sequence
<220> FEATURE:
<223> OTHER INFORMATION: Synthetic Peptide

<400> SEQUENCE: 26

Ala Ala Ser Val Leu Gln Trp Ala Lys Lys Gly Tyr Tyr Thr Met Lys

```
1               5                   10                  15
Ser Asn Leu Val Val Leu Glu Asn
            20

<210> SEQ ID NO 27
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 27

Lys Gly Tyr Tyr Thr Met
1               5

<210> SEQ ID NO 28
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 28

Ala Glu Lys Gly Tyr Tyr
1               5

<210> SEQ ID NO 29
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 29

Ala Lys Lys Gly Tyr Tyr
1               5

<210> SEQ ID NO 30
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 30

Ala Lys Gly Tyr Tyr Thr
1               5

<210> SEQ ID NO 31
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 31

Tyr Lys Asn Val Lys Gln Met Ala Tyr Trp Leu Thr Gly Lys Ser
1               5                   10                  15

<210> SEQ ID NO 32
<211> LENGTH: 24
<212> TYPE: PRT
<213> ORGANISM: Artificial Sequence
<220> FEATURE:
<223> OTHER INFORMATION: Synthetic Peptide

<400> SEQUENCE: 32
```

```
Ala Ala Ser Val Leu Gln Trp Ala Lys Lys Gly Tyr Tyr Thr Met Lys
1               5                   10                  15

Ser Asn Leu Val Met Leu Glu Asn
            20
```

THERAPEUTIC PEPTIDES AND METHODS FOR TREATING TYPE 2 DIABETES

CROSS-REFERENCE TO RELATED APPLICATION

This application is a continuation of U.S. application Ser. No. 16/240,630, filed on Jan. 4, 2019, which claims the benefit of the U.S. Provisional Application Ser. No. 62/614,262, filed Jan. 5, 2018, and is a continuation-in-part of U.S. application Ser. No. 16/184,129, filed [on Nov. 8, 2018, which claims the benefit of the U.S. Provisional Application Ser. No. 62/669,918, filed on May 10, 2018 and 62/584,595, filed on] Nov. 10, 2017, the entire content of each of which is incorporated herein by reference.

REFERENCE TO SEQUENCE LISTING

This application contains a Sequence Listing submitted as an electronic text file entitled "OPB-00402_SL.txt" having a size in bytes of 11,588 bytes and created Jul. 1, 2021. The information contained in this electronic file is hereby incorporated by reference in its entirety pursuant to 37 CFR 1.52(e)(5).

The present disclosure relates to methods or uses for prevention, modulation, and reduction of cardiovascular disease and/or atherosclerosis in a subject in need of a therapeutically effective amount of a peptide that inhibits the interaction of CD40 and CD154, and the use of such compounds in modulating T-cell activity and in treating disease. Furthermore, the present disclosure relates to methods of preventing, modulating, reducing, treating and/or reversing of type 2 diabetes mellitus and/or auto-inflammatory disease, via administration of a therapeutically effective amount of a CD40-binding peptide that inhibits, influences, disrupts, blocks, and/or changes the interaction of CD40 and CD154 are disclosed.

BACKGROUND

Autoimmune diseases are conditions arising from an abnormal immune response to a normal body part. More than 80 diseases occur because of the immune system attacking the body's own organs, tissues, and cells. Type 1 diabetes, rheumatoid arthritis, systemic lupus erythematosus, and inflammatory bowel disease are common autoimmune diseases that affect a wide range of people across entire populations. Significantly, the autoimmune disorders mentioned above afflict substantial number of people affecting their daily lives and routines and require significant monetary and healthcare resources, time and care from healthcare providers.

According to the World Health Organization (WHO), an estimated 17.7 million people died from cardiovascular diseases (CVDs) in 2015, which represented 31% of all global deaths. CVDs, may also be known as heart and blood vessel disease, and includes numerous problems, many of which are related to a process called atherosclerosis. Moreover, according to the Healthcare Cost and Utilization Project (HCUP) which is sponsored by the Agency for Healthcare Research and Quality (AHRQ), in 2011, coronary atherosclerosis alone accounted for more than $10.4 billion in hospital costs. Accordingly, in 2011, coronary atherosclerosis alone was one of the ten most expensive conditions for inpatient hospitalizations in the United States.

Cardiovascular Disease and Atherosclerosis

Atherosclerosis is defined by arterial plaque formation that may lead to heart attack and stroke. Arterial plaque formation is caused by the deposition of cells, substances, waste products, and cellular debris including, but not limited to: cholesterol, dead cells, dendritic cells, foam cells, macrophages, mast cells, monocytes, smooth muscle cells. T-cells, collagen, calcium, and fibrin. Inflammatory changes within the arterial wall and plaque may play a crucial and causative role in atherosclerotic disease development. Consequently, the concept of atherosclerosis as an autoimmune and inflammatory disease has been investigated; however, a therapeutic control has not been established. The importance of controlling inflammation is highlighted by current clinical trials targeting other aspects of autoimmune, inflammation, and cardiovascular disease and death.

For example, CIRT (Cardiovascular Inflammation Reduction Trial) is attempting to use methotrexate to target interleukin-6 (IL-6) to test whether methotrexate will reduce rates of myocardial infarction, stroke, and cardiovascular death among patients with coronary artery disease patients with type 2 diabetes. Another example includes. CANTOS (Canakinumab Anti-inflammatory Thrombosis Outcomes Study) which is studying whether canakinumab can block the pro-inflammatory cytokine interleukin-1$\beta$ (IL-1$\beta$) to reduce rates of recurrent myocardial infarction, stroke, and cardiovascular death rates in heart attack patients who remain at a high risk. This risk is demarcated by elevated levels of the inflammatory biomarker high sensitivity C-reactive protein (hsCRP). These studies acknowledge that inflammation plays a critical role in atherothrombosis and atherosclerosis; however, these studies also recognize that is unknown whether inhibition of inflammation per se will lower vascular event rates.

Mammalian and human atherosclerotic lesions are characterized as a chronic inflammatory-fibroproliferative disease of the blood vessel wall containing monocytes, macrophages, endothelial cells, smooth muscle cells, platelets, and T-cells. Each of these cell types can express either or both of the CD40/CD154 costimulatory pair. This dyad is responsible for enhancing the immune response and may contribute to many chronic inflammatory diseases including rheumatoid arthritis, multiple sclerosis, and type 1 diabetes (T1D). However, no viable therapy exists for this highly atherogenic dyad.

Inflammation may occur when inflammatory cells, such as neutrophils, eosinophils, basophils, mast cells, macrophages, platelets, and endothelial cells, respond to inflammatory events or harmful stimuli, such as, invading microorganisms, damages cells, or other irritants. The body's inflammatory response is beneficial because for example, in the case of invading microorganisms, the inflammatory response is an important step in localizing the infecting agent for removal by the immune system. However, in autoimmunity there is no infection, yet severe inflammation is present or persistent. The inflammation in this case, referred to as aseptic chronic inflammation (ACI), is detrimental since it destroys normal tissues. The results of this aseptic inflammation are life-altering and in some cases life-threatening. Moreover, as with acute inflammation, this process is mediated by immune cells, including T-cells.

A major concern for modern medicine is how to control ACI such as that which occurs during autoimmune diseases, as well as how to control acute inflammation resulting from trauma. Inflammation, both chronic and acute, leads to tissue degeneration and eventual loss of function of major organs. ACI is not limited to a single disease, but is instrumental in numerous autoimmune diseases, including, but not limited to: type 1 diabetes (T1D), multiple sclerosis (MS), systemic lupus erythematosus (SLE), rheumatoid arthritis (RA), Crohn's disease, inflammatory bowel disease (IBS), chronic obstructive pulmonary disease (COPD) including types of autoimmune asthma, atherosclerosis, vasculitis, hypertension, thyroiditis including Hashimoto's and Graves diseases, primary biliary cirrhosis, Paget's disease, Addison's disease, acute respiratory distress syndrome (ARDS), acute lung injury, and aseptic chronic inflammation (ACI) associated with organ transplantation.

Autoimmune disorders are classified into two types: organ-specific (directed mainly at one organ) and non-organ-specific (widely spread throughout the body). Examples of organ-specific autoimmune disorders are insulin-dependent Type 1 diabetes (T1D) which affects the pancreas; Hashimoto's thyroiditis and Graves' disease, which affect the thyroid gland; pernicious anemia, which affects the blood; Addison's disease, which affects the adrenal glands; chronic active hepatitis, which affects the liver; myasthenia gravis which affects the muscle; and multiple sclerosis (MS), which affects tissue of the nervous system. An example of a non-organ-specific autoimmune disorders is rheumatoid arthritis (RA). Autoimmune diseases are often chronic, debilitating, and life-threatening. The National Institutes of Health (NIH) estimates that up to 23.5 million Americans suffer from autoimmune disease and that the prevalence is rising. It has been estimated that autoimmune diseases are among the ten leading causes of death among women in all age groups up to 65 years.

Acute inflammation, as observed during trauma or sepsis, is also immune cell mediated. While a comprehensive, complete, and exhaustive list of the molecular mediators in this process have not yet been identified, a prominent role for T-cells, lymphocytes, neutrophils, macrophages, monocytes, neutrophils, eosinophils, basophils, mast cells, and other inflammatory cells is strongly implicated. Therefore, a process to modulate these cell types may control the inflammatory response.

Type 2 Diabetes

The CD40-CD154 dyad constitutes a major inflammatory pathway (Schonbeck U, et al. *Cell Mol. Life Sci.* (2001) 58(1):4-43) that plays a significant role in type 1 diabetes (Waid D M. et al. *Clin. Inmunol.* (2007) 124(2):138-148). Type 2 diabetes (T2D) has historically and scientifically been primarily categorized as a metabolic disorder, however, type 2 diabetes is in the process of being redefined as an autoimmune disease rather than just a metabolic disorder (Winer, D, et al. *Nature Medicine* (2011) 17:610-617).

According to the United States Centers for Disease Control National Diabetes Statistics Report for 2017 (available at https://www.cdc.gov/diabetes/pdfs/data/statistics/national-diabetes-statistics-report.pdf), an estimated 30.3 million people of all ages—or 9.4% of the U.S. population had diabetes in 2015. An estimated 23 million people—or 7.2% of the U.S. population had been diagnosed with diabetes mellitus, and about 95% of those diagnosed with diabetes have type 2 diabetes. Based on fasting plasma glucose levels, one third to one half of cases of type 2 diabetes are undiagnosed and untreated (Harris M I, *Diabetes Care.* (1998) 21 [Suppl. 3: C11-C14]; Howard B V, et al., *Circulation.* 2002; 105:e132-e137; Grundy S M, et al., *Circulation.* 1999; 100: 1134-1146).

Although type 2 diabetes most often develops in people over the age of 45, type 2 diabetes increased 21% in American youth from 2001 to 2009 and a large study called SEARCH for Diabetes in Youth found that newly diagnosed cases of Type 2 diabetes in children and teens increased by about 4.8 percent in each year of the study's period between 2002 and 2012 ("Rates of new diagnosed cases of type 1 and type 2 diabetes on the rise among children, teens" National Institutes of Health. Apr. 13, 2017, available at https://www.nih.gov/news-events/news-releases/rates-new-diagnosed-cases-type-1-type-2-diabetes-rise-among-children-teens).

Major comorbidities complicate diabetes, the most common being cardiovascular disease (70.4 per 1,000 persons) including those with ischemic heart disease and stroke. Overall, for the year 2012, the American Diabetes Association estimates that the total direct and indirect estimated cost in the United States was $245 billion, including $176 billion in direct medical costs and $69 billion in reduced productivity (Yang, W. American Diabetes Association, 2013, Diabetes Care, 36 (4): 1033-46).

Both type 1 and type 2 diabetes are powerful and independent risk factors for coronary artery disease (CAD), stroke, and peripheral arterial disease (Schwartz C J. et al. *Diabetes Care.* (1992) 15:1156-1167; Stamler, J. et al. *Diabetes Care.* (1993) 16:434-444; Beckman J A. et al., Diabetes and atherosclerosis: epidemiology, pathophysiology, and management. *JAMA* (2002) 287:2570-2581). Atherothrombosis accounts for 65% to 80% of all deaths among North American patients with diabetes, compared with about 33% of all deaths in the general North American population (American Diabetes Association. *Diabetes Care.* (1993) 16:72-78). Therefore, a therapeutic regimen that is effective and can be tolerated for long periods of time would be beneficial to individuals and from a public health perspective. An ideal anti-diabetic agent may be an agent which corrects hyperglycemia, prevents macrovascular complications, and corrects the pathophysiological disturbances responsible for Type 2 Diabetes ("T2D"). Insulin resistance is basic to T2D, but β-cell failure eventually occurs with imbalance between insulin resistance and insulin secretion being a further complication. Therefore, therapeutically beneficial treatment approaches may aim to reverse insulin resistance and improve β-cell function.

T2D often conincides with obesity however genetic and environmental factors recently have been described as disease contributors (Comuzzie A G, *Best Pract. Res. Clin. Endocrinol. Metab.* (2002) 16(4):611-21. PubMed PMID: 12468410; van Tilberg J., et al. *J. Med. Genet.* (2001) 38(9):569-78. Pub Med PMID: 11546824; PMCID: PMC 1734947). Moreover, additional research has emerged that indicates that T2D, like T1D, has prominent inflammation component that is a contributing and/or driving factor of the T2D disease commencement, development and progression. The CD40-CD154 inflammatory dyad may act as a molecular driver to propel autoimmune inflammation and influence excessive levels of the dyad may be an unappreciated but contributing factor to T2D. (Hseih C J, et al., *Cir. J.* (2009) 73(5) 948-54; Kutlu M. et al., *Clin. Invest. Med.* (2009) 32(6): E244; Santilli F, et al., *J. Am. Coll. Cardiol.* (2006) 47(2):391-7; Santini. E. et al. *J. Endocrinol Invest.* 2008; 31(7):660-5; Varo N, et al., *Circulation.* 2003; 107(21): 2664-9).

Generally, inflammation may occur when inflammatory cells, such as neutrophils, eosinophils, basophils, mast cells, macrophages, platelets, endothelial cells, and lymphocytes, including but not limited to T cells and B cells respond to inflammatory events or harmful stimuli, such as, invading microorganisms, damaged cells, or other irritants. The body's inflammatory response is beneficial because, for example, in the case of invading microorganisms, the inflammatory response is an important step in localizing the infecting agent for removal by the immune system. However, in autoimmunity there is no infection, yet severe inflammation is present or persistent. The inflammation in this case, referred to as aseptic chronic inflammation (ACI), is detrimental since it destroys normal tissues. The results of this aseptic inflammation are life-altering and in some cases life-threatening. Moreover, as with acute inflammation, this process is mediated by immune cells, including T-cells.

A major concern for modern medicine is how to control ACI such as that which occurs during autoimmune diseases, as well as how to control acute inflammation resulting from trauma. Inflammation, both chronic and acute, leads to tissue degeneration and eventual loss of function of major organs. ACI is not limited to a single disease, but is instrumental in numerous autoimmune diseases, including, but not limited to: type 1 diabetes (T1D), multiple sclerosis, systemic lupus erythematosus, rheumatoid arthritis, Crohn's disease, inflammatory bowel disease, chronic obstructive pulmonary disease including types of autoimmune asthma, atherosclerosis, vasculitis, hypertension, thyroiditis including Hashimoto's and Graves diseases, primary biliary cirrhosis, Paget's disease. Addison's disease, acute respiratory distress syndrome, acute lung injury, and ACI associated with organ transplantation.

Autoimmune disorders are classified into two types: organ-specific (directed mainly at one organ) and non-organ-specific (widely spread throughout the body). Examples of organ-specific autoimmune disorders are insulin-dependent Type 1 diabetes (T1D) which affects the pancreas; Hashimoto's thyroiditis and Graves' disease, which affect the thyroid gland; pernicious anemia, which affects the blood; Addison's disease, which affects the adrenal glands; chronic active hepatitis, which affects the liver; myasthenia gravis which affects the receptors at the junction between nerves and muscles; and multiple sclerosis, which affects tissue of the nervous system. An example of a non-organ-specific autoimmune disorders is rheumatoid arthritis. Autoimmune diseases are often chronic, debilitating, and life-threatening. The National Institutes of Health (NIH) estimates that up to 23.5 million Americans suffer from autoimmune disease and that the prevalence is rising. It has been estimated that autoimmune diseases are among the ten leading causes of death among women in all age groups up to 65 years.

Acute inflammation, as observed during trauma or sepsis, is also immune cell mediated. While a comprehensive, complete, and exhaustive list of the molecular mediators in this process have not yet been identified, a prominent role for T-cells, lymphocytes, neutrophils, macrophages, monocytes, neutrophils, eosinophils, basophils, mast cells, and other inflammatory cells is strongly implicated. Therefore, a process to modulate these cell types may control the inflammatory response.

A unique T cell subset has been shown to be instrumental in the development of autoimmune disease. These cells are phenotypically characterized as CD4loCD40+ (Waid. D. M., et al., *Eur. J. of Inmunol.*, 34:1488, 2004; Vaitaitis, G. M., et al., *Cutting Edge, J. Immunol.*, 170:3455, 2003; Wagner. D. H., Jr., et al., *Proc. Nat'l. Acad. Sci.* USA, 99:3782, 2002: Wagner. D. H., Jr., et al., Int'l J. of *Mol. Med.* 4:231, 1999), and are referred to as Th40 cells. (Waid, D. M., et al. (2004) *Eur. J. of Immunol.* 34:1488; Vaitaitis. G. M., et al., *Cutting Edge, J. Immunol.* 170:3455, 2003; Wagner. D. H., Jr., et al., *Proc. Nat'l Acad. Sci.* USA 99:3782, 2002; Wagner. D. H., Jr., et al., *Int'l J. of Mol. Med.* 4:231, 1999). CD40 expression typically is associated with antigen presenting cells and the majority of prior art describes CD40 as being expressed on B cells, macrophages, monocytes, and other cells; however, CD40 proteins are also expressed on T cells (Waid. D. M., et al., 2004. *Eur. J. of Immunol.*, 34:1488, 2004; Vaitaitis, G. M., et al., *Cutting Edge, J. Inmunol.*, 170:3455, 2003; Wagner, D. H., Jr., et al., *Proc. Nat'l Acad. Sci.* USA, 99:3782, 2002; Wagner, D. H., et al., *Int'l. J. of Mol. Med.*, 4:231, 1999; Bourgeois, C., et al., *Science.* 297:2060, 2002; Fanslow, W. C., et al., *J. of Immun.*, 152:4262, 1994; Ramsdell, F., et al., *J. of Immunol.* 152:2190, 1994; Grabstein. K. H., et al., *J. of Inmunol.*, 150:3141, 1993; Armitage. R. J., et al., *Sem. in Immun.*, 5:401, 1993; Cooper, C. J., et al., *J of Immunol.*, 173:6532, 2004). While Th40 cells comprise a proportion of the peripheral CD4+ compartment in naïve, non-autoimmune mice (Waid. D. M., et al., *Eur. J. of Immunol.*, 34:1488, 2004; Wagner, D. H., Jr., et al., *Int'l J. of Mol. Med.*, 4:231, 1999), and in humans (Waid. D. M., et al., *Clin. Immunol.*, 124:138, 2007), this proportion is drastically expanded to as much as 50% of the CD4+ compartment in autoimmune prone mice (Waid, D. M., et al., *Eur. J. of Immunol.* 34:1488, 2004; Wagner, D. H., Jr., et al., *Proc. Nat'l Acad. Sci.* USA 99:3782, 2002; Wagner. D. H., et al., *Int'l J. of Mol. Med.*, 4:231, 1999) and humans (Waid, D. M., et al., *Eur. J. of Immunol.* 34:1488, 2004; Waid. D. M., et al., *Clin. Immunol.* 124:138, 2007; Waid. D. M., et al., *Clin. Inmunol.* 124:138, 2007). These T cells do not express early activation markers and occur in the naïve phenotype of non-challenged mice.

In NOD (non-obese diabetic) mice. Th40 cells occur at exaggerated levels in spleen, lymph nodes and the pancreas, even prior to diabetes onset (Waid. D. M., et al., *Eur. J. of Immunol.* 34:1488, 2004; Wagner, D. H., Jr., et al., *Proc. Nat'l Acad. Sci.* USA 99:3782, 2002). An elevated number and percentage of these T cells are seen in peripheral blood of type 1 diabetic (T1D) patients when compared to non-autoimmune controls and type 2 diabetic patients (Waid. D. M., et al., *Clin. Immunol.*, 124:138, 2007).

The observed increase in Th40 cells could mean that those T cells are antigen responsive or that CD40 expression is activation induced. Furthermore, several diabetogenic T cell clones are CD40+(Wagner. D. H., Jr., et al., *Proc. Nat'l Acad. Sci.* USA 99:3782, 2002). Purified primary Th40 cells from NOD mice and from pre-diabetic NOD (12-weeks of age) mice successfully transfer type 1 diabetes to NOD/scid (Non-Obese Diabetic/Severe Combined Immunodeficiency) recipient mice, directly demonstrating pathogenicity of the Th40 T cell subset (Waid. D. M., et al., *Eur. J. of Immunol.* 34:1488, 2004; Wagner, D. H., Jr., et al., 2002. *Proc. Nat'l Acad. Sci.* USA. 99:3782, 2002). It has been shown that Th40 cells infiltrate islet beta cells destroying insulin production thus suggesting islet antigen specificity (Waid. D. M., et al., *Eur. J. of Immunol.* 34:1488, 2004; Wagner. D. H., Jr., et al., *Proc. Nat'l Acad. Sci.* USA 99:3782, 2002). It has also been shown that Th40 cells are required for diabetes transfer. Peripheral (spleen and regional lymph node) T cells that were CD40 depleted, then CD25. Treg, depleted were not capable of transferring diabetes to Scid (Severe Combined Immunodeficiency) recipients. Even though Treg cells were removed, if the auto-aggressive CD40+ T cells subset is absent, disease transfer does not occur.

While Th40 cells are important in the development of autoimmunity, another important factor is expression of the CD40-Ligand, CD154. CD154 is temporally induced on activated T-cells in response to CD3/TCR stimulation (Lederman, S. et al., *J. of Exp. Med.*, 175:1091, 1992). CD154 expression has also been demonstrated on platelets, monocytes, basophils, cosinophils, dendritic cells, fibroblasts, smooth muscle, and endothelial cells (Russo, S. et al., *J. Immunol.* 171:5489, 2003; Stumpf. C., et al., *Eur. J. Heart*

Fail., 5:629, 2003; Schonbeck, U., et al., *Cell Mol. Life Sci.* 58:4, 2001). CD154 is a member of the tumor necrosis factor (TNF) super-family and a soluble form of CD154 (sCD154) has been described (Russo. S., et al., *J. Immunol.* 171:5489 2003; Stumpf, C., et al., *Eur. J. Heart Fail* 5:629, 2003; Toubi, E., et al., *Autoimmunity* 37:457, 2004). Therefore, sCD154 may act like a cytokine (Stumpf, C., et al., *Eur. J. Heart Fail.* 5:629, 2003). Even though CD154 has not been genetically linked in T1D studies, sCD154 is significantly elevated in T1D and may play a role in the disease process (Varo, N. et al., *Circulation* 107:2664, 2003; Cipollone. F. et al., *Diabetologia* 48:1216.2005; Devaraj. S., et al., *Diabetes* 55:774, 2006). The importance of CD40-CD154 interaction in autoimmunity has been established (Wagner. D. H., Jr., et al., *Proc. Nat'l Acad. Sci.* USA 99:3782, 2002; Kobata, T., et al., *Rev. Immunogenet.* 2:74, 2000; Homann, D., et al., *Immunity* 16:403, 2002; Goodnow, C. C., et al., *Lancet* 357:2115, 2001; Balasa, B., et al., *J. of Immunol.* 159:4620, 1997). Blocking CD40-CD154 interaction may prevent collagen induced arthritis. (Durie, F. H., et al., *Science* 281: 1328, 1993) experimental autoimmune encephalitis (Howard, L. M., et al., *Autoimmunity* 37:411, 2004), prostatitis (Grossman, M. E., et al., *J. Innmunother.* 24:237, 2001), and type-1 diabetes in the NOD mouse model (Durie. F. H. et al., *Science* 281:1328, 1993; Balasa, B. et al., *Journal of Immunology* 159:4620, 1997; Howard, L. M., et al., *Autoimmunity* 37:411, 2004; Grossman, M. E. et al., *J. Immunother.* 24:237, 2001). In the diabetes model, it was essential to administer a CD154 blocking antibody to NOD mice at 3-weeks of age because at 9-weeks, blocking antibodies had no effect on diabetes prevention (Balasa, B. et al., *J. of Immunol.* 159:4620, 1997).

Previous work has also demonstrated that the Th40 cell subset induces RAG1 and RAG2 (Recombination-Activating Genes) transcription, translation and nuclear translocation (Vaitaitis. G. M., et al., *Cutting Edge, J. Immunol.* 170:3455, 2003) when CD40 is engaged (Vaitaitis, G. M. et al., *Cutting Edge, J. Inmunol.* 170:3455, 2003). CD3 engagement does not induce RAG1 or RAG2 in T-cells (Vaitaitis, G. M., et al., *Cutting Edge, J. Immunol.* 170:3455, 2003). Subsequent to RAG1/RAG2 induction, CD40-mediated T-cell receptor (TCR) revision occurs in peripheral T cells (Vaitaitis, G. M. et al., *Cutting Edge, J. Inmunol.* 170:3455, 2003). CD40 induction of TCR revision is RAG dependent. T cells isolated from a TCR-Tg mouse undergo TCR revision when CD40 engaged, but T-cells from the TCR-Tg.RAG–/– mouse do not TCR revise when CD40 engaged (Wagner, D. H., Jr. et al., *Int'l J. of Mol. Med.* 4:231, 1999).

CD40 is a 50-kDa integral membrane protein of the tumor necrosis factor receptor (TNF-R) family. It is constitutively expressed as a homotrimer (Foy T M, et al., *Ann. Rev. of Immunol.*, 14:591, 1996). In general, stimulation of all CD40-expressing cell types induces operations which contribute to inflammation, such as enhancement of costimulatory and adhesion molecules, and up-regulation of proteolytic enzymes (Mach, F. et al., *Atherosclerosis.* 137 Suppl: S89-95, 1998).

CD40's ligand-CD154—is a 39-kDa protein that belongs to the tumor necrosis factor (TNF) family. CD40 forms a trimer that binds CD154 at the interface of the three monomers. CD154 is expressed commonly on cells beyond the surface-expressed CD154, as CD154 may also exist in a soluble biologically active form (sCD154) that is shed from the cell surface after activation. The main source of sCD154 is platelets. (Foy T M. et al., *Ann. Rev. of Immunol.*, 14:591, 1996).

Genetically manipulated mouse models are utilized for research and development concerning atherosclerosis and cardiovascular disease because wild type mice are generally highly resistant to development and progression of atherosclerosis. Prior studies have attempted to block the CD40/CD154 interaction by using monoclonal antibodies and this approach has proven efficacious in several mouse model studies utilizing the Apoe–/– or LDLr deficient atherosclerotic models. Additionally, these same mouse models built with a deletion of CD154 saw significant reductions in overall plaque formation and may have also contributed to production of a more stable plaque phenotype. Clinically, stable plaques are identifiable and denoted by increased collagen and smooth muscle content, a thick fibrous cap, and an observable decrease in T cell, macrophage, and lipid accumulation.

Genetically manipulated mouse models are utilized for research and development concerning T2D because mouse models can portray insulin resistance and the inability of the beta cell to sufficiently compensate, which are characteristic of T2D in humans. Many animal models, including mouse models for T2D are obese, reflecting the human condition where obesity is closely linked to T2D development.

Multiple treatment options have been put forward to address and control both chronic and acute inflammation. Many approaches use non-steroidal anti-inflammatory drugs (NSAIDS) that attack the production of leukotrienes and prostaglandins, cellular products that cause localized inflammation. Other approaches use more powerful immunosuppressant drugs such as cyclophosphamide, methotrexate and azathioprine that suppress the immune response and stop the progression of the disease. Still other treatments involve the use of monoclonal antibodies (mAb) designed to alter the immune responses to self-tissues, as occurs during autoimmune diseases. However, all of these treatments often have severe, long-term side effects.

Current immune-modulatory therapies may rely upon monoclonal antibody treatments that may give rise to complications. For example, antibodies administered to a subject may cross-react with unintended targets and cause severe nephritic complications and those that specifically act against CD154 may cause embolic complications. Further, the CD40-CD154 interaction may play an important role in antibody generation which may indicate that administration of a monoclonal antibody could induce auto-antibody generation and further complications, which may inhibit the restoration of normal immune function (see generally Banchereau, J. et al., *Annu. Rev. of Immunol.* 12:881, 1994).

Other studies have demonstrated that blocking the CD154 interaction by using monoclonal antibodies, or limiting the CD40 receptor by monoclonal antibodies may abrogate atherosclerosis, and may confer a more favorable plaque phenotype characterized by lower inflammation and higher fibrosis. These studies additionally demonstrated that neointimal formation and restenosis may be limited by blocking the CD154 interaction. Studies concerning lupus nephritis may have demonstrated that blocking CD40 mediated signals can reduce anti-double-stranded DNA (anti-dsDNA) antibodies. Moreover, these studies may demonstrate that the reduction of anti-dsDNA was associated with increased serum complement levels and reduced glomerular inflammation, which may be viewed positively from a clinical perspective. However, the use of monoclonal antibodies to target the CD40/CD154 dyad was abandoned due to thromboembolic events which may have been related to the functioning of CD154 in thrombus stabilization. It is postulated that CD154 stabilize thrombi by interaction with the integrin $\alpha_{IIb}\beta_3$, and by inhibiting CD154, thrombi may be less stable, and as a consequence shed emboli causing thrombotic events.

Studies of small molecules have also been conducted to attempt to inhibit the important CD40-CD154 costimulatory interaction required for T cell activation and the development of an effective immune response. For example, suramin, a symmetric polysulfonated napthylamine-benzamide urea derivative was studied for its ability to inhibit CD154 binding to its receptor and prevented the CD154-induced proliferation of human B cells; however, its numerous reversible toxicities (lethargy, rash, fatigue, anemia, hyperglycemia, hypocalcemia, coagulapathies, neutropenia, renal and hepatic complications) (Kaur, M. et al. (2002) *Invest. New Drugs* 20(2):209-19), loss of activity in protein-rich medium, and its interference with positive costimulatory interaction (Margolles-Clark, E. et al. (2009) *Biochem. Pharmacol.* 77(7):1236-45) made this and other related small-molecule candidates unlikely sources for effective therapy for the CD40-CD154 dyad.

Uncertainty exists regarding the primary lesion and the relative importance of the different tissues, metabolic defects in the liver and the peripheral tissues such as fat, muscle, and pancreatic β-cells likely all contribute to type 2 diabetes. Furthermore, although the cause of T2D is incompletely understood, complex and confounded by both genetic and environmental influences, hyperglycemia itself is believed to hinder pancreatic beta-cell function (Cernea, S., et al. *Biochem. Med.* (Zagreb) 2013; 23(3):266-80).

Accordingly, type 2 diabetes in humans typically develops through a progressive series of increasingly disruptive phases or stages. Initially, pre-diabetes is characterized by impaired glucose tolerance, wherein the body has difficulty clearing glucose after a meal (postprandial hyperglycemia) and/or the body may have decreased sensitivity to insulin. In a second phase or stage, postprandial hyperglycemia and basal hyperglycemia occur while insulin producing beta cells of the pancreas become dysfunctional at an increasing rate. During the next phase of the disease progression, hyperglycemia occurs even after fasting and at a cellular level significant beta cell atrophy takes place. Ultimately, in the final phase or end stage of disease progression, beta cells can no longer produce and/or release insulin and the patient requires insulin replacement therapy.

T2D is clinically characterized by hyperglycemia and pathologically by insulin resistance with relative insulin secretory impairment. Individuals who are genetically prone to developing T2D may experience insulin resistance (the earliest detectable metabolic defect) between 15 and 25 years or more before the clinical onset of overt diabetes. (Kahn, C R, Diabetes. (1994) 43:1066-1084). T2D classically has been associated with age and obesity; however, the increased diagnosis of youth with T2D has demonstrated that these two factors alone are not the sole reliable predictors of the disease. Body mass index (BMI) is also clearly associated with T2D, but both genetic and environmental factors are now identified as contributory as well (Wu Y, et al. *Int. J. Med. Sci.* (2014) 11(11):1185-200. Epub 2014/09/06; Cefalu. W T, Diabetes. (2009) 58(2):307-8; Donath, M Y. et al., *Nat. Rev. Immunol.* (2011) 11(2):98-107). Obesity creates inflammatory conditions, and sustained inflammation resulting from obesity or other conditions may be important in T2D development (Donath, M Y, et al., *Nat. Rev. Immunol.* (2011) 11(2):98-107; Donath, M Y, Nat. *Rev. Drug Discov.* (2014) 13(6):465-76).

Thus, there exists a need in the art for safer and more effective methods for treatment and prevention of T2D implicated by the autoimmune and inflammatory pathway and dyad related to CD40-CD154. The present developments may address this need by describing methods for treatment of T2D by administration of a therapeutically effective amount of CD40-binding peptide.

Thus, there exists a need in the art for safer and more effective methods for treatment and prevention of cardiovascular diseases (CVDs) and T2D implicated by aseptic chronic inflammation (ACI). The present developments may address this need by describing methods for treatment of atherosclerosis by administration of a therapeutically effective amount of a peptide that affects, regulates, blocks, inhibits, or modulates the CD40-CD154 dyad. Further, the present developments may provide the added benefit of preventing auto-antibody generation, and thus allow the resumption of normal immune function.

This statement of background is for information purposes only and is not intended to be a complete or exhaustive explication of all potentially relevant background.

SUMMARY

The present developments may provide novel methods for preventing, modulating, and/or reducing atherosclerosis that arises in a corporeal body. Atherosclerosis may arise as a result of chronic inflammatory response of white blood cells in the walls of arteries. It is postulated that the chronic inflammatory response and the subsequent buildups of plaque in arteries may be caused by elevated levels of cholesterol and triglycerides in the blood, high blood pressure, and cigarette smoking.

The present developments are based on the knowledge that interaction of CD40-ligand (CD154 protein) with CD40 protein expressed on T-cells (Th40 cells), may be important in the development of atherosclerosis and autoimmune disease. The present developments may be based on the elucidation of the critical residues in CD40 and CD154 that may be important for this interaction. The present developments relate to blocking the interaction between a CD40 protein and a CD154 protein through the use of small peptides that interact with the CD40 protein at a site where the CD154 protein would normally bind. The present developments also relate to using such peptides to reduce the level of Th40 cells, thereby reducing the severity of disease.

One embodiment of the present developments is a method for preventing atherosclerosis comprising contacting the CD40 protein with a peptide that interacts with the CD40 protein. Preferred peptides may be those that are less than 25 amino acids in length, and that bind to a CD40 protein, thereby inhibiting its interaction with a CD154 protein; however, the length of the peptide should not be considered a limitation on the developments herein as there are numerous other factors that may affect the ability of the peptide to perform its intended and desired result.

One embodiment of the present developments is a method for preventing, modulating, and/or reducing atherosclerosis, the method comprising inhibiting interaction between a CD40 protein and a CD154 protein with a peptide that interacts with the CD40 protein. Preferred peptides interact with the CD40 protein at the CD154-binding site. Preferably such peptides are less than 25 amino acids in length. Even more preferred peptides are those amino acid sequences selected from SEQ ID NOs 3-9 and 25-30.

One embodiment of the present developments is a method for preventing, modulating, and/or reducing atherosclerosis, the method comprising administering to a subject in need thereof, a therapeutically effective amount of a peptide that affects the interaction of CD40 with CD154/CD40-ligand. An aspect of this development may be that the peptide binds to CD40. In this embodiment, the peptide may bind to a CD40 protein with a Kd of greater than $10^{-6}$. Further, in this embodiment, the peptide may affect the interaction between CD40 and CD154. Additionally, a preferred embodiment may inhibit the binding of CD40 to CD154. Moreover, in this embodiment, the peptide binds to CD40 at the site where CD40 interacts with CD154. In this embodiment, the peptide affects the interaction of CD40 with CD154 in such a manner as to prevent the expansion of Th40 cells. In this embodiment, the peptide affects the interaction of CD40 with CD154 in such a manner as to reduce the number of Th40 cells. In this embodiment, the peptide affects the interaction of CD40 with CD154 in such a manner as to alter the cytokine expression profile of a cell population, treated with said peptide.

One embodiment of the present developments is a method to modulate and/or reduce atherosclerosis in an animal, the method comprising administering to the animal, a peptide that interacts with a CD40 protein in such a manner as to modulate IFNγ (interferon gamma). Preferred peptides are those that interact with the CD40 protein at the CD154-binding site, thereby modulating IFNγ. Preferred peptides modulate inflammation by reducing the level of Th40 cells to no more than 25% of the total T-cell population. Such methods can be used to prevent and/or reduce atherosclerosis and symptoms that may accompany cardiovascular diseases, more generally.

One embodiment of the present developments is a method to identify a patient at risk for developing cardiovascular disease and/or atherosclerosis, the method comprising obtaining a sample containing T-cells from a patient to be tested, contacting the sample with a peptide that binds the CD40 protein, detecting the CD-40 bound peptide, and determining the level of Th40 cells from the amount of CD40 bound, wherein a level of Th40 cells greater than 25% of the total T-cell population indicates the patient is at risk for developing cardiovascular disease and/or developing atherosclerosis.

Yet, another embodiment of the present developments is a method to prevent, modulate, or reduce calcium buildup, or calcification of vessel walls, the method comprising administering to the subject in need thereof, a therapeutically effective amount of a peptide which specifically binds to a CD40 presenting cells at the CD154 binding site.

Another embodiment of the present developments, is a method to administer a CD40-binding peptide to prevent, modulate, and/or reduce atherosclerosis, comprising selecting a peptide that interacts with a CD40 protein and CD154 binding site, selecting a delivery method selected from the group comprising intramuscular (IM) delivery, intravenous (IV) delivery, subcutaneous (SC) delivery, oral delivery, gavage delivery, emollient/skin delivery, or transdermal patch.

Another embodiment of the present developments, is a method to administer a CD40-binding peptide to prevent, modulate, and/or reduce atherosclerosis in an animal, comprising selecting a peptide that interacts with a CD40 protein and CD154 binding site, using an extended delivery method selected from the group comprising an implantable device, a hydrophilic polymer formulation, a permeable polymeric membrane, injectable gel implants, solvent extraction system, phase inversion system, thermosensitive gels, pH dependent in situ gels, microparticles, microspheres, nanoparticles, nanospheres, bio-degradable implants, or photoactivated depot.

Another embodiment of the present developments, is a method to lower LDL cholesterol in a subject, the method comprising administering to the subject in need thereof, a therapeutically effective amount of a peptide which specifically binds to a CD40 presenting cells at the CD154 binding site.

The present developments may provide novel methods for preventing, modulating, reducing, treating and/or reversing T2D that arises in a corporeal body. Moreover, the developments disclosed herein are therapeutic methods which may additionally be used for the prevention, control, and treatment of diseases, disorders, and conditions, in particular immune and inflammatory diseases.

The present developments are based on the knowledge that interaction of CD40-ligand (CD154 protein) with CD40 protein expressed on T-cells (Th40 cells), may be important in the development of type 2 diabetes and autoimmune diseases. The present developments may be based on the elucidation of the critical residues in CD40 and CD154 that may be important for this interaction. The present developments relate to blocking and/or disrupting the interaction between a CD40 protein and a CD154 protein through the use of small synthesized peptides that interact and/or associate with the CD40 protein at a site where the CD154 protein would normally bind. The present developments also relate to using such peptides to reduce the level of Th40 cells, thereby reducing the severity of disease. The peptides of the current developments may bind directly and/or alternatively associate with the CD40 molecule in such a way as to alter CD40 function.

In autoimmune diseases and conditions, CD40 engagement may promote inflammation. Accordingly, in one embodiment of the present developments the peptide may alter CD40 signals to no longer be inflammatory. Thus, in one embodiment the peptides of the current development may block, disrupt, interfere, and/or inhibit CD40 function at sites including but not limited to Th40 cells, pancreas beta cells, endothelial cells, B cells, monocytes, and/or macrophages. The current developments contemplate the use of the small interfering peptides (SIPs) disclosed herein to interfere with the CD40-signaling pathway of any cells that may present with CD40. These peptides may be able to interfere at specific sites depending on the route of administration.

One embodiment of the present developments is a method for preventing, modulating, reducing, and/or reversing type 2 diabetes comprising contacting the CD40 protein with a peptide that interacts with the CD40 protein. Preferred peptides are those that are less than 25 amino acids in length, and that bind to a CD40 protein, thereby inhibiting its interaction with a CD154 protein.

One embodiment of the present developments is a method for preventing, modulating, reducing and/or reversing type 2 diabetes, the method comprising inhibiting interaction between a CD40 protein and a CD154 protein with a peptide that interacts with the CD40 protein. Preferred peptides interact with the CD40 protein at the CD154-binding site. Preferably such peptides are less than 25 amino acids in length. Even more preferred peptides are those amino acid sequences selected from SEQ ID NOs 3-9 and 25-30.

In one aspect the present development provides a method for modulating and/or increasing glucose transport protein 4 (GLUT4) the method comprising administering to a patient a therapeutically sufficient dose of a peptide selected from SEQ ID NOs 3-9 and 25-30.

One embodiment of the present developments is a method to prevent, modulate, reduce and/or reverse type 2 diabetes in an animal, the method comprising administering to the animal, a peptide that interacts with a CD40 protein in such a manner as to modulate glucose transport protein 4 ("GLUT4"). Preferred peptides are those that interact with the CD40 protein at the CD154-binding site, thereby modulating GLUT4. Preferred peptides may modulate, upregulate, or increase GLUT4 in both adipose and muscle tissue compared to untreated populations. Such methods can be used to prevent and/or reduce T2D and symptoms that may accompany T2D and autoimmune related inflammation, more generally.

Another embodiment of the present developments, is a method to administer a CD40-binding peptide to prevent, modulate, reduce and/or reverse type 2 diabetes, comprising selecting a peptide that interacts with a CD40 protein and CD154 binding site, selecting a delivery method selected from the group comprising intramuscular (IM) delivery, intravenous (IV) delivery, subcutaneous (SC) delivery, oral delivery, gavage delivery, emollient/skin delivery, transdermal patch, or nasal administration.

Another embodiment of the present developments, is a method to administer a CD40-binding peptide to prevent, modulate, reduce and/or reverse type 2 diabetes in an animal, comprising selecting a peptide that interacts with a CD40 protein and CD154 binding site, using an extended delivery method selected from the group comprising an implantable device, a hydrophilic polymer formulation, a permeable polymeric membrane, injectable gel implants, solvent extraction system, phase inversion system, thermosensitive gels, pH dependent in situ gels, microparticles, microspheres, nanoparticles, nanospheres, bio-degradable implants, or photoactivated depot.

Another embodiment of the present developments, is a method of modulating, controlling, and/or increasing GLUT4 in a subject, the method comprising administering to the subject in need thereof, a therapeutically effective amount of a peptide selected from SEQ ID NOs 3-9 and 25-30.

Another embodiment of the present developments, is a method to modulate, affect and/or reduce interleukin-2 signaling in a cell or a subject comprising administering a peptide selected from SEQ ID NOs 3-9 and 25-30, in an amount sufficient to reduce or inhibit interleukin-2 signaling, wherein, the interleukin-2 signaling is associated with a condition selected from the group comprising type I diabetes, multiple sclerosis, systemic lupus erythematosa, rheumatoid arthritis, Crohn's disease, inflammatory bowel disease, chronic obstructive pulmonary disease, asthma, atherosclerosis, vasculitis, hypertension, thyroiditis, primary biliary cirrhosis. Paget's disease, Addison's disease, acute respiratory distress syndrome, acute lung injury, and/or aseptic chronic inflammation, more generally.

Another embodiment of the present developments, is a method to modulate and/or reduce interleukin-2 signaling in a cell or a subject comprising administering a peptide selected from SEQ ID NOs 3-9 and 25-30 in an amount sufficient to reduce or inhibit interleukin-2 signaling, wherein, the interleukin-2 signaling is associated with type 2 diabetes.

Another embodiment of the present developments is a method to modulate and/or reduce IFN-γ in a cell or a subject comprising administering a peptide selected from SEQ ID NOs 3-9 and 25-30, in an amount sufficient to reduce or inhibit IFN-γ signaling, wherein, the IFN-γ signaling is associated with type 2 diabetes.

Another embodiment of the present developments, is a method to modulate, affect, and/or induce changes of interleukin-21 (IL-21), interleukin-22 (IL-22), IFNγ, TNFα, interleukin-6 (IL-6), granulocyte-macrophage colongy-stimulating factor (GM-CSF), interleukin-4 (IL-4), interleukin-10 (IL-10) and transforming growth factor beta (TGFβ) in a cell or subject comprising administering a peptide selected from SEQ ID NOs 3-9 and 25-30, in an amount sufficient to change said interleukin-21 (IL-21), interleukin-22 (IL-22), IFNγ, TNFα, interleukin-6 (IL-6), granulocyte-macrophage colongy-stimulating factor (GM-CSF), interleukin-4 (IL-4), interleukin-10 (IL-10) and transforming growth factor beta (TGFβ), wherein the said interleukin-21 (IL-21), interleukin-22 (IL-22), IFNγ, TNFα, interleukin-6 (IL-6), granulocyte-macrophage colongy-stimulating factor (GM-CSF), interleukin-4 (IL-4), interleukin-10 (IL-10) and transforming growth factor beta (TGFβ) signaling is associated with a condition selected from group comprising type I diabetes, multiple sclerosis, systemic lupus erythematosa, rheumatoid arthritis. Crohn's disease, inflammatory bowel disease, chronic obstructive pulmonary disease, asthma, atherosclerosis, vasculitis, hypertension, thyroiditis, primary biliary cirrhosis. Paget's disease, Addison's disease, acute respiratory distress syndrome, acute lung injury, type 2 diabetes, and/or aseptic chronic inflammation, more generally.

Another embodiment of the present developments includes a method to modulate and/or reduce interleukin 17 (IL-17) in a cell or a subject comprising administering a peptide selected from SEQ ID NOs 3-9 and 25-30 in an amount sufficient to reduce or inhibit interleukin 17 (IL-17) signaling, wherein, the IL-17 signaling is associated with a condition selected from the group comprising type I diabetes, multiple sclerosis, systemic lupus erythematosa, rheumatoid arthritis, Crohn's disease, inflammatory bowel disease, chronic obstructive pulmonary disease, asthma, atherosclerosis, vasculitis, hypertension, thyroiditis, primary biliary cirrhosis. Paget's disease, Addison's disease, acute respiratory distress syndrome, acute lung injury, and/or aseptic chronic inflammation, more generally.

Another embodiment of the present developments includes a method to modulate and/or reduce interleukin 17 (IL-17) in a cell or a subject comprising administering a peptide selected from SEQ ID NOs 3-9 and 25-30 in an amount sufficient to reduce or inhibit interleukin 17 (IL-17) signaling, wherein, the IL-17 is associated with type 2 diabetes.

One embodiment of the present developments is a method to identify a patient at risk for developing type 2 diabetes, the method comprising obtaining a sample containing T-cells from a patient to be tested, contacting the sample with a peptide that binds the CD40 protein, detecting the CD-40 bound peptide, and determining the level of Th40 cells from the amount of CD40 bound, wherein a level of Th40 cells greater than 25% of the total T-cell population indicates the patient is at risk for developing type 2 diabetes.

One embodiment of the present developments is the composition of matter of small interfering peptides of those in SEQ ID NOs: 4, 27, 28, 29, and 30. These embodiments of the current developments may be used for the for the treatment of disease selected from the group comprising type I diabetes, multiple sclerosis, systemic lupus erythematosa, rheumatoid arthritis, Crohn's disease, inflammatory bowel disease, chronic obstructive pulmonary disease, asthma, atherosclerosis, vasculitis, hypertension, thyroiditis, primary biliary cirrhosis, Paget's disease, Addison's disease, acute respiratory distress syndrome, acute lung injury, type 2 diabetes, and/or aseptic chronic inflammation, more generally.

BRIEF DESCRIPTION OF THE FIGURES

FIG. 24 is a table of blood clot data from human blood in the presence of 15-mer peptide compared to normal clotting.

FIG. 25A is a table providing the relative peptide stability assessed by ExPASy analysis.

FIG. 25B is a table providing the relative peptides stability assessed by ExPASy analysis.

FIG. 26 is a western blot comparing control and treated samples from subject mice.

FIG. 31 is a graph of plaque composition for KGYY6 (SEQ ID NO:29) treated and control subject mice.

FIG. 32A is an image of trichrome stained sections of KGYY6 (SEQ ID NO:29) treated subject.

FIG. 32B is an image of trichrome stained sections of control subjects.

DETAILED DESCRIPTION

Figure 1:
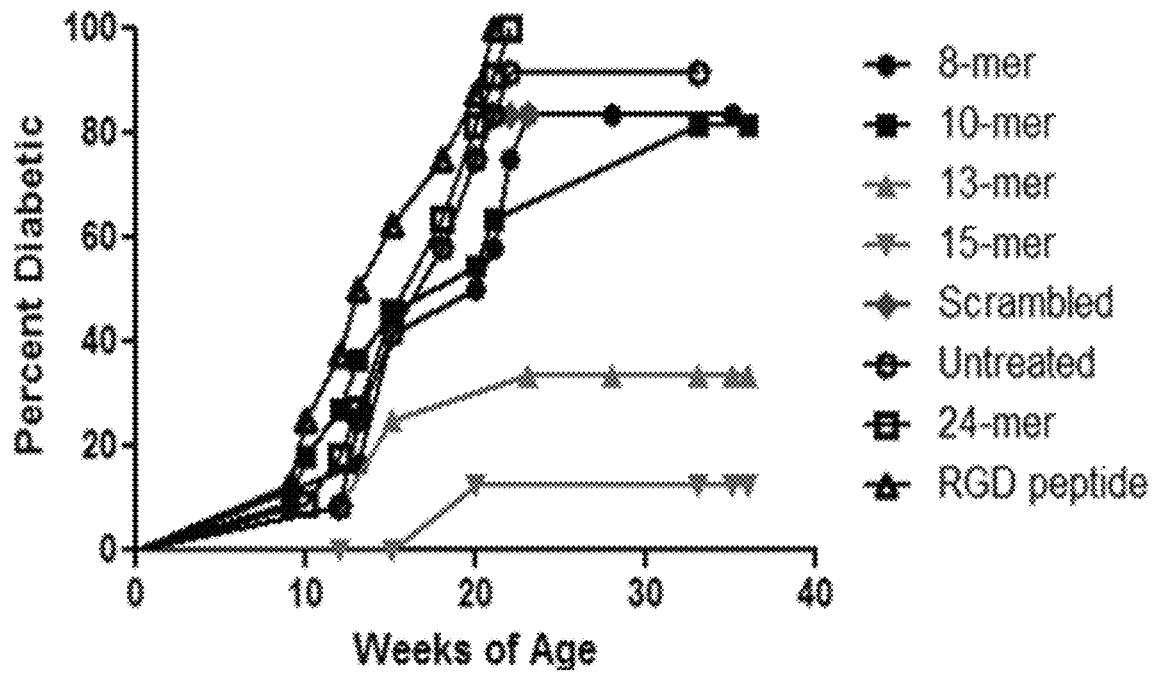
FIG. 1 is a chart of the effect of various peptides of CD154 on the development of diabetes in NOD mice. The 8-mer (SEQ ID NO: 5), 10-mer (SEQ NO: 24), 13-mer (SEQ ID NO:25), 15-mer (SEQ ID NO: 7), and 24-mer (SEQ ID NO:26) were tested.

The present subject matter is based on the discovery that a unique subset of T-cells, which express CD40 protein, and thus are referred to as Th40 cells, may be instrumental in autoimmune inflammation. Moreover, involvement of Th40 cells in the autoimmune process may be dependent on the interaction between CD40 protein expressed on the surface of the T-cell, and CD154 protein. Interaction of CD40 and CD154 results in activation signals being delivered between the cells, and subsequent activation of the Th40 cell. Such activation results in propagation of the Th40 cell and an increase in inflammation (e.g., an increase in the number of immune cells and immunoregulatory molecules, present in the system). Accordingly, inhibition of the CD40/CD154 interaction can modulate Th40 cell activity, and thereby affect inflammation. Thus the present subject matter relates to the peptides, and administration thereof, that may affect the interaction between a CD40 protein and a CD154 protein, thereby modulating inflammation. Moreover, the present subject matter relates to peptides that affect the interaction between CD40 protein expressed on the surface of a T-cell, and a CD154 protein, thereby affecting T-cell activity, controlling inflammation, and consequently preventing, modulating, and reducing atherosclerosis. The present subject matter also encompasses the use of such peptides to detect Th40 cells.

Before the present development is further described, it is to be understood that this invention is not strictly limited to particular embodiments described, as such may of course vary. It is also to be understood that the terminology used herein is for the purpose of describing particular embodiments only, and is not intended to be limiting, since the scope of the present invention will be limited only by the claims.

It must be noted that as used herein and in the appended claims, the singular forms "a," "an," and "the" include plural referents unless the context clearly dictates otherwise. It should further be understood that as used herein, the term "a" entity or "an" entity refers to one or more of that entity. For example, a nucleic acid molecule refers to one or more nucleic acid molecules. As such, the terms "a", "an", "one or more" and "at least one" can be used interchangeably. Similarly, the terms "comprising", "including" and "having" can be used interchangeably.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates, which may need to be independently confirmed.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments are specifically embraced by the present invention and are disclosed herein just as if each and every combination was individually and explicitly disclosed. In addition, all sub-combinations are also specifically embraced by the present invention and are disclosed herein just as if each and every such sub-combination was individually and explicitly disclosed herein.

It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Furthermore, as used herein the term animal refers to a vertebrate, preferably a mammal, more preferably a human. Suitable mammals on which to use the methods of the present invention include but are not limited farm animals, sports animals, pets, primates, mice, rats, horses, dogs, cats, and humans. The term animal can be used interchangeably with the terms subject or patient.

One embodiment of the present subject matter is a peptide that interacts with a CD40 protein in such a manner as to prevent atherosclerosis. As used herein, the terms interact, interaction, and the like, mean that two molecules come into sufficient physical proximity such that they cause a modulation of inflammation. One such type of interaction is a binding interaction. In such an interaction the peptide associates with CD40 to form a complex. An example of complex formation is the association of an antigen with an antibody. According to the present subject matter, binding of a peptide hereof to a CD40 protein can be reversible (e.g., non-covalent binding interactions) or non-reversible (e.g., covalent binding interactions). Moreover, a reversible interaction can be strong or weak, the strength of the interaction being determined by the forces (e.g., ionic charges, hydrogen binding, van der Walls interactions, etc.) exerted by each protein on the other protein in the complex. Factors affecting the strength of an interaction between two molecules are known to those skilled in the art. One useful measure of the strength of binding between two molecules, such as a peptide and a protein, is the dissociation constant (Kd). Preferred peptides of the present invention are those that bind to a CD40 protein with a Kd of no more than about $1 \times 10^{-6}$ M, about $1 \times 10^{-7}$ M, or about $1 \times 10^{-8}$ M. Particularly preferred peptides are those having a Kd of less than about $1 \times 10^{-6}$ M. In one embodiment, a peptide hereof binds to a CD40 protein with a Kd of less than 100 nM, less than 50 nM, less than 25 nM, less than 10 nM, less than 5 nM, less than 3 nM, less than 2 nM, or less than 1 nM. Methods of measuring and analyzing binding interactions between a peptide and a CD40 protein are known by those of skill in the art.

As used herein, the change the level of Th40 cells present in an animal, or in a culture of T cells may be indicative of modulation of inflammation. As used herein, the terms level, number, count and concentration can be used interchangeably. Modulation of inflammation may mean an increase or decrease in the number of Th40 cells present in the inflammatory environment; however, the modulation of inflammation should not be limited to cell numbers or counts. Consequently, modulation can be referred to as positive or negative. Positive modulation (also referred to as up-regulation) of inflammation may result in an increase in the number of Th40 cells in the inflammatory environment. Negative modulation (also referred to as down-regulation) of inflammation may result in a reduction in the number of Th40 cells present in the inflammatory environment. The level, count, or concentration of Th40 cells may not be indicative of inflammation in the inflammatory environment. A preferred peptide may be one that down-regulates inflammation, thereby reducing the number of Th40 cells present in the inflammatory environment. Positive and negative modulation of inflammation may or may not result in a change in the type and amount of immunoregulatory molecules present in the inflammatory environment. In some instances, it is possible that the Th40 levels will not change but the activity of those cells is altered such that they are no longer exerting or increasing inflammatory cytokines and other biomarkers of inflammation. Therefore, as used herein modulating inflammation may refer to changes in the Th40 levels, numbers, or concentration in an corporeal body or sample, and may also refer to changes in inflammation more generally that may be associated with disease, inflammatory cytokines, and/or cell derived inflammatory mediator molecules.

It will be appreciated by those skilled in the art that both a cell culture system and the immune system of an animal comprise basal levels of immune cells and immunoregulatory molecules. The phrases basal level and normal level can be used interchangeably. With regard to the immune system of an animal, as used herein, the basal level of a type of immune cell (e.g., Th40 cell), or a immunoregulatory molecule, refers to the average number of that cell type, or immunoregulatory molecule, present in a population of individuals considered healthy (i.e., free of metabolic, autoimmune, or infectious disease). With regard to a cell culture system, as used herein, the basal level of a type of immune cell, or an immunoregulatory molecule, refers to the average level of that cell type, or immunoregulatory molecule, present in a population of cells that is non-activated. Those skilled in the art are capable of determining if a T-cell, or a population of such cells, is activated. For example, the expression of CD69, CD25 and/or CD154 proteins by a cell indicates that the cell has been activated.

The basal level of a cell or molecule can be a specific amount (e.g., a specific concentration) or it can encompass a range of amounts. Basal levels, or ranges, of immune cells and immunoregulatory molecules are known to those in the art. For example, in a healthy individual, the normal level of CD4+ T-cells present in human blood is 500-1500 cells/ml. Variability in this measurement can result from differences in the method used to determine the cell count. Furthermore, normal levels of cells can also be reported as a percentage of a total cell population. For example, in a healthy individual, Th40 cells make up less than 25% of the total T cell population. Thus, as used herein, the term inflammation refers to an inflammatory environment in which Th40 cells make up greater than about 25%, greater than about 30%, greater than about 35%, greater than about 40%, greater than about 45%, greater than about 50%, greater than about 55%, greater than about 60%, greater than about 65%, greater than about 70%, greater than about 75%, or greater than about 80% of the total T-cell population. Moreover, a preferred peptide herein is one that reduces the level of Th40 cells to less than about 50%, less than about 45%, less than about 40%, less than about 35%, less than about 30%, less than about 27%, or equal to about 25% of the total T-cell population. Methods of measuring different types of T-cells in the T-cell population are known to those skilled in the art. Furthermore, a novel method for detecting Th40 cells using peptides hereof is disclosed herein.

As used herein, the phrase inflammatory environment refers to the overall population of immune cells, and related immunoregulatory molecules, that are present in a culture of cells, or in the body of an animal. As such, the phrase inflammatory environment encompasses the types, and/or the relative amounts of immune cells and immunoregulatory molecules (e.g., cytokines) present in a culture of cells, or in an animal, which are involved in affecting an inflammatory reaction. Examples of cells encompassed by the term inflammatory environment include, but are not limited to, T cells, neutrophils, macrophages, granulocytes, and the like. The inflammatory environment relates to cells and molecules that mediate both acute and chronic inflammation. It will be appreciated by those skilled in the art that the inflammatory environment refers to the system to which peptides hereof are administered. In one embodiment, the system is a cell culture system. In one embodiment, the system is a whole animal.

A preferred peptide hereof is one that selectively interacts with a CD40 protein in solution, as determined using an assay such as an immunosorbent assay, or on the surface of a T-cell. As used herein, the terms selectively, selective, specific, and the like, indicate the peptide has a greater affinity for a CD40 protein than it does for proteins unrelated to the CD40 protein. More specifically, the terms selectively, selective, specific, and the like indicate that the affinity of the peptide for CD40 is statistically significantly higher than its affinity for a negative control (e.g., an unrelated protein such as albumin) as measured using a standard assay (e.g., ELISA). Suitable techniques for assaying the ability of a peptide to selectively interact with a CD40 protein are known to those skilled in the art. Such assays can be in vitro or in vivo assays. Examples of useful assays include, but are not limited to, an enzyme-linked immunoassay, a competitive enzyme-linked immunoassay, a radioimmunoassay, a fluorescence immunoassay, a chemiluminescent assay, a lateral flow assay, a flow-through assay, an agglutination assay, a particulate-based assay (e.g., using particulates such as, but not limited to, magnetic particles or plastic polymers, such as latex or polystyrene heads), an immunoprecipitation assay, an immunoblot assay (e.g., a western blot), a phosphorescence assay, a flow-through assay, a chromatography assay, a polyacrylamide gel electrophoresis (PAGE)-based assay, a surface plasmon resonance assay, a spectrophotometric assay, a particulate-based assay, an electronic sensory assay and a flow cytometric assay. Methods of performing such assays are well known to those skilled in the art. In one embodiment, an assay can be performed using cells in culture, or it can be performed in a whole animal. Assays can be designed to give qualitative, quantitative or semi-quantitative results, depending on how they are used and the type of result that is desired.

Cardiovascular Disease (CVD), Atherosclerosis, and Cholesterol Related Developments One embodiment hereof is a peptide that interacts with a CD40 protein in such a manner as to affect the interaction of the CD40 protein with a CD154 protein, thereby modulating inflammation. The effect of the peptide on the CD40/CD154 interaction can be positive or it can be negative. For example, the peptide can interact with the CD40 protein in such a manner that the strength of the interaction between the CD40 protein and a CD154 protein is increased. Alternatively, the peptide can interact with the CD40 protein such that the strength of the interaction between the CD40 protein and a CD154 protein is decreased. Methods of measuring the strength of binding between the peptide and a CD40 protein are known to those skilled in the art. A preferred peptide hereof is one that reduces the strength of the interaction between a CD40 protein and a CD154 protein. Preferred peptides hereof reduce the strength of binding between a CD40 protein and a CD154 protein by at least 10%, at least 20%, at least 30%, at least 40%, at least 50%, at least 60%, at least 70%, at least 80%, at least 90%, or at least 95%. A particularly preferred peptide is one that completely inhibits binding of CD40 to CD154. Complete inhibition of binding between CD40 and CD154 means that when a peptide hereof is brought into proximity with a CD40 protein and a CD154 protein under conditions that would normally allow the interaction of CD40 and CD154, no such interaction occurs and activation signals are not stimulated in the CD40-expressing cell. Consequently CD40/CD154 mediated modulation of inflammation does not occur. In one embodiment, the peptide interacts with the CD40 protein in such a manner as to reduce the level of inflammation in the system. In one embodiment, the peptide interacts with the CD40 protein in such a manner as to inhibit the development of inflammation in the system.

While peptides hereof can interact with any site on the CD40 protein, preferred peptides interact with the CD40 protein at a location that overlaps with the CD154 binding site. In one embodiment, a peptide hereof interacts with the CD40 protein at the CD154 binding site. An example of such a peptide is a CD40 ligand competitive antagonist. As used herein, peptides that interfere with, or inhibit, the binding of a CD154 protein to a CD40 protein are referred to as small interfering peptides (SIPs). As used herein a small interfering peptide is a peptide that, through physio-chemical properties, interferes with the interaction of a CD40 protein with a CD154 protein, thereby preventing activation signals from being delivered to the CD40-bearing cell, thus limiting the activation of the CD40-bearing cell, and consequently, inflammation. As demonstrated herein, the consequences of such interference are prevention of T-cell activation and propagation, and a prevention or reduction of inflammation. As demonstrated herein, in some instances the results of such inhibition or prevention of interaction between CD40 and CD154 may include observable data that demonstrates that atherosclerosis, and characteristics of diseases associated therewith, are prevented, modulated, and/or reduced.

Additionally, a small interfering peptide, may, through its physio-chemical properties, interfere with the interaction of a CD40 protein with a CD154 protein, thereby preventing activation signals from being delivered to the CD40-bearing cell, thus limiting the activation of the CD40-bearing cell, and consequently, modulating, inhibiting, and preventing atherosclerosis. As demonstrated herein, the consequences of such interference are prevention of T cell activation and propagation, and a prevention, reduction, or modulation of atherosclerotic developments.

A peptide useful for practicing methods of the present developments should be of a size sufficient to interact with CD40 protein in such a manner as to modulate atherosclerosis. It is understood by those skilled in the art that preferred peptides are relatively short since they are easier and less expensive to produce. Preferred peptides may be those that are less than 25 amino acids in length; however, the length of the peptide may be longer than 25 amino acids in some instances. A preferred peptide may be one that is 4, 6, 8, 10, 13, 15, or 24 amino acids in length. In one embodiment, the peptide is an amino acid selected from the group of SEQ ID NO:3 (Core-sequence see Table 1). SEQ ID NO:4 (6-mer see Table 1). SEQ ID NO:5 (8-mer mouse see Table 1). SEQ ID NO:6 (8-mer human see Table 1), SEQ IN NO:7 (15-mer see Table 1). SEQ ID NO:8 (15-mer human see Table 1), SEQ ID NO:9 (24-mer see Table 1), SEQ ID NO: 24 (10-mer see Table 1), SEQ ID NO: 25 (13-mer see Table 1), SEQ ID NO: 26 (24-mer see Table 1), SEQ ID NO: 27 (6-mer (Form 2) see Table 1), SEQ ID NO: 28 (6-mer (Form 3) see Table 1). SEQ ID NO: 29 (6-mer (Form 4) see Table 1), SEQ ID NO: 30 (6-mer (Form 4) see Table 1) and SEQ ID NO:32 (24-mer-mouse (Form 2)). The sequences of such peptides are shown below in Table 1.

TABLE 1

| SEQ ID NO | SEQUENCE | Description |
|---|---|---|
| 1 | MIETYSQPSP RSVATGLPAS MKIFMYLLTV FLITQMIGSV LFAVYLHRRL DKVEEEVNLH EDFVFIKKLK RCNKGEGSLS LLNCEEMRRQ FEDLVKDITL NKEEKKENSF EMQRGDEDPQ IAAHVVSEAN SNAASVLQWA KKGYYTMKSN LVMLENGKQL TVKREGLYYV YTQVTFCSNR EPSSQRPFIV GLWLKPSSGS ERILLKAANT HSSSQLCEQQ SVHLGGVFEL QAGASVFVNV TEASQVIHRV GESSEGLLKL | SwissPro 27548.2 Mouse CD40 Ligand (CD154 Protein) |
| 2 | MIETYNQTSP RSAATGLPIS MKIFMYLLTV FLITQMIGSA LFAVYLHRRL DKIEDERNLH EDFVFMKTIQ RCNTGERSLS LLNCEEIKSQ FEGFVKDTML NKFEETKKNS FEMQKGDQNP QIAAHVISEA SSKITSVLOW AEKGYYTMSN NLVTLENGKQ LTVKRQGLYY IYAQVTFCSN REASSQAPFI ASLCLKSPGR FERILLRAAN THSSAKPCGQ QSIHLGGVFE LQPGASVFVN VTDPSQVSHG TGFTSFGLLK L | SwissPro 29965 Human CDC) Ligand (CD154 Protein) |
| 3 | KGYY | Core-sequence |
| 4 | KKGYYT | 6-mer |
| 5 | AKKGYYTM | 8-mer-mouse |
| 6 | AEKGYYTM | 8-mer human |
| 7 | VLQWAKKGYYTMKSN | 15-mer-mouse |
| 8 | VLQWAEKGYYTMSNN | 15-mer human |
| 9 | NAASVLQWAKKGYYTMKSNLVMLE | 24-mer |
| 10 | ISQAVHAAHAEINEAGR | 15-mer from ovalbumin; control peptide |
| 11 | G-L-Q-W-A-K-K-G-Y-Y-T-M-K-S-N | Gly-1 |
| 12 | V-G-Q-W-A-K-K-G-Y-Y-T-M-K-S-N | Gly-2 |
| 13 | V-L-G-W-A-K-K-G-Y-Y-T-M-K-S-N | Gly-3 |
| 14 | V-L-Q-G-A-K-K-G-Y-Y-T-M-K-S-N | Gly-4 |
| 15 | V-L-Q-W-G-K-K-G-Y-Y-T-M-K-S-N | Gly-5 |
| 16 | V-L-Q-W-A-G-K-G-Y-Y-T-M-K-S-N | Gly-6 |
| 17 | V-L-Q-W-A-K-G-G-Y-Y-T-M-K-S-N | Gly-7 |
| 18 | V-L-Q-W-A-K-K-G-G-Y-T-M-K-S-N | Gly-8 |
| 19 | V-L-Q-W-A-K-K-G-Y-G-T-M-K-S-N | Gly-9 |

TABLE 1-continued

| SEQ ID NO | SEQUENCE | Description |
|---|---|---|
| 20 | V-L-Q-W-A-K-K-G-Y-Y-G-M-K-S-N | Gly-10 |
| 21 | V-L-Q-W-A-K-K-G-Y-Y-T-G-K-S-N | Gly-11 |
| 22 | ISQAVHAAHAEINEAGR | 15-mer from ovalbumin; control peptide |
| 23 | YVQGKANLKSKLMYT | Scrambled peptide |
| 24 | WAKKGYYTMK | 10-mer mouse |
| 25 | VLQWAKKGYYTMK | 13-mer mouse |
| 26 | AASVLQW AKKGYYTMKSNLVVLEN | 24-mer mouse |
| 27 | KGYYTM | 6-mer (Form 2) |
| 28 | AEKGYY | 6-mer (Form 3) |
| 29 | AKKGYY | 6-mer (Form 4) |
| 30 | AKGYYT | 6-mer (Form 5) |
| 31 | YKNVKQMAYWLTGKS | Scrambled peptide |
| 32 | AASVLQWAKKGYYTMKSNLVMLEN | 24-mer-mouse (Form 2) |

Interaction of a CD40 protein and a CD154 protein has been shown to occur at particular regions within each protein. The inventors have now shown that, surprisingly, a peptide comprising only a short portion of the CD154 region that interacts with CD40 is capable of binding to a CD40 protein, thereby modulating atherosclerosis. Thus one embodiment hereof is a peptide that comprises at least a portion of the amino acid sequence of a CD154 protein such that the peptide interacts with CD40 protein in such a manner as to modulate atherosclerosis. In one embodiment, interaction of the peptide with CD40 protein results in negative modulation of atherosclerosis. In one aspect, the peptide comprises at least a portion of SEQ ID NO:1 or SEQ ID NO:2.

In one aspect, the peptide is as short as possible yet comprises enough of the CD154 protein to allow interaction with a CD40 protein in such a manner as to modulate atherosclerosis. In one embodiment, a peptide hereof comprises 6, 13 or 15 contiguous amino acids from SEQ ID NO:1 or SEQ ID NO:2, and interacts with CD40 in such a manner as to modulate atherosclerosis. A preferred peptide comprises a core sequence of lysine-glycine-tyrosine-tyrosine (KGYY; SEQ ID NO:3), which corresponds to amino acids 142-145 of SEQ ID NO:1 and amino acids 143-146 of SEQ ID NO:2. Useful peptides can comprise additional regions of sequence from SEQ ID NO:1 or SEQ ID NO:2 that are adjacent to the core sequence, so long as the peptide is capable of modulating atherosclerosis. In one embodiment hereof, a peptide comprises at least one sequence selected from SEQ ID NO:3. SEQ ID NO:4, SEQ ID NO:7. SEQ ID NO:8, SEQID NO:9, SEQ ID NO:24. SEQ ID NO:25, SEQ ID NO:26, SEQ ID NO:27. SEQ ID NO:28, SEQ ID NO:29, SEQ ID NO:30, and SEQ ID NO:32, so long as the peptide interacts with CD40 protein in such a manner as to modulate atherosclerosis. In one embodiment of the present subject matter, a peptide hereof is a sequence selected from SEQ ID NO:3. SEQ ID NO:4. SEQ ID NO:5, SEQ ID NO:6, SEQ ID NO:7, SEQ ID NO:8. SEQID NO:9. SEQ ID NO:24, SEQ ID NO:25, SEQ ID NO:26. SEQ ID NO:27, SEQ ID NO:28. SEQ ID NO:29. SEQ ID NO:30, and SEQ ID NO:32. In one embodiment of the present subject matter, a peptide hereof is a sequence selected from SEQ ID NOs 3-9, 25-30, and 32.

While peptides of the present subject matter may be selected entirely of or from sequences that are responsible for the interaction of the peptide with a CD40 protein, they may additionally contain amino acid sequences that do not interact with a CD40 protein, but which have other useful functions. Any useful, additional amino acid sequence can be added to the CD40-interacting sequence, so long as the additional sequences do not have an unwanted effect on the ability of the CD40 interacting sequence to interact with a CD40 protein. For example, in addition to the amino acid sequence responsible for interacting with a CD40 protein, a peptide hereof can contain amino acid sequences that are useful for visualizing or purifying the peptide. Such sequences act as labels (e.g., enzymes) or tags (antibody binding sites). Examples of such labels and tags include, but are not limited to, B-galactosidase, luciferase, glutathione-s-transferase, thioredoxin. HIS-tags, biotin tags, and fluorescent tags. Other useful sequences for labeling and tagging proteins are known to those of skill in the art.

Likewise, peptides hereof can be modified, so long as such modification does not significantly affect the ability of the peptide to modulate atherosclerosis. Such modifications can be made, for example, to increase the stability, solubility or absorbability of the protein. Examples of such modifications include, but are not limited to pegylation, glycosylation and chemical modification of the peptide.

Peptides hereof may be obtained from nature (e.g., obtained from plants, animals or microorganisms) or they may be produced in a laboratory (e.g., recombinantly or synthetically). Preferred peptides are those that are synthesized. Also encompassed are peptides that are combinations of natural and synthetic molecules. General methods for producing and isolating recombinant or synthetic peptides are known to those skilled in the art. It should be noted that, as used herein, an isolated, or biologically pure, molecule, is one that has been removed from its natural milieu. As such the terms isolated, biologically pure, and the like, do not necessarily reflect the extent to which the protein has been purified.

As has been described herein, interaction of the CD40 protein and the CD154 protein are necessary for involvement of Th40 cells in atherosclerosis. Consequently, inhibition of the interaction between a CD40 and CD154 protein using peptides hereof is a useful method of affecting atherosclerosis. Thus one embodiment is a method to reduce the interaction between a CD40 protein and a CD154 protein comprising introducing into an environment containing a CD40 protein and a CD154 protein, a peptide, that interacts with the CD40 protein in such a manner as to reduce the interaction between the CD40 protein and the CD154 protein. In one aspect hereof, the peptide reduces the interaction between the CD40 protein and the CD154 protein by at least 5%, at least 10%, at least 20%, at least 30%, at least 40%, at least 50%, at least 60%, at least 70%, at least 80%, at least 90%, or at least 95%. In one embodiment, the peptide reduces the interaction between the CD40 protein and the CD154 protein by a factor of at least 10, at least 100, at least 1,000, at least 10,000. Methods of measuring the strength of the interaction between the CD40 protein and the CD154 protein have been discussed previously, and are also know to those of skill in the art.

One embodiment hereof is a method to modulate atherosclerosis comprising contacting a CD40 protein with a peptide that interacts to the CD40 protein in such a manner as to modulate inflammation. In one aspect, interaction of the peptide with the CD40 protein decreases the number of Th40 cells by at least 5%, at least 10%, at least 20%, at least 30%, at least 40%, at least 50%, at least 60%, at least 70%, at least 80%, at least 90%, or at least 95%. In one embodiment, interaction of the peptide with the CD40 protein decreases the number of Th40 cells by a factor of at least 10, at least 100, at least 1.000, at least 10,000.

One aspect of the current developments hereof is a method to modulate atherosclerosis, cardiovascular disease, and/or cholesterol levels comprising contacting a CD40 protein with a peptide that interacts with the CD40 protein in such a manner as to ameliorate inflammation. One aspect of this alternative embodiment is that the Th40 levels do not change in response to contacting said CD40 protein with a peptide that interacts with the CD40 protein. In one aspect, Th40 cells treated with peptide may stop, slow, reduce, or retard production of inflammatory cytokines. In this aspect the number of Th40 levels may remain relatively unchanged.

One aspect is a method to reduce atherosclerosis in a patient, the method comprising administering a peptide hereof to the patient. In one embodiment, the peptide comprises an amino acid sequence selected from SEQ ID NO:3, SEQ ID NO:4, SEQ ID NO: 7, SEQ ID NO:8, SEQ ID NO:9, SEQ ID NO:24. SEQ ID NO:25, SEQ ID NO:26, SEQ ID NO:27. SEQ ID NO:28, SEQ ID NO:29. SEQ ID NO:30, and SEQ ID NO:32. In one embodiment, the peptide is an amino acid sequence selected from SEQ ID NO:4. SEQ ID NO:8, SEQ ID NO:9. SEQ ID NO:24. SEQ ID NO:25, SEQ ID NO:26. SEQ ID NO:27, SEQ ID NO:28, SEQ ID NO:29. SEQ ID NO:30 and SEQ ID NO:32. In a preferred embodiment, interaction of the peptide with the CD40 protein decreases the number of Th40 cells by at least 5%, at least 10%, at least 20%, at least 30%, at least 40%, at least 50%, at least 60%, at least 70%, at least 80%, at least 90%, or at least 95%. In another embodiment, interaction of the peptide with the CD40 protein decreases the number of Th40 cells by a factor of at least 10, at least 100, at least 1,000, at least 10.000. In a preferred embodiment, the level of Th40 cells is reduced so that Th40 cells comprise no more than about 20%, about 25%, about 30%, about 35%, or about 40% of the total T-cell population.

Peptides and methods hereof are suitable for use in cell culture as well as for treating a patient. As used herein the term patient refers to any animal in need of such treatment. The animal can be a human or a non-human animal. A preferred animal to treat is a mammal. A peptide can be administered or applied per se, or as pharmaceutical compositions. A peptide hereof, or a pharmaceutical composition thereof, can be administered to a patient by a variety of routes, including, but limited to, by injection (e.g., intravenous, intramuscular, subcutaneous, intrathecal, intraperitoneal), by inhalation, by oral (e.g., in a pill, tablet, capsule, powder, syrup, solution, suspension, thin film, dispersion or emulsion), transdermal, transmucosal, pulmonary, buccal, intranasal, sublingual, intracerebral, intravaginal rectal or topical administration or by any other convenient method known to those of skill in the art.

The amount of a peptide hereof and/or a pharmaceutical composition thereof that will be effective can be determined by standard clinical techniques known in the art. Such an amount is dependent on, among other factors, the patient being treated, including, but not limited to the weight, age, and condition of the patient, the intended effect of the compound, the manner of administration and the judgment of the prescribing physician. Also, in this context, it should be noted that in treating a patient exhibiting a disorder of interest, a therapeutically effective amount of an agent or agents such as these is administered. A therapeutically effective dose refers to that amount of the compound that results in amelioration of one or more symptoms or a prolongation of survival in a patient.

A peptide hereof, or a pharmaceutical composition thereof, can be administered alone or in combination with one or more other pharmaceutical agents, including other compounds of the present disclosure. The specific pharmaceutical composition depends on the desired mode of administration, as is well known to the skilled artisan.

Because the developments have demonstrated that Th40 cells are intimately involved in the development of autoimmune diseases, atherosclerosis, and cardiovascular disease, the peptides and methods disclosed herein can be used to affect atherosclerosis resulting from such diseases. Thus, one embodiment hereof is a method to treat atherosclerotic disease in a patient in need of such treatment, the method comprising administering to a patient a peptide that interacts with the CD40 protein, thereby reducing atherosclerosis. In one embodiment the peptide interacts with the CD40 protein in such a manner as to affect the interaction of CD40 and CD154, thereby reducing atherosclerosis. In a preferred embodiment, interaction of the peptide with the CD40 protein reduces the number of Th40 cells in a patient to a level equal to that observed in subjects that do not have cardiovascular disease. The present developments are suitable for treating any patient having an autoimmune disease and/or cardiovascular disease, the development of which is dependent on Th40 cells. More specifically, peptides hereof are suitable for reducing the level of Th40 cells in such patients. In a preferred embodiment, a peptide hereof reduces the level of Th40 cells in a patient suffering from a cardiovascular disease to no more than about 25% of the total T-cell population. In another embodiment, a peptide hereof reduces inflammatory cytokine levels while having no effect on the Th40 levels in a patient.

One example of a disease that is particularly amenable to treatment using a peptide of the present developments may be atherosclerosis. In atherosclerosis, inflammatory changes of the arterial wall occur resulting in the formation and buildup of arterial plaque. Consequently, control of inflammatory cells and cell signaling via CD40-CD154 interaction may be able to be used to control, modulate, and/or reduce atherosclerotic lesions that are characterized as chronic inflammatory-fibroproliferative disease of the vessel wall. Several murine models of T2D and/or atherosclerosis have been developed. The progression of lesion formation is observable in Apolipoprotein E (ApoE) deficient transgenic mice and can be observed by measurement of the aortic arch, the number and type of plaque, and characterized in accordance with the American Heart Association's staging of atherosclerosis, ranging from AHA type I to AHA type V. AHA type 1, may be characterized by early or initial lesions, may be comprised of histologically "normal" cells, macrophage infiltration, and isolated foam cells. AHA type V, may be characterized by advanced or complicated legions, including but not limited to increased endothelial dysfunction characterized by surface defects, hematoma, hemorrhage, and/or thrombosis. Thus, one embodiment of the present developments is a method to prevent atherosclerosis in an individual at risk for developing atherosclerosis, the method comprising administering to the individual a peptide to selectively bind to a CD40 expressing cell.

Moreover, atherosclerosis may be particularly amenable to treatment using a peptide of the current development. The risk for atherosclerosis may result from familial factors (e.g., inheritance) or from other factors, such as the physical condition of the individual. The level of atherosclerotic activity and disease may vary from individual to individual depending on numerous factors such as level of activity, diet, smoking status, and other variable factors that are dynamic such as levels of inflammation. Some methods of risk assessment for atherosclerosis are known to those skilled in the art. Accordingly, in one embodiment of the present development, the method of treatment comprises administering to a patient in need thereof, a peptide that comprises an amino acid sequence selected from SEQ ID NO:3, SEQ ID NO:4, SEQ ID NO: 7, SEQ ID NO:8, and SEQ ID NO:9, so long as the peptide can down-regulate inflammation. In one embodiment, the peptide is an amino acid sequence selected from SEQ ID NO:3, SEQ ID NO:4, SEQ ID NO:5, SEQ ID NO:6, SEQ ID NO: 7. SEQ ID NO:8, SEQ ID NO:9. SEQ ID NO:24, SEQ ID NO:25, SEQ ID NO:26, SEQ ID NO:27, SEQ ID NO:28, SEQ ID NO:29, SEQ ID NO:30 and SEQ ID NO:32.

The developments herein also show that, surprisingly, peptides hereof can be used to reverse the disease process in individuals already showing signs of atherosclerosis. Thus, one aspect of the present subject matter is a method to reverse atherosclerosis comprising administering to a patient diagnosed as having atherosclerosis, a peptide hereof. In one embodiment, the peptide comprises an amino acid sequence selected from SEQ ID NO:3, SEQ ID NO:4. SEQ ID NO: 7. SEQ ID NO:8, and SEQ ID NO:9, so long as the peptide can down-regulate inflammation. In one embodiment, the peptide is an amino acid sequence selected from SEQ ID NO:3, SEQ ID NO:4. SEQ ID NO:7, SEQ ID NO:8, and SEQ ID NO:9. As used herein the phrase to reverse atherosclerosis means to reduce the aortic-arch infiltration, plaque, and lesions of an individual with atherosclerosis to a level comparable to that observably lower levels or in some instances to levels that may be more common in a non-atherosclerotic individual.

As has been described, peptides of the present invention selectively bind to a CD40 expressing cell. Consequently, peptides of the present subject matter can be used to identify Th40 cells. Thus one embodiment hereof is a method to detect Th40-dependent atherosclerosis, said method comprising contacting a T-cell population with a peptide hereof. In a preferred embodiment, the peptide is labeled with a detectable marker, such as, for example, luciferase or alkaline phosphatase. Such detection can be performed using assay techniques known to those skilled in the an. In general, an assay for detecting Th40 cells using a peptide hereof comprises (a) obtaining a sample of cells; (b) contacting a peptide hereof with said cells under condition suitable to allow binding of the peptide to Th40 cells, if present; (c) washing said cells using conditions that disrupt non-specific interactions, and that remove unbound peptide; and (d) detecting peptide bound to cells. Detection of bound peptide can be achieved directly or indirectly. For example, direct detection can be achieved using a peptide labeled using a detectable marker, as disclosed herein. Following the wash step listed above, the cells are then simply screened for the presence of detectable marker. The presence of detectable marker in the cell sample indicates the presence of Th40 cells, and thus Th40-dependent atherosclerosis. Alternatively, indirect detection involves the use of a second molecule, such as an antibody, that binds to the peptide. In an indirect detection assay, following the wash step listed above, a detection molecule that binds the peptide is added to the cell sample. The detection molecule is labeled with a detectable marker. After washing away unbound detection molecule, the cells are screened for the presence of detectable marker. The presence of detectable marker in the cell sample indicates the presence of Th40 cells. It should be understood that the assays described herein are meant as examples of useful assays, and other assay techniques can be employed. Suitable assay techniques are known to those skilled in the art, and are also disclosed in, for example, *Molecular Cloning: A Laboratory Manual*. Sambrook, J., Fritsch, E. F., and Maniatis, T, Cold Spring Harbor Laboratory Press; 2nd Edition (December 1989). All references cited herein are incorporated herein in their entirety.

The assay technology described above can also be used to identify other molecules that affect the interaction of a CD40 protein with a CD154 protein. Examples of such molecules include, but are not limited to, proteins, peptides and small molecules. For example, assays can be designed that test the ability of molecules to compete with a peptide of the present developments for binding to a Th40 cell. For instance, a peptide labeled with a detectable marker, can be mixed with a test molecule and a population of cells known to contain Th40 cells, under conditions that allow binding of the peptide to the Th40 cells. Following an appropriate incubation period, the cells are washed to remove unbound peptide, and the cells screened for the presence of detectable marker. Alternatively, the labeled peptide could be bound to Th40 cells first, and after a wash step to remove unbound peptide, the test molecule could be added to the cells containing bound peptide. Following an incubating period and a wash step to remove unbound molecule, or released peptide, the cells are screened for the presence of detectable marker. In either case, absence of the detectable marker in the cell sample indicates the test molecule is able to compete with the peptide for binding to the Th40 cells, while presence of the detectable marker would indicate the test molecule does not inhibit binding of the peptide to Th40 cells. Inhibition of binding need not be 100%, as such assay would also be useful for identifying molecules that partially inhibit binding of the peptide to Th40 cells. It is understood by those skilled in the art that such assays would involve the use of positive controls (e.g., unlabeled peptide) and negative controls (e.g., a protein/molecule that is known not to bind to Th40 cells).

Because increased levels of Th40 cells are associated with the development of autoimmune disease, the present developments can be used to identify patients at risk for developing autoimmune disease and autoimmune related atherosclerosis and/or cardiovascular disease more generally. Thus, one embodiment of the present developments is a method to identify a patient at risk for developing autoimmune related atherosclerosis. In one embodiment, patients at risk for developing atherosclerosis are identified by obtaining a sample from a patient to be tested, contacting the T-cell portion of said sample with a peptide hereof, and determining the level of Th40 cells present in the sample, wherein a level of Th40 cells greater than about 25% of the total T-cell population indicates the patient is at risk for developing atherosclerotic disease. In one embodiment, the peptide comprises an amino acid sequence selected from SEQ ID NO:3, SEQ ID NO:4. SEQ ID NO:8, SEQ ID NO:7. SEQ ID NO:9 SEQ ID NO:24, SEQ ID NO:25, SEQ ID NO:26, SEQ ID NO:27, SEQ ID NO:28. SEQ ID NO:29, SEQ ID NO:30, and SEQ ID NO:32 so long as the peptide binds to the CD40 protein. In one embodiment, the peptide is an amino acid sequence selected from SEQ ID NO:3, SEQ ID NO:4. SEQ ID NO:7, SEQ ID NO:8. SEQ ID NO:9, SEQ ID NO:24, SEQ ID NO:25. SEQ ID NO:26, SEQ ID NO:27, SEQ ID NO:28, SEQ ID NO:29. SEQ ID NO:30, and SEQ ID NO:32. In a preferred embodiment the peptide is labeled with a suitable detectable marker such as, for example, luciferase or alkaline phosphatase.

The present developments also comprise kits useful for practicing the methods disclosed herein, the kit comprising a peptide that interacts with a CD40 protein in such a manner as to modulate atherosclerosis. In one embodiment, the peptide comprises an amino acid sequence selected from SEQ ID NO:3, SEQ ID NO:4. SEQ ID NO:7, SEQ ID NO:8, and SEQ ID NO:9, so long as the peptide can down-regulate atherosclerosis. In one embodiment, the peptide is an amino acid sequence selected from SEQ ID NO:3, SEQ ID NO:4. SEQ ID NO:7, SEQ ID NO:8, and SEQ ID NO:9. Another embodiment is a kit for determining the level of Th40 cells, the kit comprising a peptide that interacts with a CD40 protein, and methods for detecting CD40-bound peptide. Kits can also contain associated reagents and components, such as, but not limited to, buffers, labels, containers, inserts, tubing, vials, syringes, and the like.

Type 2 Diabetes Related Developments

The present subject matter is based on the discovery that a unique subset of T-cells, which express CD40 protein, and thus are referred to as Th40 cells, that may be instrumental in autoimmune inflammation, including conditions such as type 2 diabetes. Moreover, involvement of Th40 cells in the autoimmune process may be dependent on the interaction between CD40 protein expressed on the surface of the T-cell, and CD154 protein. Interaction of CD40 and CD154 results in activation signals being delivered between the cells, and subsequent activation of the Th40 cell. Such activation results in propagation of the Th40 cell and an increase in inflammation (e.g., an increase in the number of immune cells and immunoregulatory molecules, present in the system). Accordingly, inhibition of the CD40/CD154 interaction can modulate Th40 cell activity, and thereby affect inflammation. Thus the present subject matter relates to the peptides, and administration thereof, that may affect the interaction between a CD40 protein and a CD154 protein, thereby modulating inflammation. Moreover, the present subject matter relates to peptides that affect the interaction between CD40 protein expressed on the surface of a T-cell, and a CD154 protein, thereby affecting T-cell activity, controlling inflammation, and consequently preventing, modulating, reducing and/or reversing type 2 diabetes. The present subject matter also encompasses the use of such peptides to detect Th40 cells.

One embodiment of the present subject matter is a peptide that interacts with a CD40 protein in such a manner as to prevent type 2 diabetes. As used herein, the terms interact, interaction, and the like, mean that two molecules come into sufficient physical proximity such that they cause a modulation of inflammation. One such type of interaction is a binding interaction. In such an interaction the peptide associates with CD40 to form a complex. An example of complex formation is the association of an antigen with an antibody. According to the present subject matter, binding of a peptide hereof to a CD40 protein can be reversible (e.g., non-covalent binding interactions) or non-reversible (e.g., covalent binding interactions). Moreover, a reversible interaction can be strong or weak, the strength of the interaction being determined by the forces (e.g., ionic charges, hydrogen binding, van der Walls interactions, etc.) exerted by each protein on the other protein in the complex. Factors affecting the strength of an interaction between two molecules are known to those skilled in the art. One useful measure of the strength of binding between two molecules, such as a peptide and a protein, is the dissociation constant (Kd). Preferred peptides of the present invention are those that bind to a CD40 protein with a Kd of no more than about $1\times10^{-6}$ M, about $1\times10^{-7}$ M, or about $1\times10^{-8}$ M. Particularly preferred peptides are those having a Kd of less than about $1\times10^{-9}$ M. In one embodiment, a peptide hereof binds to a CD40 protein with a Kd of less than 100 nM, less than 50 nM, less than 25 nM, less than 10 nM, less than 5 nM, less than 3 nM, less than 2 nM, or less than 1 nM. Methods of measuring and analyzing binding interactions between a peptide and a CD40 protein are known by those of skill in the art.

As used herein, the change the level of Th40 cells present in an animal, or in a culture of T cells may be indicative of modulation of inflammation. As used herein, the terms level, number, count and concentration can be used interchangeably. Modulation of inflammation may mean an increase or decrease in the number of Th40 cells present in the inflammatory environment; however, the modulation of inflammation should not be limited to cell numbers or counts. Consequently, modulation can be referred to as positive or negative. Positive modulation (also referred to as up-regulation) of inflammation may result in an increase in the number of Th40 cells in the inflammatory environment. Negative modulation (also referred to as down-regulation) of inflammation may result in a reduction in the number of Th40 cells present in the inflammatory environment. The level, count, or concentration of Th40 cells may not be indicative of inflammation in the inflammatory environment. A preferred peptide may be one that down-regulates inflammation, thereby reducing the number of Th40 cells present in the inflammatory environment. Positive and negative modulation of inflammation may or may not result in a change in the type and amount of immunoregulatory molecules present in the inflammatory environment. In some instances, it is possible that the Th40 levels will not change but the activity of those cells is altered such that they are no longer exerting or increasing inflammatory cytokines and other biomarkers of inflammation. Therefore, as used herein modulating inflammation may refer to changes in the Th40 levels, numbers, or concentration in a corporeal body or sample, and may also refer to changes in inflammation more generally that may be associated with disease, inflammatory cytokines, and/or cell derived inflammatory mediator molecules.

It will be appreciated by those skilled in the art that both a cell culture system and the immune system of an animal comprise basal levels of immune cells and immunoregulatory molecules. The phrases basal level and normal level can be used interchangeably. With regard to the immune system of an animal, as used herein, the basal level of a type of immune cell (e.g., Th40 cell), or a immunoregulatory molecule, refers to the average number of that cell type, or immunoregulatory molecule, present in a population of individuals considered healthy (i.e., free of metabolic, autoimmune, or infectious disease). With regard to a cell culture system, as used herein, the basal level of a type of immune cell, or an immunoregulatory molecule, refers to the average level of that cell type, or immunoregulatory molecule, present in a population of cells that is non-activated. Those skilled in the art are capable of determining if a T-cell, or a population of such cells, is activated. For example, the expression of CD69, CD25 and/or CD154 proteins by a cell indicates that the cell has been activated.

The basal level of a cell or molecule can be a specific amount (e.g., a specific concentration) or it can encompass a range of amounts. Basal levels, or ranges, of immune cells and immunoregulatory molecules are known to those in the art. For example, in a healthy individual, the normal level of CD4+ T-cells present in human blood is 500-1500 cells/ml. Variability in this measurement can result from differences in the method used to determine the cell count. Furthermore, normal levels of cells can also be reported as a percentage of a total cell population. For example, in a healthy individual, Th40 cells make up less than 25% of the total T cell population. Thus, as used herein, the term inflammation refers to an inflammatory environment in which Th40 cells make up greater than about 25%, greater than about 30%, greater than about 35%, greater than about 40%, greater than about 45%, greater than about 50%, greater than about 55%, greater than about 60%, greater than about 65%, greater than about 70%, greater than about 75%, or greater than about 80% of the total T-cell population. Moreover, a preferred peptide herein is one that reduces the level of Th40 cells to less than about 50%, less than about 45%, less than about 40%, less than about 35%, less than about 30%, less than about 27%, or equal to about 25% of the total T-cell population. Methods of measuring different types of T-cells in the T-cell population are known to those skilled in the art. Furthermore, a novel method for detecting Th40 cells using peptides hereof is disclosed herein.

As used herein, the phrase inflammatory environment refers to the overall population of immune cells, and related immunoregulatory molecules, that are present in a culture of cells, or in the body of an animal. As such, the phrase inflammatory environment encompasses the types, and/or the relative amounts of immune cells and immunoregulatory molecules (e.g., cytokines) present in a culture of cells, or in an animal, which are involved in affecting an inflammatory reaction. Examples of cells encompassed by the term inflammatory environment include, but are not limited to, T cells, neutrophils, macrophages, granulocytes, and the like. The inflammatory environment relates to cells and molecules that mediate both acute and chronic inflammation. It will be appreciated by those skilled in the art that the inflammatory environment refers to the system to which peptides hereof are administered. In one embodiment, the system is a cell culture system. In one embodiment, the system is a whole animal.

A preferred peptide hereof is one that selectively interacts with a CD40 protein in solution, as determined using an assay such as an immunosorbent assay, or on the surface of a T-cell. As used herein, the terms selectively, selective, specific, and the like, indicate the peptide has a greater affinity for a CD40 protein than it does for proteins unrelated to the CD40 protein. More specifically, the terms selectively, selective, specific, and the like indicate that the affinity of the peptide for CD40 is statistically significantly higher than its affinity for a negative control (e.g., an unrelated protein such as albumin) as measured using a standard assay (e.g., ELISA). Suitable techniques for assaying the ability of a peptide to selectively interact with a CD40 protein are known to those skilled in the art. Such assays can be in vitro or in vivo assays. Examples of useful assays include, but are not limited to, an enzyme-linked immunoassay, a competitive enzyme-linked immunoassay, a radioimmunoassay, a fluorescence immunoassay, a chemiluminescent assay, a lateral flow assay, a flow-through assay, an agglutination assay, a particulate-based assay (e.g., using particulates such as, but not limited to, magnetic particles or plastic polymers, such as latex or polystyrene beads), an immunoprecipitation assay, an immunoblot assay (e.g., a western blot), a phosphorescence assay, a flow-through assay, a chromatography assay, a polyacrylamide gel electrophoresis (PAGE)-based assay, a surface plasmon resonance assay, a spectrophotometric assay, a particulate-based assay, an electronic sensory assay and a flow cytometric assay. Methods of performing such assays are well known to those skilled in the art. In one embodiment, an assay can be performed using cells in culture, or it can be performed in a whole animal. Assays can be designed to give qualitative, quantitative or semi-quantitative results, depending on how they are used and the type of result that is desired.

One embodiment hereof is a peptide that interacts with a CD40 protein in such a manner as to affect the interaction of the CD40 protein with a CD154 protein, thereby modulating inflammation. The effect of the peptide on the CD40/CD154 interaction can be positive or it can be negative. For example, the peptide can interact with the CD40 protein in such a manner that the strength of the interaction between the CD40 protein and a CD154 protein is increased. Alternatively, the peptide can interact with the CD40 protein such that the strength of the interaction between the CD40 protein and a CD154 protein is decreased. Methods of measuring the strength of binding between the peptide and a CD40 protein are known to those skilled in the art. A preferred peptide hereof is one that reduces the strength of the interaction between a CD40 protein and a CD154 protein. Preferred peptides hereof reduce the strength of binding between a CD40 protein and a CD154 protein by at least 10%, at least 20%, at least 30%, at least 40%, at least 50%, at least 60%, at least 70%, at least 80%, at least 90%, or at least 95%. A particularly preferred peptide is one that completely inhibits binding of CD40 to CD154. Complete inhibition of binding between CD40 and CD154 means that when a peptide hereof is brought into proximity with a CD40 protein and a CD154 protein under conditions that would normally allow the interaction of CD40 and CD154, no such interaction occurs and activation signals are not stimulated in the CD40-expressing cell. Consequently CD40/CD154 mediated modulation of inflammation does not occur. In one embodiment, the peptide interacts with the CD40 protein in such a manner as to reduce the level of inflammation in the system. In one embodiment, the peptide interacts with the CD40 protein in such a manner as to inhibit the development of inflammation in the system. In one aspect, the peptide may alter the way the cells may interact with other molecules that normally occur during cell-to-cell interactions. Such cell-to-cell interactions may be those that result in inflammation. The peptides of the developments hereof, may disrupt the inflammasome complex, which may promote the maturation of pro-inflammatory cytokines interleukin-1β (IL-1β) and interleukin-18 (IL-18). Furthermore, one aspect of the peptides hereof is that these peptides may disrupt the inflammasome complex of caspase 1, PYCARD. NALP, caspase 5, nucleotide-binding oligomerization domain and leucine-rich repeat-containing receptors (NLRs) and ALRs (AIM2-like receptors).

One aspect of the peptides described herein is that administration of the peptide may alter the way the cell may interact with other molecules that normally occur during cell to cell interactions which may be indicative of or result in inflammation. One aspect of the peptides described herein is that these peptide(s) may disrupt the inflammasome and thus alter inflammatory outcomes.

While peptides hereof can interact with any site on the CD40 protein, preferred peptides interact with the CD40 protein at a location that overlaps with the CD154 binding site. In one embodiment, a peptide hereof interacts with the CD40 protein at the CD154 binding site. An example of such a peptide is a CD40 ligand competitive antagonist. As used herein, peptides that interfere with, or inhibit, the binding of a CD154 protein to a CD40 protein are referred to as small interfering peptides (SIPs). As used herein a small interfering peptide is a peptide that, through physio-chemical properties, interferes with the interaction of a CD40 protein with a CD154 protein, thereby preventing activation signals from being delivered to the CD40-bearing cell, thus limiting the activation of the CD40-bearing cell, and consequently, inflammation. As demonstrated herein, the consequences of such interference are prevention of T-cell activation and propagation, and a prevention or reduction of inflammation.

Additionally, a small interfering peptide, may, through its physio-chemical properties, interfere with the interaction of a CD40 protein with a CD154 protein, thereby preventing activation signals from being delivered to the CD40-bearing cell, thus limiting the activation of the CD40-bearing cell, and consequently, modulating, inhibiting, preventing, and/or reversing type 2 diabetes. As demonstrated herein, the consequences of such interference are prevention of T cell activation and propagation, and a prevention, reduction, modulation, and reversal of type 2 diabetic developments.

A peptide useful for practicing methods of the present developments should be of a size sufficient to interact with CD40 protein in such a manner as to modulate type 2 diabetes. It is understood by those skilled in the art that preferred peptides are relatively short since they are easier and less expensive to produce. Preferred peptides are those that are less than 20 amino acids in length. A preferred peptide is one that is 4, 6, 8, 10, 13, 15, or 24 amino acids in length. In one embodiment, the peptide is an amino acid selected from the group of SEQ ID NO:3 (Core-sequence see Table 1), SEQ ID NO:4 (6-mer see Table 1). SEQ ID NO:5 (8-mer mouse see Table 1), SEQ ID NO:6 (8-mer human see Table 1). SEQ ID NO:7 (15-mer mouse see Table 1), SEQ ID NO:8 (15-mer human see Table 1), SEQ ID NO:9 (24-mer see Table 1), SEQ ID NO: 24 (10-mer see Table 1), SEQ ID NO: 25 (13-mer see Table 1), SEQ ID NO: 26 (24-mer see Table 1), SEQ ID NO: 27 (6-mer (Form 2) see Table 1). SEQ ID NO: 28 (6-mer (Form 3) see Table 1). SEQ ID NO: 29 (6-mer (Form 4) see Table 1), SEQ ID NO: 30 (6-mer (Form 4) see Table 1) and SEQ ID NO:32 (24-mer-mouse (Form 2)). The sequences of such peptides are shown below in Table 1 (which is an exact duplicate of the previously listed Table 1, but repeated here for the convenience of the reader).

TABLE 1

| SEQ ID NO | SEQUENCE | Description |
|---|---|---|
| 1 | MIETYSQPSP RSVATGLPAS MKIFMYLLTV FLITQMIGSV LFAVYLHRRL DKVEEEVNLH EDFVFIKKLK RCNKGEGSLS LLNCEEMRRQ FEDLVKDITL NKEEKKENSF EMQRGDEDPQ IAAHVVSEAN SNAASVLQWA KKGYYTMKSN LVMLENGKQL TVKREGLYYV YTQVTFCSNR EPSSQRPFIV GLWLKPSSGS ERILLKAANT HSSSQLCEQQ SVHLGGVFEL QAGASVFVNV TEASQVIHRV GFSSFGLLKL | SwissPro 27548.2 Mouse CD40 Ligand (CD154 Protein) |
| 2 | MIFTYNQTSP RSAATGLPIS MKIFMYLLTV FLITQMIGSA LFAVYLHRRL DKIEDERNLH EDFVFMKTIQ RCNTGERSLS LLNCEEIKSQ FEGFVKDIML NKEFTKKENS FEMQKGDQNP QIAAHVISEA SSKTTSVLQW AEKGYYTMSN NLVTLENGKQ LTVKRQGLYY IYAQVTFCSN REASSQAPFI ASLCLKSPGR FERILLRAAN THSSAKPCGQ QSIHLGGVFE LQPGASVFVN VTDPSQVSHG TGFTSFGLLK L | SwissPro 29965 Human CD40 Ligand (CD154 Protein) |
| 3 | KGYY | Core-sequence |
| 4 | KKGYYT | 6-mer |
| 5 | AKKGYYTM | 8-mer-mouse |
| 6 | AEKGYYTM | 8-mer human |
| 7 | VLQWAKKGYYTMKSN | 15-mer-mouse |

TABLE 1-continued

| SEQ ID NO | SEQUENCE | Description |
|---|---|---|
| 8 | VLQWAEKGYYTMSNN | 15-mer human |
| 9 | NAASVLQWAKKGYYTMKSNLVMLE | 24-mer |
| 10 | ISQAVHAAHAEINEAGR | 15-mer from ovalbumin; control peptide |
| 11 | G-L-Q-W-A-K-K-G-Y-Y-T-M-K-S-N | Gly-1 |
| 12 | V-G-Q-W-A-K-K-G-Y-Y-T-M-K-S-N | Gly-2 |
| 13 | V-L-G-W-A-K-K-G-Y-Y-T-M-K-S-N | Gly-3 |
| 14 | V-L-Q-G-A-K-K-G-Y-Y-T-M-K-S-N | Gly-4 |
| 15 | V-L-Q-W-G-K-K-G-Y-Y-T-M-K-S-N | Gly-5 |
| 16 | V-L-Q-W-A-G-K-G-Y-Y-T-M-K-S-N | Gly-6 |
| 17 | V-L-Q-W-A-K-G-G-Y-Y-T-M-K-S-N | Gly-7 |
| 18 | V-L-Q-W-A-K-K-G-G-Y-T-M-K-S-N | Gly-8 |
| 19 | V-L-Q-W-A-K-K-G-Y-G-T-M-K-S-N | Gly-9 |
| 20 | V-L-Q-W-A-K-K-G-Y-Y-G-M-K-S-N | Gly-10 |
| 21 | V-L-Q-W-A-K-K-G-Y-Y-T-G-K-S-N | Gly-11 |
| 22 | ISQAVHAAHAEINEAGR | 15-mer from ovalbumin; control peptide |
| 23 | YVQGKANLKSKLMYT | Scrambled peptide |
| 24 | WAKKGYYTMK | 10-mer mouse |
| 25 | VLQWAKKGYYTMK | 13-mer mouse |
| 26 | AASVLQW AKKGYYTMKSNLVVLEN | 24-mer mouse |
| 77 | KGYYTM | 6-mer (Form 2) |
| 28 | AEKGYY | 6-mer (Form 3) |
| 29 | AKKGYY | 6-mer (Form 4) |
| 30 | AKGYYT | 6-mer (Form 5) |
| 31 | YKNVKQMAYWLTGKS | Scrambled peptide |
| 32 | AASVLQWAKKGYYTMKSNLVMLEN | 24-mer-mouse (Form 2) |

Interaction of a CD40 protein and a CD154 protein has been shown to occur at particular regions within each protein. The inventors have now shown that, surprisingly, a peptide comprising only a short portion of the CD154 region that interacts with CD40 is capable of binding to a CD40 protein, thereby modulating type 2 diabetes. Thus one embodiment hereof is a peptide that comprises at least a portion of the amino acid sequence of a CD154 protein such that the peptide interacts with CD40 protein in such a manner as to modulate type 2 diabetes. In one embodiment, interaction of the peptide with CD40 protein results in negative modulation, reduction, or inhibition of type 2 diabetes. In one aspect, the peptide comprises at least a portion of SEQ ID NO:1 or SEQ ID NO:2.

In one aspect, the peptide is as short as possible yet comprises enough of the CD154 protein to allow interaction with a CD40 protein in such a manner as to modulate type 2 diabetes. In one embodiment, a peptide hereof comprises 6, 13 or 15 contiguous amino acids from SEQ ID NO:1 or SEQ ID NO:2, and interacts with CD40 in such a manner as to modulate type 2 diabetes. A preferred peptide comprises a core sequence of lysine-glycine-tyrosine-tyrosine (KGYY; SEQ ID NO:3), which corresponds to amino acids 142-145 of SEQ ID NO:1 and amino acids 143-146 of SEQ ID NO:2. Moreover, another preferred peptide comprises a core sequence of lysine-glycine-tyrosine-tyrosine-threonine-methionine (KGYYTM; SEQ ID NO:27), which corresponds to amino acids 142-147 of SEQ ID NO:1 and amino acids 143-148 of SEQ ID NO:2. Useful peptides can comprise additional regions of sequence from SEQ ID NO:1 or SEQ ID NO:2 that are adjacent to the core sequence, so long as the peptide is capable of modulating type 2 diabetes. In one embodiment, a peptide comprises at least one sequence selected from SEQ ID NO:3, SEQ ID NO:4, SEQ ID NO:7. SEQ ID NO:8, SEQID NO:9, SEQ ID NO:27, SEQ ID NO:28, SEQ ID NO:29, SEQ ID NO:30 and SEQ ID NO:32 so long as the peptide interacts with CD40 protein in such a manner as to modulate type 2 diabetes. In one embodiment of the present subject matter, a peptide hereof is a sequence selected from SEQ ID NO:3, SEQ ID NO:4, SEQ ID NO:7. SEQ ID NO:8. SEQID NO:9. SEQ ID NO:27, SEQ ID NO:28. SEQ ID NO:29. SEQ ID NO:30 and SEQ ID NO:32.

While peptides of the present subject matter can be selected entirely of or from sequences that are responsible for the interaction of the peptide with a CD40 protein, they may additionally contain amino acid sequences that do not interact with a CD40 protein, but which have other useful functions. Any useful, additional amino acid sequence can be added to the CD40-interacting sequence, so long as the additional sequences do not have an unwanted effect on the ability of the CD40 interacting sequence to interact with a CD40 protein. For example, in addition to the amino acid sequence responsible for interacting with a CD40 protein, a peptide hereof can contain amino acid sequences that are useful for visualizing or purifying the peptide. Such sequences act as labels (e.g., enzymes) or tags (antibody binding sites). Additionally, the developments presented herein demonstrate that substitutions of amino acids at any position other than the position-7 (K) of the 15-mer and the position-9 (Y) of the 15-mer may be made and the integrity and function of the peptide may be maintained (see FIG. 8). Accordingly, these developments may contemplate that numerous substitutions may be possible while still maintaining the beneficial aspects of the peptide.

Any useful, additional amino acid sequence can be added to the CD40-interacting sequence, so long as the additional sequences do not have an unwanted effect on the ability of the CD40 interacting sequence to interact with a CD40 protein. For example, in addition to the amino acid sequence responsible for interacting with a CD40 protein, a peptide hereof can contain amino acid sequences that are useful for visualizing or purifying the peptide. Examples of such labels and tags include, but are not limited to, B-galactosidase, luciferase, glutathione-s-transferase, thioredoxin, HIS-tags, biotin tags, and fluorescent tags. Moreover, acetyl groups and amides may be appended on the N-terminus or C-terminus, and the developments hereof contemplate these and other variations that may enhance stability or other traits desired of such a peptide. Other useful sequences for labeling and tagging proteins are known to those of skill in the art.

Likewise, peptides hereof can be modified, so long as such modification does not significantly affect the ability of the peptide to modulate type 2 diabetes. Such modifications can be made, for example, to increase the stability, solubility or absorbability of the protein. Examples of such modifications include, but are not limited to pegylation, glycosylation and chemical modification of the peptide.

Peptides hereof may possibly be derived from nature (e.g., obtained from plants, animals or microorganisms) or they can be produced in a laboratory (e.g., recombinantly or synthetically). Preferred peptides are those that are synthesized. Also encompassed are peptides that are combinations of natural and synthetic molecules. General methods for producing and isolating recombinant or synthetic peptides are known to those skilled in the art. It should be noted that, as used herein, an isolated, or biologically pure, molecule, is one that has been removed from its natural milieu. As such the terms isolated, biologically pure, and the like, do not necessarily reflect the extent to which the protein has been purified.

The peptides hereof do not arise naturally in a corporeal body, but rather must be constructed and synthesized to obtain the small interfering peptides. Certain aspects of the design and synthesis may affect the peptides stability and ability to perform its intended use. The peptides hereof may vary in length from four amino acids in length as in SEQ ID NO:3, five amino acids in length, six amino acids in length as in SEQ ID NOs: 4, 27, 28, 29, and 30, seven amino acids in length, eight amino acids in length as in SEQ ID NOs: 5 and 6, nine amino acids in length, ten amino acids in length as in SEQ ID NOs: 24, eleven amino acids in length, twelve amino acids in length, thirteen amino acids in length as in SEQ ID NO: 25, fourteen amino acids in length, fifteen amino acids in length as in SEQ ID NOs: 7, 8, 11, 12, 13, 14, 15, 16, 17, 18, and 20, sixteen amino acids in length, seventeen amino acids in length, eighteen amino acids in length, nineteen amino acids in length, twenty amino acids in length, twenty-one amino acids in length, twenty-two amino acids in length, twenty-three amino acids in length, twenty-four amino acids in length as in SEQ ID NO: 26 and 32, and twenty-five amino acids in length. In some instances, the embodiments of this development may be up to fifty or more amino acids in length and in such instances, repeats of the core sequence of SEQ ID NO: 3, may occur one, two, three, four, five, six, seven, eight, nine, ten, eleven or more times in such a peptide. In other instances, the embodiments of this development may be up to fifty or more amino acids in length, and in such instances repeats of the core sequence of SEQ ID NO:3, may be varied with other sequences known to provide the desired effect such as those of SEQ ID NOS: 4-9, 25-30, and 32. The repeats and sequences of said variations are countless; however, the developments herein contemplate a peptide that maintains its ability to perform its intended use of interacting with CD40 in such a manner as change, control, or affect inflammation in the subject.

As has been described herein, interaction of the CD40 protein and the CD154 protein are necessary for involvement of Th40 cells in type 2 diabetes. Consequently, inhibition of the interaction between a CD40 and CD154 protein using peptides hereof is a useful method of affecting type 2 diabetes. Thus, one embodiment is a method to reduce the interaction between a CD40 protein and a CD154 protein comprising introducing into an environment containing a CD40 protein and a CD154 protein, a peptide, that interacts with the CD40 protein in such a manner as to reduce the interaction between the CD40 protein and the CD154 protein. In one aspect hereof, the peptide reduces the interaction between the CD40 protein and the CD154 protein by at least 5%, at least 10%, at least 20%, at least 30%, at least 40%, at least 50%, at least 60%, at least 70%, at least 80%, at least 90%, or at least 95%. In one embodiment, the peptide reduces the interaction between the CD40 protein and the CD154 protein by a factor of at least 10, at least 100, at least 1,000, at least 10,000. Methods of measuring the strength of the interaction between the CD40 protein and the CD154 protein have been discussed previously, and are also know to those of skill in the art.

One embodiment hereof is a method to modulate type 2 diabetes comprising contacting a CD40 protein with a peptide that interacts to the CD40 protein in such a manner as to modulate inflammation. In one aspect, interaction of the peptide with the CD40 protein increases the number of Th40 cells by at least 5%, at least 10%, at least 20%, at least 30%, at least 40%, at least 50%, at least 60%, at least 70%, at least 80%, at least 90%, or at least 95%. In one embodiment, interaction of the peptide with the CD40 protein increases the number of Th40 cells by a factor of at least 10, at least 100, at least 1,000, at least 10,000.

One aspect is a method to reduce type 2 diabetes in a patient, the method comprising administering a peptide hereof to the patient. In one embodiment, the peptide comprises an amino acid sequence selected from SEQ ID NO:3, SEQ ID NO:4, SEQ ID NO:5, SEQ ID NO: 6, SEQ ID NO:7, SEQ ID NO:8. SEQ ID NO:9, SEQ ID NO:25. SEQ ID NO:26, SEQ ID NO:27, SEQ ID NO: 28, SEQ ID NO: 29. SEQ ID NO:30 and SEQ ID NO:32. In one embodiment, the peptide is an amino acid sequence selected from SEQ ID NO:4. SEQ ID NO:8, SEQ ID NO:9. SEQ ID NO:27, SEQ ID NO: 28, and SEQ ID NO: 29. In a preferred embodiment, interaction of the peptide with the CD40 protein decreases the number of Th40 cells by at least 5%, at least 10%, at least 20%, at least 30%, at least 40%, at least 50%, at least 60%, at least 70%, at least 80%, at least 90%, or at least 95%. In another embodiment, interaction of the peptide with the CD40 protein decreases the number of Th40 cells by a factor of at least 10, at least 100, at least 1.000, at least 10.000. In a preferred embodiment, the level of Th40 cells is reduced so that Th40 cells comprise no more than about 20%, about 25%, about 30%, about 35%, or about 40% of the total T-cell population.

Peptides and methods hereof are suitable for use in cell culture as well as for treating a patient. As used herein the term patient refers to any animal in need of such treatment. The animal can be a human or a non-human animal. A preferred animal to treat is a mammal. A peptide can be administered or applied per se, or as pharmaceutical compositions. A peptide hereof, or a pharmaceutical composition thereof, can be administered to a patient by a variety of routes, including, but limited to, by injection (e.g., intravenous, intramuscular, subcutaneous, intrathecal, intraperitoneal), by inhalation, by oral (e.g., in a pill, tablet, capsule, powder, syrup, solution, suspension, thin film, dispersion or emulsion), transdermal, transmucosal, pulmonary, buccal, intranasal, sublingual, intracerebral, intravaginal rectal or topical administration or by any other convenient method known to those of skill in the art.

The amount of a peptide hereof and/or a pharmaceutical composition thereof that will be effective can be determined by standard clinical techniques known in the art. Such an amount is dependent on, among other factors, the patient being treated, including, but not limited to the weight, age, and condition of the patient, the intended effect of the compound, the manner of administration and the judgment of the prescribing physician. Also, in this context, it should be noted that in treating a patient exhibiting a disorder of interest, a therapeutically effective amount of an agent or agents such as these is administered. A therapeutically effective dose refers to that amount of the compound that results in amelioration of one or more symptoms or a prolongation of survival in a patient.

A peptide hereof, or a pharmaceutical composition thereof, can be administered alone or in combination with one or more other pharmaceutical agents, including other compounds of the present disclosure. The specific pharmaceutical composition depends on the desired mode of administration, as is well known to the skilled artisan.

Because the inventors have discovered that Th40 cells are intimately involved in the development of autoimmune diseases and type 2 diabetes, the peptides and methods disclosed herein can be used to affect conditioning resulting from such diseases. Thus, one embodiment hereof is a method to treat type 2 diabetes in a patient in need of such treatment, the method comprising administering to a patient a peptide that interacts with the CD40 protein, thereby reducing type 2 diabetes. In one embodiment the peptide interacts with the CD40 protein in such a manner as to affect the interaction of CD40 and CD154, thereby reducing type 2 diabetes. In a preferred embodiment, interaction of the peptide with the CD40 protein reduces the number of Th40 cells in a patient to a level equal to that observed in subjects that do not have type 2 diabetes. In another embodiment, interaction of the peptide with the CD40 protein reduces the inflammatory cytokine levels in a patient. In another embodiment, interaction of the peptide with the CD40 protein reduces the inflammatory cytokine levels in a patient to a level equal or similar to those observed in subjects that do not have type 2 diabetes. The present developments are suitable for treating any patient having an autoimmune disease and/or cardiovascular disease, the development of which may be related to, correlated with, or dependent on Th40 cells. The present developments may also be suitable for treating any patient having an autoimmune disease and/or cardiovascular disease, the development of which is not related to, correlated with, or dependent on Th40 cell counts, levels, and or concentrations.

In one embodiment, more specifically, peptides hereof may be suitable for reducing the level of Th40 cells in such patients. In this embodiment, a peptide hereof may reduce the level of Th40 cells in a patient suffering from an autoimmune disease to no more than about 25% of the total T-cell population.

One example of a disease that is particularly amenable to treatment using a peptide of the present developments may be type 2 diabetes. In type 2 diabetes, glucose tolerance is reduced, insulin sensitivity is decreased, and plasma insulin levels are increased. Consequently, control of inflammatory cells and cell signaling via CD40-CD154 interaction may be able to be used to control, modulate, reduce and/or reverse type 2 diabetes symptoms that are characterized as by glucose intolerance, insulin resistance, and increased plasma insulin levels. Several murine models of T2D and/or atherosclerosis have been developed. For initial studies, ApoE−/− mice were selected due to their ability to develop type 2 diabetes from a high fat diet. Glucose tolerance and insulin testing were performed on all of the mice. The mice were administered the 6-mer peptide (SEQ ID NO:29) at a rate of 1 mg/kg weekly via I.V, injection and monitored. Peptide treated ApoE deficient mice demonstrated significantly increased glucose tolerance as well as significantly improved insulin sensitivity, improve insulin resistance, and lowered plasma insulin levels compared to controls. Thus, one embodiment of the present developments is a method to prevent type 2 diabetes in an individual at risk for developing type 2 diabetes, the method comprising administering to the individual a peptide to selectively bind to a CD40 expressing cell. In such an embodiment, the peptide may be selected from SEQ ID NOS: 3-9 and 24-30.

The developments hereof have also shown that, surprisingly, peptides hereof can be used to reverse the disease process in individuals already showing signs of type 2 diabetes. Thus, one aspect of the present subject matter is a method to reverse type 2 diabetes comprising administering to a patient diagnosed as having type 2 diabetes, a peptide hereof. In one embodiment, the peptide comprises an amino acid sequence selected from SEQ ID NO:3, SEQ ID NO:4. SEQ ID NO:7, SEQ ID NO:8. SEQ ID NO:9, SEQ ID NO:27, SEQ ID NO:28. SEQ ID NO:29, and SEQ ID NO:30, so long as the peptide can down-regulate or reduce inflammation. In one embodiment, the peptide is an amino acid sequence selected from SEQ ID NO:3, SEQ ID NO:4, SEQ ID NO:7. SEQ ID NO:8, SEQ ID NO:9, SEQ ID NO:27, SEQ ID NO:28, SEQ ID NO:29, and SEQ ID NO:30. As used herein the phrase to reverse type 2 diabetes means to increase glucose tolerance, decrease insulin resistance, and decrease plasma insulin levels to levels closer to or more comparable to those observed in individuals who do not have type 2 diabetes.

In yet another development hereof has shown that, surprisingly, peptides hereof can be used to reverse the disease process in individuals already showing signs of type 2 diabetes. Thus, one aspect of the present subject matter is a method to reverse type 2 diabetes comprising administering to a patient diagnosed as having type 2 diabetes, a peptide hereof. In one embodiment, the peptide comprises an amino acid sequence selected from SEQ ID NOS: 3-9 and 24-30, so long as the peptide can control, modulate, reduce and/or reverse inflammation. In one embodiment, the peptide is an amino acid sequence selected from SEQ ID NOS: 3-9 and 24-30, so long as the peptide can control, modulate, reduce and/or reverse type 2 diabetes. Furthermore, in one aspect of this embodiment a peptide hereof may reduce the level of Th40 cells in a patient suffering from an autoimmune disease to no more than about 25% of the total T-cell population. In an alternative embodiment, interaction of the peptide with the CD40 protein reduces the number of Th40 cells in a patient to a level equal to that observed in subjects that do not have type 2 diabetes. In another embodiment, interaction of the peptide with the CD40 protein reduces the inflammatory cytokine levels in a patient. In another embodiment, interaction of the peptide with the CD40 protein reduces the inflammatory cytokine levels in a patient to a level equal or similar to those observed in subjects that do not have type 2 diabetes. The present developments may be suitable for treating any patient having an autoimmune disease and/or cardiovascular disease, the development of which may be related to, correlated with, or dependent on Th40 cells. The present developments may also be suitable for treating any patient having an autoimmune disease and/or cardiovascular disease, the development of which is not related to, correlated with, or dependent on Th40 cell counts, levels, and or concentrations.

As has been described, peptides of the present invention selectively bind to a CD40 expressing cell. Consequently, peptides of the present subject matter can be used to identify Th40 cells. Thus one embodiment hereof is a method to detect Th40-dependent type 2 diabetes, said method comprising contacting a T-cell population with a peptide hereof. In a preferred embodiment, the peptide is labeled with a detectable marker, such as, for example, fluorescein, luciferase or alkaline phosphatase. Such detection can be performed using assay techniques known to those skilled in the art. In general, an assay for detecting Th40 cells using a peptide hereof comprises (a) obtaining a sample of cells; (b) contacting a peptide hereof with said cells under condition suitable to allow binding of the peptide to Th40 cells, if present; (c) washing said cells using conditions that disrupt non-specific interactions, and that remove unbound peptide; and (d) detecting peptide bound to cells. Detection of bound peptide can be achieved directly or indirectly. For example, direct detection can be achieved using a peptide labeled using a detectable marker, as disclosed herein. Following the wash step listed above, the cells are then simply screened for the presence of detectable marker. The presence of detectable marker in the cell sample indicates the presence of Th40 cells, and thus Th40-dependent type 2 diabetes. Alternatively, indirect detection involves the use of a second molecule, such as an antibody, that binds to the peptide. In an indirect detection assay, following the wash step listed above, a detection molecule that binds the peptide is added to the cell sample. The detection molecule is labeled with a detectable marker. After washing away unbound detection molecule, the cells are screened for the presence of detectable marker. The presence of detectable marker in the cell sample indicates the presence of Th40 cells. It should be understood that the assays described herein are meant as examples of useful assays, and other assay techniques can be employed. Suitable assay techniques are known to those skilled in the art, and are also disclosed in, for example, Molecular Cloning: A Laboratory Manual. Sambrook, J., Fritsch, E. F., and Maniatis, T, Cold Spring Harbor Laboratory Press; 2nd Edition (December 1989). All references cited herein are incorporated herein in their entirety.

The assay technology described above can also be used to identify other molecules that affect the interaction of a CD40 protein with a CD514 protein. Examples of such molecules include, but are not limited to, proteins, peptides and small molecules. For example, assays can be designed that test the ability of molecules to compete with a peptide of the present developments for binding to a Th40 cell. For instance, a peptide labeled with a detectable marker, can be mixed with a test molecule and a population of cells known to contain Th40 cells, under conditions that allow binding of the peptide to the Th40 cells. Following an appropriate incubation period, the cells are washed to remove unbound peptide, and the cells screened for the presence of detectable marker. Alternatively, the labeled peptide could be bound to Th40 cells first, and after a wash step to remove unbound peptide, the test molecule could be added to the cells containing bound peptide. Following an incubating period and a wash step to remove unbound molecule, or released peptide, the cells are screened for the presence of detectable marker. In either case, absence of the detectable marker in the cell sample indicates the test molecule is able to compete with the peptide for binding to the Th40 cells, while presence of the detectable marker would indicate the test molecule does not inhibit binding of the peptide to Th40 cells. Inhibition of binding need not be 100%, as such assay would also be useful for identifying molecules that partially inhibit binding of the peptide to Th40 cells. It is understood by those skilled in the art that such assays would involve the use of positive controls (e.g., unlabeled peptide) and negative controls (e.g., a protein/molecule that is known not to bind to Th40 cells).

The assay technology above can also be used to identify other molecules that affect the interaction of a CD40 protein with a CD154 proteins. Examples of such molecules include, but are not limited to, proteins, peptides and small molecules. For example, assays can be designed that test the ability of molecules to compete with a peptide of the present developments for binding to a CD40 protein of cells other than T cells, such as neutrophils, cosinophils, basophils, mast cells, macrophages, platelets, endothelial cells, and lymphocytes, including natural killer cells and B cells. For instance, a peptide labeled with a detectable marker, can be mixed with a test molecule and a population of cells known to contain CD40 containing cells, under conditions that allow binding of the peptide to the CD40 bearing cells. Following an appropriate incubation period, the cells are washed to remove unbound peptide, and the cells screened for the presence of detectable marker. Alternatively, the labeled peptide could be bound to CD40 bearing cells first, and after a wash step to remove unbound peptide, the test molecule could be added to the cells containing bound peptide. Following an incubating period and a wash step to remove unbound molecule, or released peptide, the cells are screened for the presence of detectable marker. In either case, absence of the detectable marker in the cell sample indicates the test molecule is able to compete with the peptide for binding to the CD40 bearing cells, while presence of the detectable marker would indicate the test molecule does not inhibit binding of the peptide to CD40 bearing cells. Inhibition of binding need not be 100%, as such assay would also be useful for identifying molecules that partially inhibit binding of the peptide to CD40 bearing cells. It is understood by those skilled in the art that such assays would involve the use of positive controls (e.g., unlabeled peptide) and negative controls (e.g., a protein/molecule that is known not to bind to CD40 bearing cells).

Because increased levels of Th40 cells are associated with the development of autoimmune disease, the present developments can be used to identify patients at risk for developing autoimmune disease and autoimmune related type 2 diabetes. Thus, one embodiment of the present developments is a method to identify a patient at risk for developing autoimmune related type 2 diabetes. In one embodiment, patients at risk for developing type 2 diabetes are identified by obtaining a sample from a patient to be tested, contacting the T-cell portion of said sample with a peptide hereof, and determining the level of Th40 cells present in the sample, wherein a level of Th40 cells greater than about 25% of the total T-cell population indicates the patient is at risk for developing type 2 diabetes. In one embodiment, the peptide comprises an amino acid sequence selected from SEQ ID NO:3, SEQ ID NO:4. SEQ ID NO:7. SEQ ID NO:8, SEQ ID NO:9. SEQ ID NO:27, SEQ ID NO:28, SEQ ID NO:29, and SEQ ID NO:30, so long as the peptide binds to the CD40 protein. In one embodiment, the peptide is an amino acid sequence selected from SEQ ID NO:3, SEQ ID NO:4. SEQ ID NO: 7. SEQ ID NO:8, SEQ ID NO:9, SEQ ID NO:27, SEQ ID NO:28. SEQ ID NO:29, and SEQ ID NO:30. In a preferred embodiment the peptide is labeled with a suitable detectable marker such as, for example, fluorescein, luciferase or alkaline phosphatase. In yet another embodiment, the peptide comprises an amino acid sequence selected from SEQ ID NOs: 4-9, 24-30, and 32, so long as the peptide binds to the CD40 protein.

The present developments also comprise kits useful for practicing the methods disclosed herein, the kit comprising a peptide that interacts with a CD40 protein in such a manner as to modulate, reduce, prevent, treat, or otherwise improve symptoms of type 2 diabetes. In one embodiment, the peptide comprises an amino acid sequence selected from SEQ ID NO:3, SEQ ID NO:4. SEQ ID NO:7, SEQ ID NO:8. SEQ ID NO:9. SEQ ID NO:27, SEQ ID NO:28. SEQ ID NO:29, and SEQ ID NO:30, so long as the peptide can modulate type 2 diabetes. In one embodiment, the peptide is an amino acid sequence selected from SEQ ID NO:3. SEQ ID NO:4, SEQ ID NO:7, SEQ ID NO:8, SEQ ID NO:9, SEQ ID NO:27, SEQ ID NO:28, SEQ ID NO:29, and SEQ ID NO:30. Another embodiment is a kit for determining the level of Th40 cells, the kit comprising a peptide that interacts with a CD40 protein, and methods for detecting CD40-bound peptide. Kits can also contain associated reagents and components, such as, but not limited to, buffers, labels, containers, inserts, tubing, vials, syringes, and the like.

The present developments also comprise kits useful for practicing the methods disclosed herein, the kit comprising a peptide that interacts with a CD40 protein in such a manner as to modulate, reduce, prevent, treat, or otherwise improve symptoms of type 2 diabetes. In one embodiment, the peptide comprises an amino acid sequence selected from SEQ ID NOs: 3-9 and 24-30, so long as the peptide can modulate type 2 diabetes. In one embodiment, the peptide is an amino acid sequence selected from SEQ ID NOs: 3-9 and 24-30. Another embodiment is a kit for determining the level of Th40 cells, the kit comprising a peptide that interacts with a CD40 protein, and methods for detecting CD40-bound peptide. Kits can also contain associated reagents and components, such as, but not limited to, buffers, labels, containers, inserts, tubing, vials, syringes, and the like.

The following examples are provided for the purposes of illustration and are not intended to limit the scope of the present invention.

EXAMPLES

Example 1

This Example demonstrates the effect of various peptide fragments of CD154 on CD4/CD8 ratios and the development of diabetes in NOD mice.

Figure 2A:
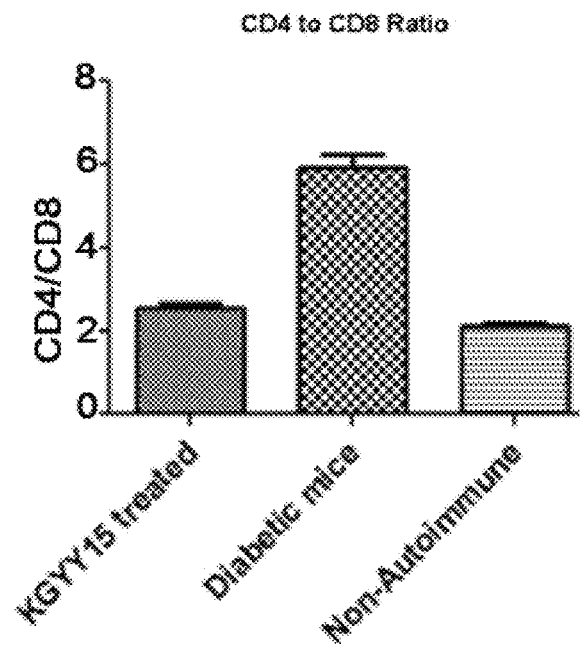
FIG. 2A is a chart of the effect of a 15-mer peptide from CD154 on the CD4/CD8 ratio in NOD mice.

Peptides were designed based on the amino acid sequence of mouse CD154 protein (SEQ ID NO:1) in the SwissPro database. The peptides (8-mer (SEQ ID NO: 5; SEQ ID NO: 6), 10-mer (SEQ ID NO:24), 13-mer (SEQ ID NO:25), 15-mer (SEQ ID NO: 7), 24-mer (SEQ ID NO:26), scrambled (SEQ ID NO: 23), and RGD (arginylglycylaspartic acid) were then ordered from New England Peptide. The RGD peptide is a 15-amino acid sequence from the CD154 sequence that does not include the CD40 binding motif. The lyophilized peptides were suspended in sterile saline at 1 mg/ml. 25 ug in 100 ul (1 mg/kg) of a particular peptide was then injected into the tail vein of 6-week old NOD mice. Control mice received 100 ul of sterile saline. This is well before the onset of diabetes (and atherosclerosis), but after damage to pancreatic islets has begun. Weekly after the initial injection, another 25 ug of peptide (or 100 ul of saline in the case of the Control mice) was injected into the tail vein. At 10 weeks of age, mice were monitored for diabetes, as indicated by a blood glucose level greater than 250 mg/dL for three consecutive days. The results of this study are shown in FIG. 1. During this time, blood was also taken from the tail vein, or by sub-mandibular venal puncture, and the level of CD4+ and CD8+ cells determined by flow cytometry using antibodies for CD4 protein and CD8 protein. The results of this analysis are shown in FIG. 2A.

Figure 2B:
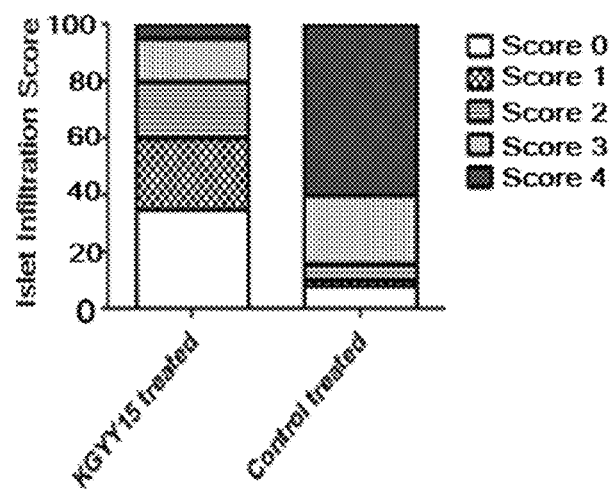
FIG. 2B is a chart of the effect of 15-mer peptide on beta-islet infiltration in treated versus control pancreata excised, examined, and scored.

Pancreata were excised and examined by histology for cellular infiltrates and assigned scores based on observable, measurable, and quantifiable data: 0=no infiltrate; 1=one pole infiltrate; 2=peri-insulitis, bi-polar-infiltrates; 3=75% infiltrate and 4=full infiltration. The results of this analysis are shown in FIG. 2B.

The results demonstrate that treatment with a peptide unrelated to the CD154 protein did not reduce the development of diabetes in NOD mice. In contrast, treatment of mice with a 15-mer peptide derived from the CD154 protein prevented the onset of diabetes. Further, the 13-mer peptides derived from the CD154 protein had significant effects on the development of diabetes. In addition, the data demonstrates that the 15-mer peptide did not result in compromise of the immune system, as determined by the CD4/CD8 ratio.

Example 2

This Example demonstrates the effect of the 15-mer peptide on hyperglycemia in newly diabetic NOD mice.

Six mice from Example 1 that were not treated were allowed to subsequently develop diabetes. These mice were injected intravenously with 100 ug of the 15-mer peptide.

Figure 3:
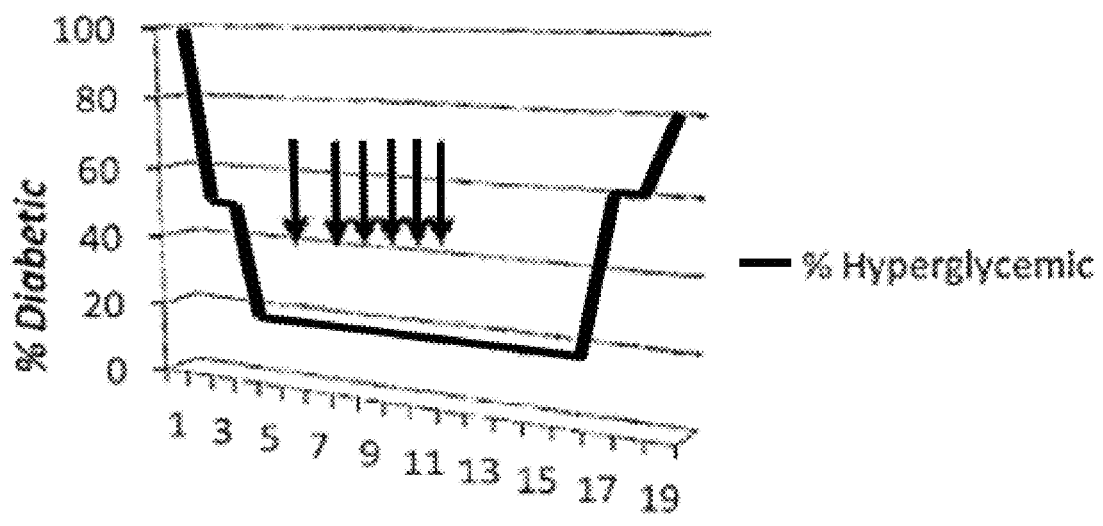
FIG. 3 is a graph of reversal of diabetes in NOD mice using a 15-mer peptide from CD154.

These mice were then given weekly injections of the 15-mer peptide into their tail veins, and their blood glucose levels monitored twice-weekly. The 15-mer peptide was administered for a total of ten weeks, after which the treatment was stopped. The results of this study are shown in FIG. 3.

This study demonstrates that injection of the 15-mer peptide into already diabetic mice can reverse hyperglycemia. It also demonstrates that cessation of the treatment results in return of hyperglycemia within 5 weeks.

Example 3

This study demonstrates the ability of the 15-mer peptide to bind to Th40 cell and B cells.

Figure 4:
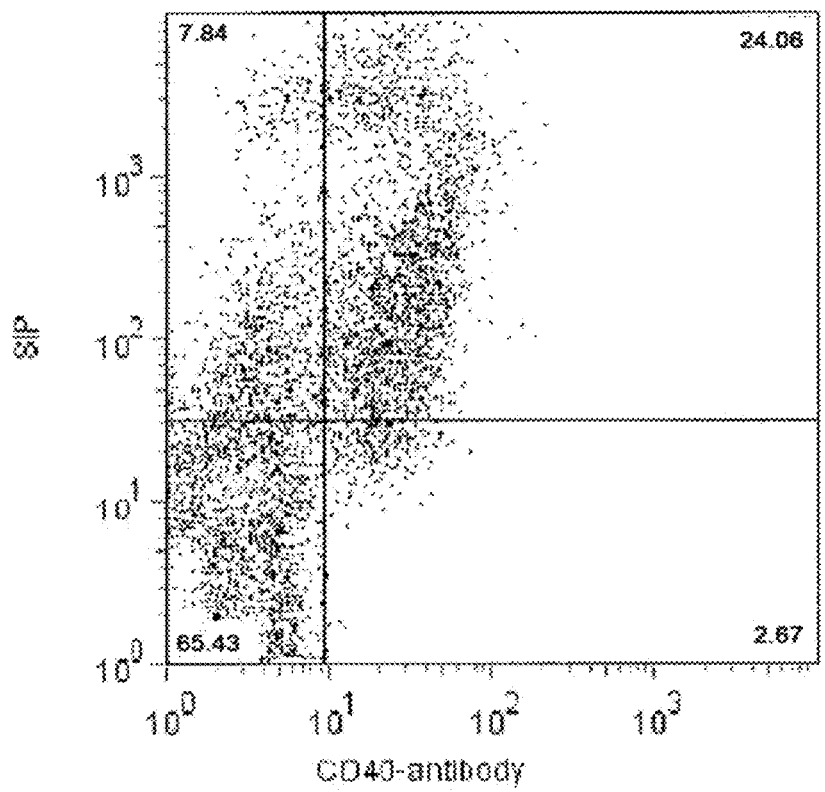
FIG. 4 is a dot-plot of the detection of Th40 cells using a SIP-15-mer peptide from CD154.

Total lymphocytes were isolated from 9 week old NOD mice. The lymphocytes were incubated with anti-CD4, anti-CD8, anti-CD40 and an FITC-labeled 15-mer peptide, and then analyzed by flow cytometry. Cells were gated for CD4 (both CD4hi and CD4lo populations were included) and CD40 versus the 15-mer peptide. The results of this analysis are shown in FIG. 4.

Figure 5:
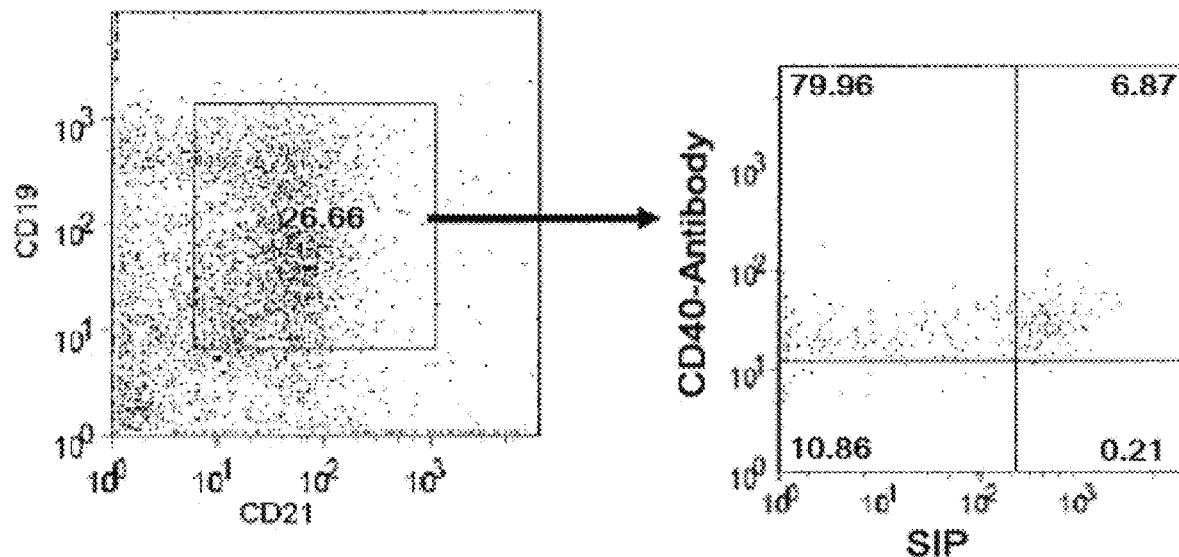
FIG. 5 is a dot-plot of a screening of B cells using a SIP-15-mer peptide from CD154.

B cells were isolated from the spleens of NOD mice. Sorted MHC-II+ cells were purified from total lymphocytes. Cells were stained with FITC-labeled 15 mer peptide, anti-CD40, and B cell markers CD19 and CD21. MHC-II+ cells were gated for CD19+ and CD21+ and then 15-mer peptide versus CD40 antibody was measured. The results of this study are shown in FIG. 5.

This study shows that a substantial majority, 90% of CD40+ T-cells, also bind the 15-mer peptide, thereby demonstrating that the 15-mer peptide is highly specific for CD40+ cells. It also shows that while 90% of B cells were CD40 positive, only 8% of B cells bound the 15-mer peptide.

Example 4

This example demonstrates the level of CD40 positive cells in the blood of type-I diabetic subjects and non-diabetic (control) subjects.

Figure 6:
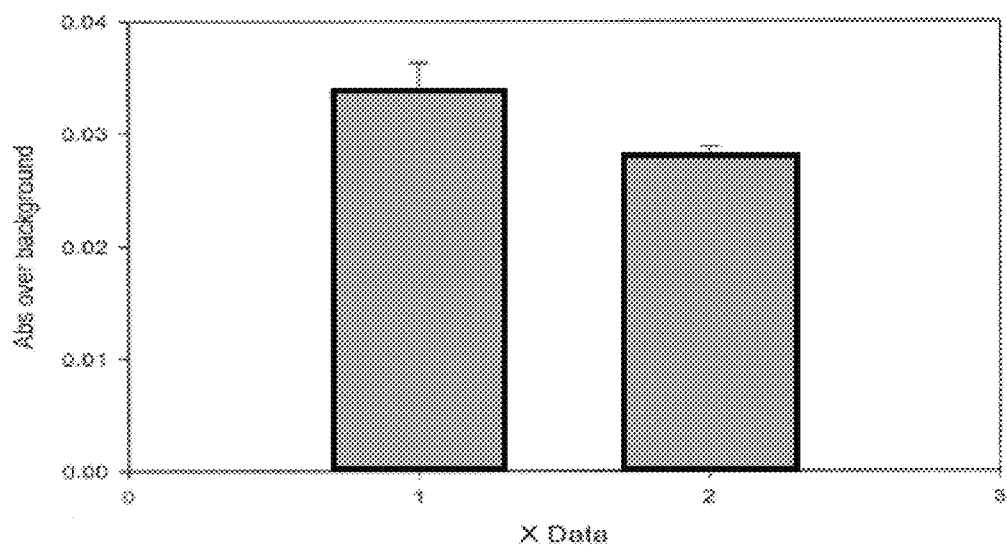
FIG. 6 is a chart demonstrating a comparison of Th40 cell levels in diabetic and non-diabetic mice.

1 ml of whole blood was obtained from each individual and incubated with biotin-conjugated, 15-mer peptide. The cells were then exposed to horseradish peroxidase (HRP)-avidin, washed and the absorbance at 405 nm determined using a spectrophotometer. The results of this study are shown in FIG. 6.

This study demonstrates that blood cells from patients having type-I diabetes had higher 15-mer peptide binding activity than cells from non-diabetic controls.

Example 5

This example demonstrates the level of insulin granulation observed in the pancreas of NOD mice treated with either the 15-mer peptide or a peptide from ovalbumin.

Figure 7:
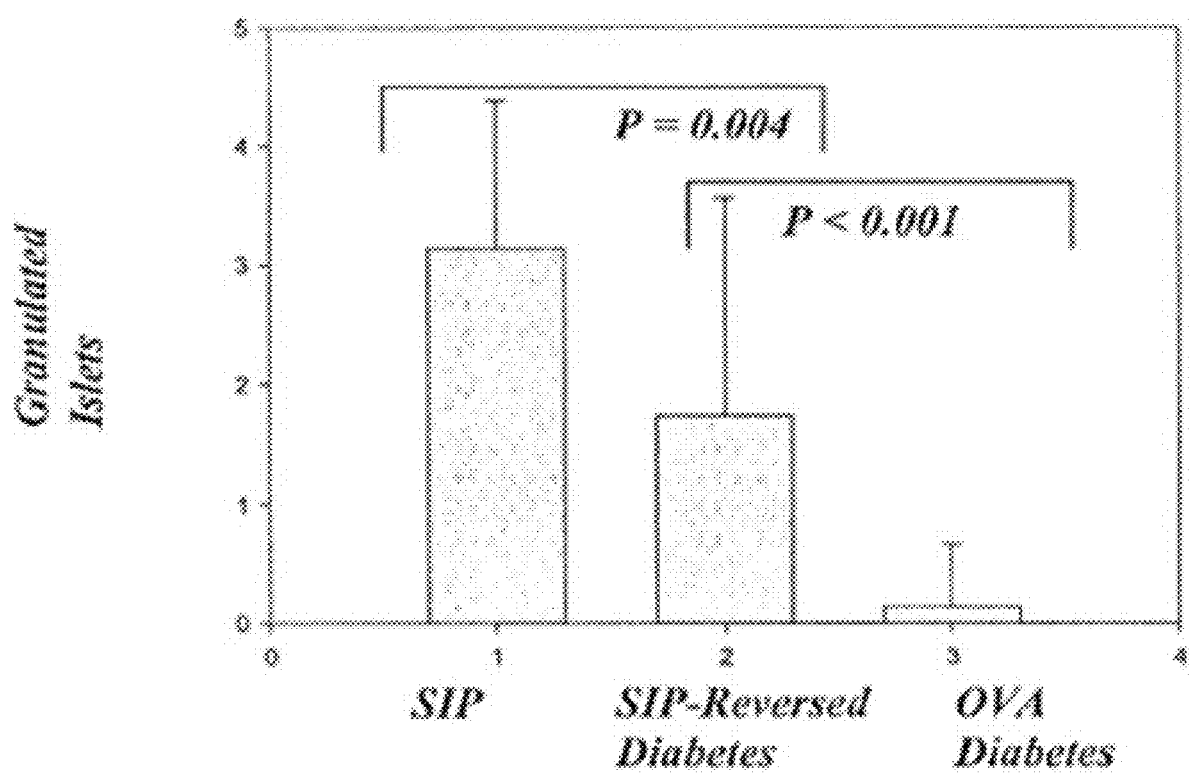
FIG. 7 is a chart demonstrating the effect of treatment with the 15-mer peptide on insulin granulation of the pancreas.

At the onset of diabetes, six NOD mice were injected with 100 ug/ml of the 15-mer peptide, resulting in the reversal of hyperglycemia in 80% of the recipients. Six weeks after reversal of hyperglycemia, mice were sacrificed, and the pancreas removed for analysis. The pancreas was fixed, sectioned and then stained using an aldehyde/fuschsin stain that allows detection of insulin granules. Granulation of the tissue was scored as follows: 4=completely granulated; 3=75% of islet granulated; 2=50% of islet granulated, and peri-insulitis; 1=25% of islet granulated; 0=no insulin granules detected. The results of this analysis are shown in FIG. 7.

This analysis demonstrates that the 15-mer peptide preserved insulin granules in the majority of the mice, and was significantly improved in peptide-reversed diabetic mice compared to diabetic mice that received an irrelevant peptide.

Example 6

Figure 8:
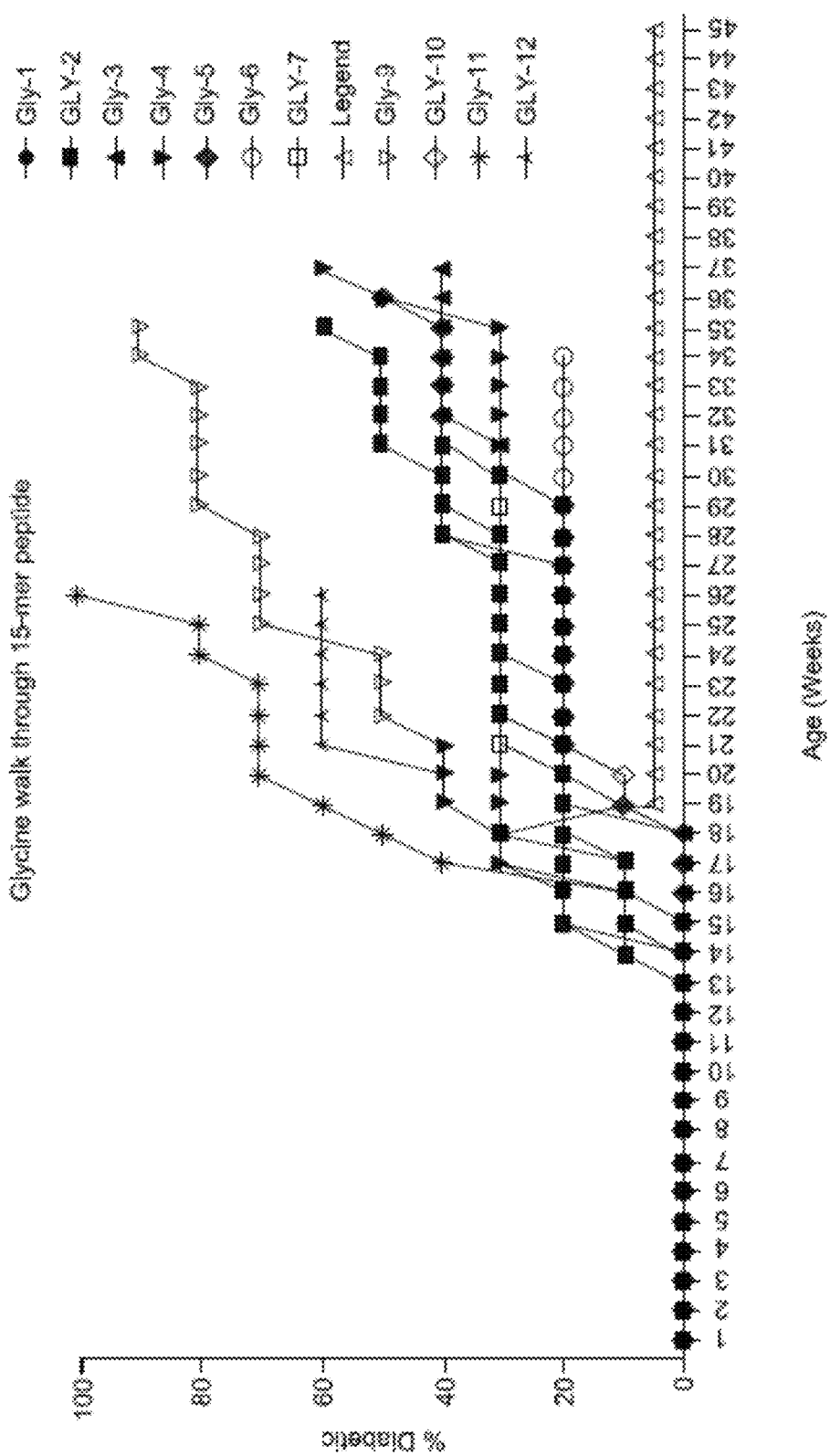
FIG. 8 is a graph that shows the effect of mutations in the 15-mer peptide on the ability of the 15-mer peptide to inhibit development of diabetes in NOD mice.

This example demonstrates the effect of mutations in the 15-mer peptide on its ability to prevent the onset of diabetes. FIG. 8 provides results related to this Example 6.

Peptide were designed and produced as described in Example 1. Variant peptides were produced so that in each variant, a glycine was substituted for an amino acid corresponding to an amino acid in positions 1-7 or 9-12 of SEQ ID NO:7, as follows: Gly-1 G-L-Q-W-A-K-K-G-Y-Y-T-M-K-S-N(SEQ ID NO:11)

```
Gly-1
                                  (SEQ ID NO: 11)
G-L-Q-W-A-K-K-G-Y-Y-T-M-K-S-N

Gly-2
                                  (SEQ ID NO: 12)
V-G-Q-W-A-K-K-G-Y-Y-T-M-K-S-N

Gly-3
                                  (SEQ ID NO: 13)
V-L-G-W-A-K-K-G-Y-Y-T-M-K-S-N

Gly-4
                                  (SEQ ID NO: 14)
V-L-Q-G-A-K-K-G-Y-Y-T-M-K-S-N

Gly-5
                                  (SEQ ID N0: 15)
V-L-Q-W-G-K-K-G-Y-Y-T-M-K-S-N

Gly-6
                                  (SEQ ID NO: 16)
V-L-Q-W-A-G-K-G-Y-Y-T-M-K-S-N

Gly-7
                                  (SEQ ID NO: 17)
V-L-Q-W-A-K-G-G-Y-Y-T-M-K-S-N

Gly-9
                                  (SEQ ID NO: 18)
V-L-Q-W-A-K-K-G-G-Y-T-M-K-S-N

Gly-10
                                  (SEQ ID NO: 19)
V-L-Q-W-A-K-K-G-Y-G-T-M-K-S-N

Gly-11
                                  (SEQ ID NO: 20)
V-L-Q-W-A-K-K-G-Y-Y-G-M-K-S-N

Gly-12
                                  (SEQ ID NO: 21)
V-L-Q-W-A-K-K-G-Y-Y-T-G-K-S-N
```

NOD mice were placed in groups of 10, and the mice in each group injected IV weekly with 25 ug of either wild-type (WT; Legend) peptide or a variant peptide (in PBS, ph 7.2) listed above. The development of diabetes was monitored by measuring blood glucose levels on a weekly basis. Mice were considered "diabetic" when blood glucose was 250 mg/dl or greater for 3 consecutive readings. Injections began at 6 weeks of age=pre-diabetes.

This example demonstrates that substitution of a glycine at any of positions 1-7, or 9-12, reduces the ability of the 15-mer peptide to inhibit the development of diabetes. It also shows that such mutations do not completely abolish the ability of the mutated 15-mer peptide to inhibit the development of diabetes. Substitutions at the Tyr position 9, Thr position 11, and Met position 12 proved differential for hyperglycemic prevention activity, as shown in FIG. 8. Therefore it is also postulated that a second 6-mer derivative-SEQ ID NO:27-6-mer (Form 2), SEQ ID NO:28-6-mer (Form 3), SEQ ID NO:29-6-mer (Form 4), and SEQ ID NO:30-6-mer (Form 5) may also provide increased therapeutic efficacy.

Example 7

This example demonstrates that the same elevation of Th40 cell levels in the ApoE deficient mouse model of atherosclerosis is also notably elevated in human Type 1 Diabetes (T1D).

Figure 9:
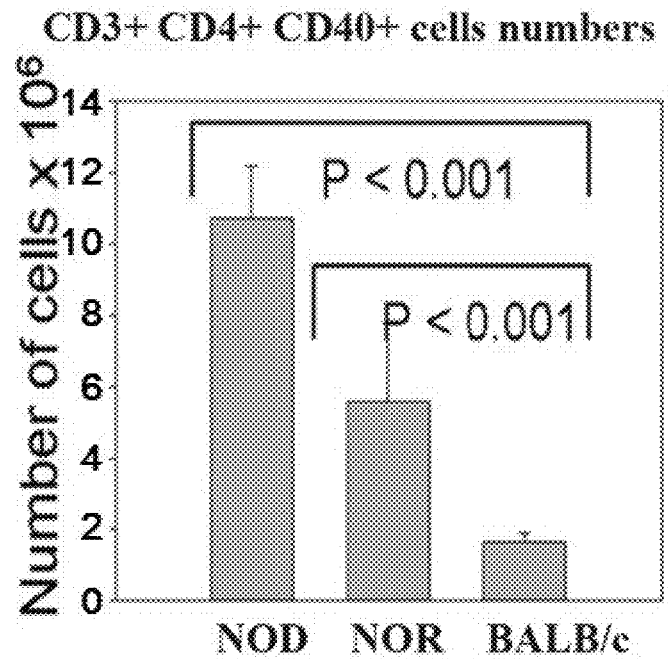
FIG. 9 is a chart showing the number of cells ($\times 10^6$) of CD3+CD4+CD40+ in different mice models.

The peripheral blood was measured was measured for total count of CD3+CD4+CD40+ cell numbers in NOD, NOR (non-obese diabetic resistant), and BALB/c (control) mice as in FIG. 9. This was compared to the percentage of Th40 cells in peripheral blood in human subjects for control, diabetic/new onset, and long term diabetic populations as in FIG. 10. Further, lymphocytes were isolated from 9-week old NOD mice. The lymphocytes were incubated with anti-CD, anti-CD8, and an FITC-labeled 15-mer peptide, and then analyzed by flow cytometry. Cells were gated for CD4 (both CD4hi and CD4lo populations were included) and CD4 versus the 15-mer peptide. These results are displayed in FIG. 11.

ApoE deficient mice on a normal chow diet were selected to receive a dose of 1 mg/kg of the 15-mer peptide (SEQ ID NO: 7) by IV tail injection, three times a week over a period of 26 weeks, beginning at 9 weeks of age and also utilized a control. At 25 weeks, the animals were euthanized, weighed, and then had blood, spleen, and pancreas removed for analysis. The subjects were then perfused through cardiac puncture with 4% paraformaldehyde. Aortic arches were dissected, dehydrated in sucrose gradient and then flash frozen. Approximately thirty-five 8 um longitudinal sections were obtained per mouse for various staining procedures. Flow cytometry was performed utilizing a MACSQuant® Analyzer 10 (Miltenyi Biotec Inc.). Additional analysis was performed using FlowJo® (FlowJo, LLC wholly owned by BectonDickinson, Inc.) single-cell flow cytometry software.

Figure 12:
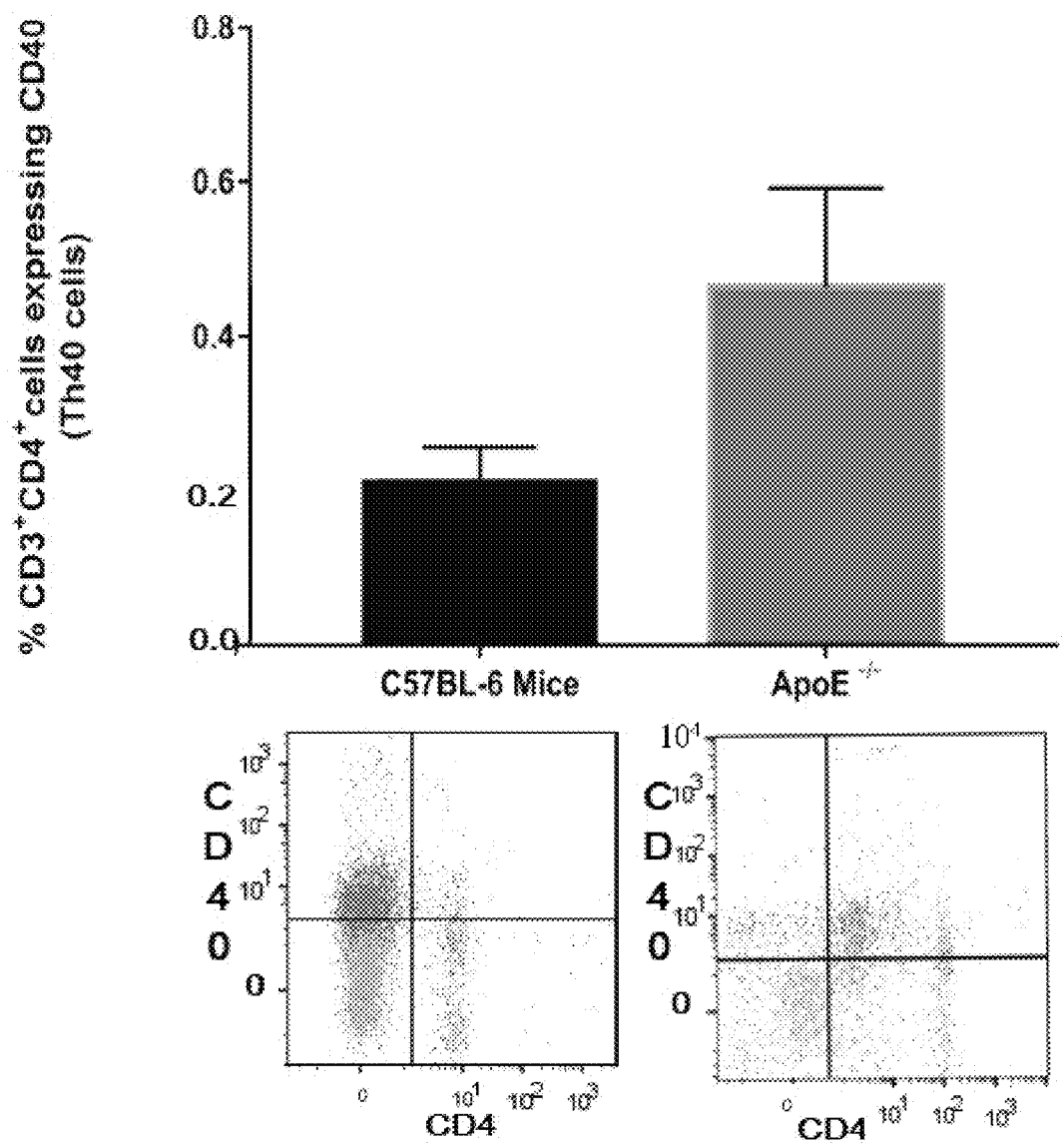
FIG. 12 is a chart showing the percentage of Th40 cells of CD3+CD4+ population of mice models.

C57BL/6 and ApoE-/- mice demonstrated increased levels of Th40 cells relative to all CD3+CD4+ cells prior to hyperglycemia as demonstrated in FIG. 12.

Figure 13:
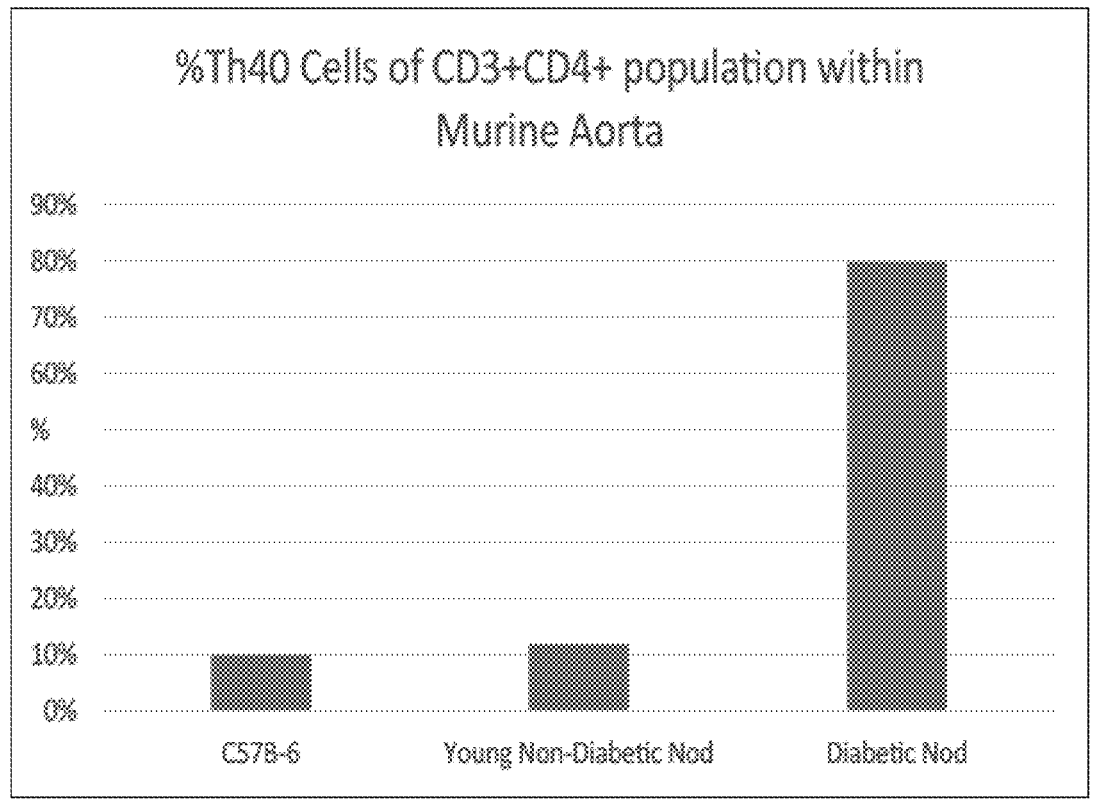
FIG. 13 is a chart that shows Th40 Cell percentage of CD3+CD4+ population within the murine aorta of C57B-6, young non-diabetic NOD mice, and diabetic NOD mice.

Further, NOD mice tested in this study demonstrated significant Th40 infiltration in the aorta compared with control and young non-diabetic NOD mice populations, as shown in FIG. 13.

Figure 10:
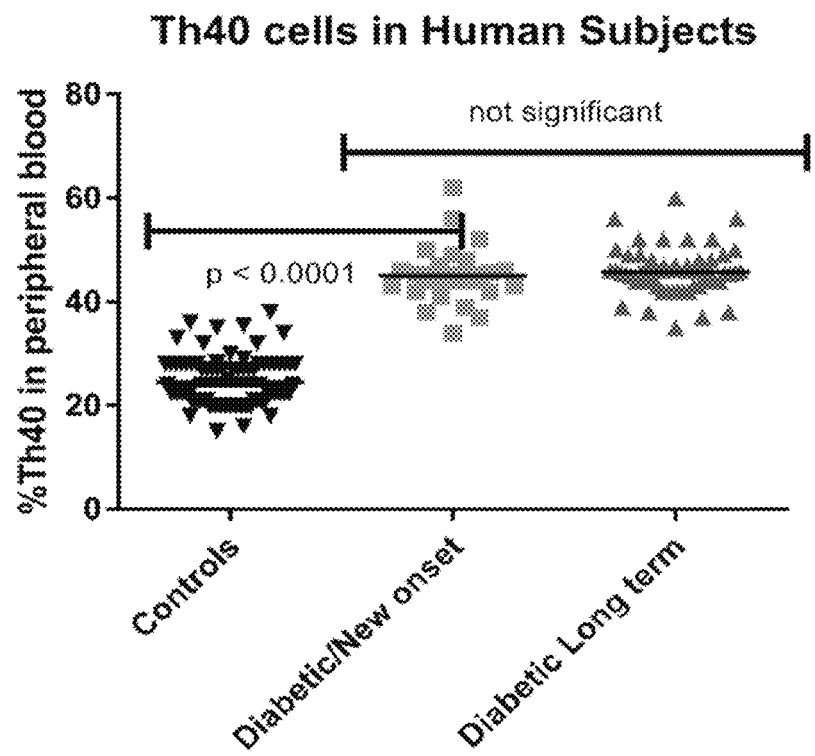
FIG. 10 is a chart showing the percentage of Th40 cells in the peripheral blood in human subjects in control and diabetic subjects.
Figure 11:
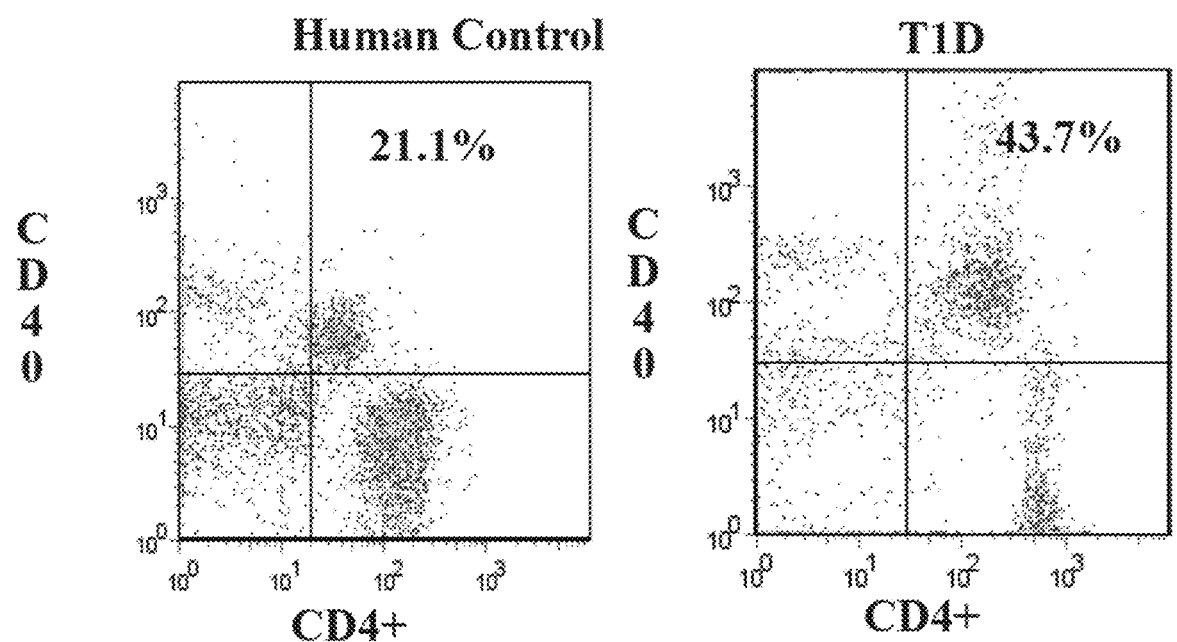
FIG. 11 is a dot-plot comparing CD4+ and CD40 cell data obtained through flow cytometry. Th40 cells (CD4+CD40+) are in the upper right quadrant.
Figure 14:
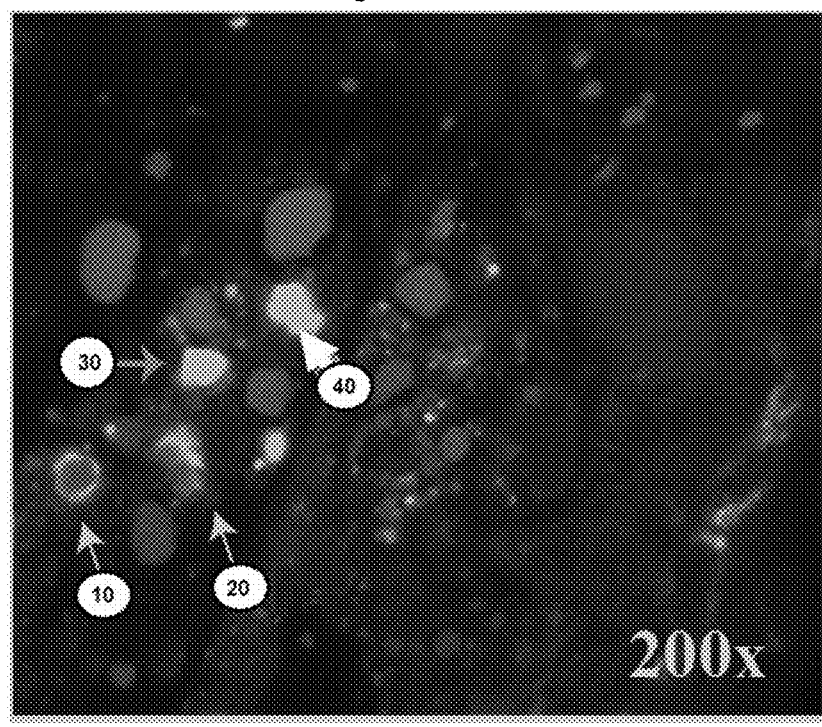
FIG. 14 is an image at 200× magnification showing Th40 cells in the shoulder region of plaque in the ApoE−/− mouse model.
Figure 15:
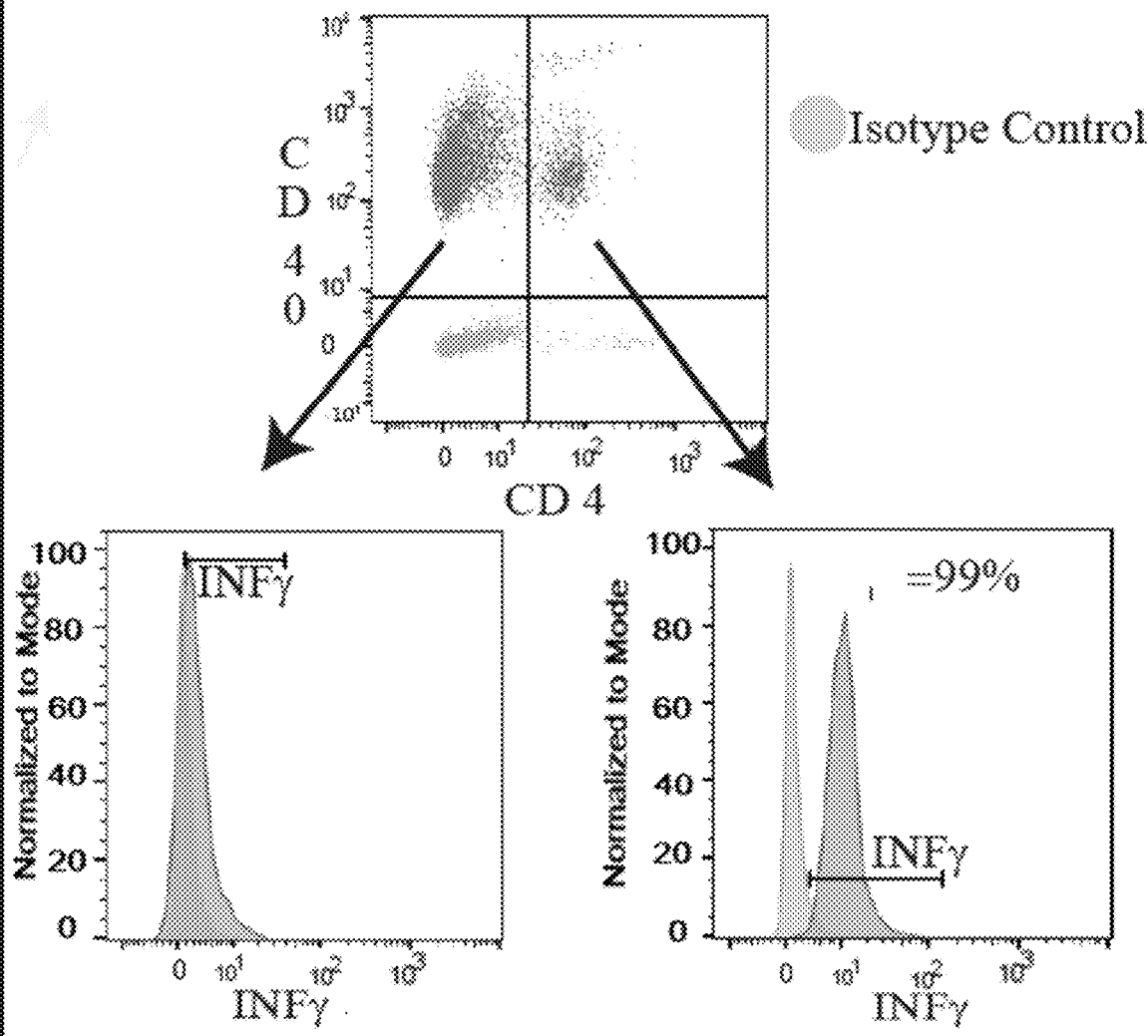
FIG. 15 is a graph of interferon gamma control of Th40 proliferation.
Figure 20:
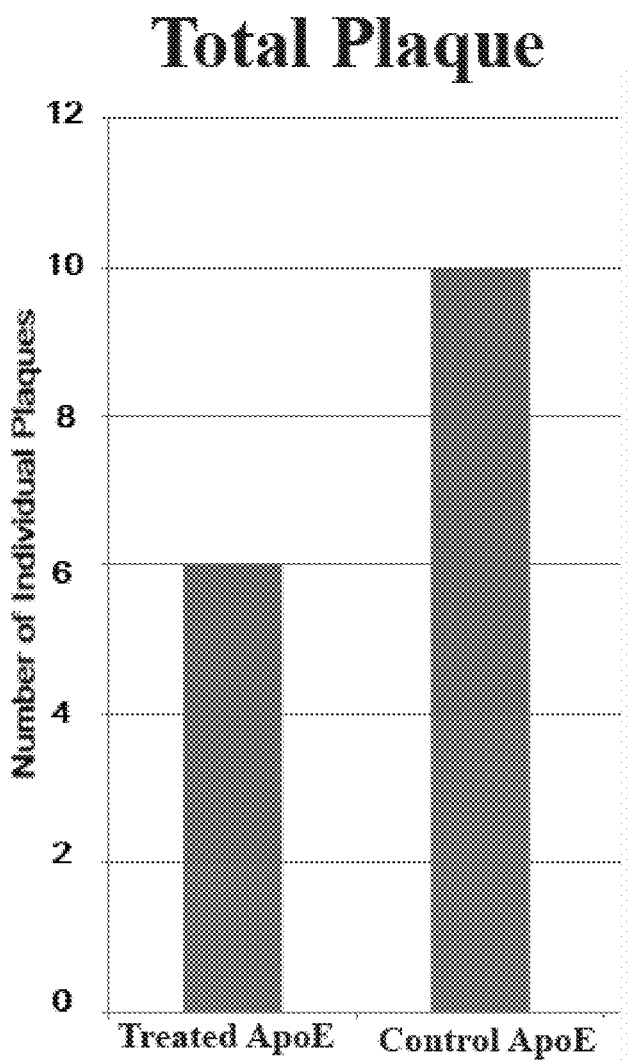
FIG. 20-23 are charts of treated and control ApoE mice subjects.

An exemplar aortic plaque of one of the longitudinal sections was observed at 200x magnification using oil-red-0, trichrome stain and immune-fluorescence, and is shown in FIG. 14. This microscopy and stain of the aorta showed that not only are the Th40 cells increased in the aorta similarly to the peripheral blood as demonstrated in FIGS. 10-14, but also the Th40 cells are found within the shoulder region of plaque in the ApoE-/- model (the growth region of plaque/atherosclerosis). In FIGS. 14, 10 and 20 identify cells that represent CD3+, CD4+, and CD4 (+(Th40 cells) that have significant intracellular CD40, 30 demonstrates Th40 cell with extracellular expression and no demonstrative CD40 intracellularly. 40 identifies CD3+, CD4+, CD40neg cell.

Example 8

This example demonstrates that CD3+CD4+CD40+ cells appear to produce interferon gamma (INFγ) in abundance. Additionally, interferon gamma controls Th40 proliferation.

ApoE deficient mice on a normal chow diet were selected to receive a dose of 1 mg/kg of the 15-mer peptide (SEQ ID NO: 7) by IV tail injection, three times a week over a period of 26 weeks, beginning at 9 weeks of age and also utilized a control. At 25 weeks, the animals were euthanized, weighed, and then had blood, spleen, and pancreas removed for analysis. The subjects were then perfused through cardiac puncture with 4% paraformaldehyde. Aortic arches were dissected, dehydrated in sucrose gradient and then flash frozen. Approximately thirty-five 8 m longitudinal sections were obtained per mouse for various staining procedures. Flow cytometry was performed utilizing a MACSQuant® Analyzer 10 (Miltenyi Biotec Inc.). Additional analysis was performed using FlowJo® (FlowJo, LLC wholly owned by BectonDickinson, Inc.) single-cell flow cytometry software.

As demonstrated in FIG. 14 through confocal microscopy, CD40 can be internal or external to the CD3+CD4+ cell. Flow cytometry was further performed and demonstrated that while most CD3+ cells appear to have ability to produce CD40, the CD3+CD4+CD40+ cells appear to produce interferon gamma (IFNγ) in abundance. This flow cytometry study incorporated both the external and internal staining of CD3, CD4, CD40, and IFNγ.

Figure 16:
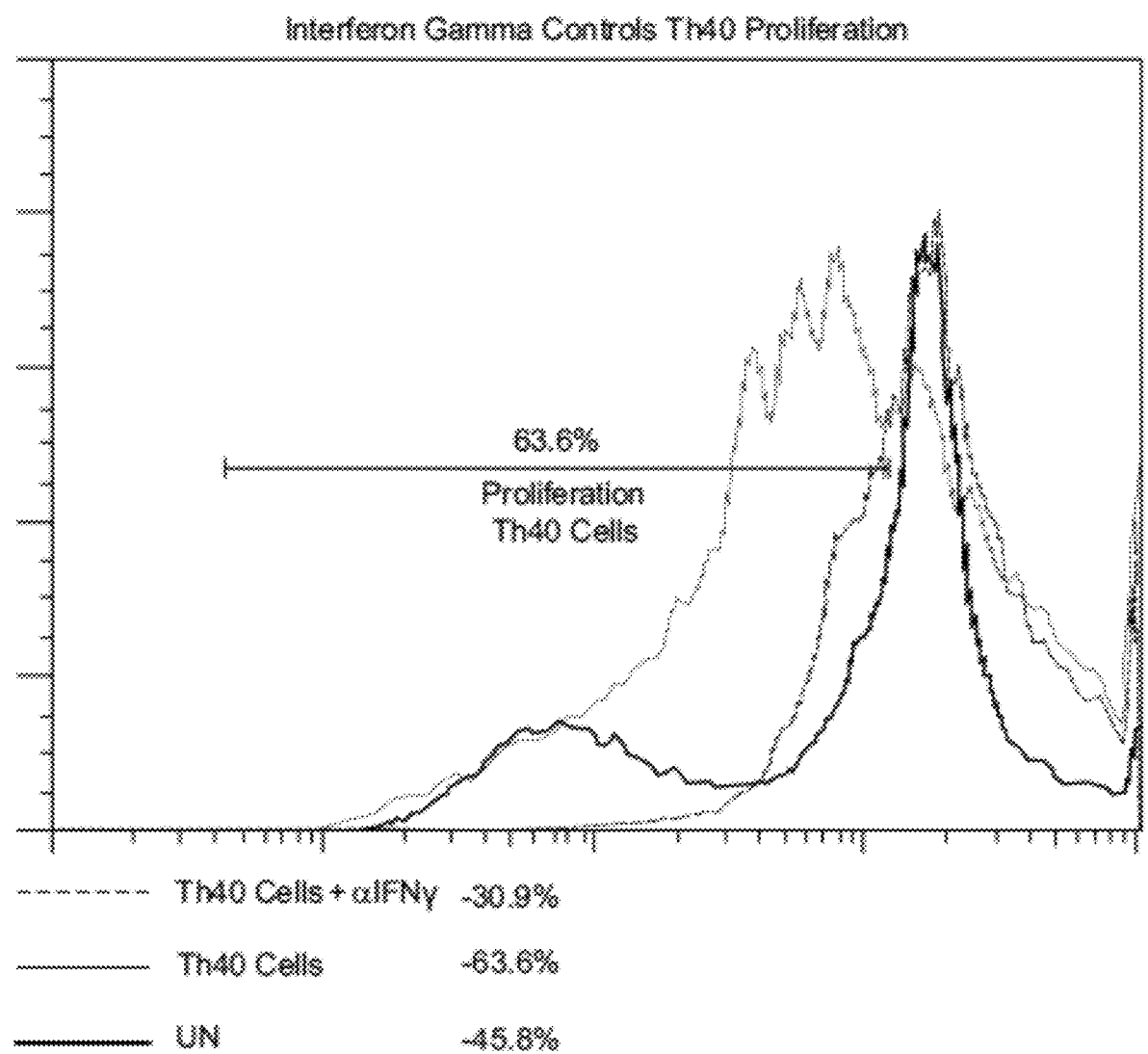
FIG. 16 is a plot of CD40 stimulated proliferation of Th40 cells in the absence/presence of anti-interferon gamma antibody (αIFNγ) demonstrating that interferon gamma mediates CD40 induced proliferation.

FIG. 16 demonstrates that interferon gamma controls Th40 proliferation. Isolated Th40 cells were cross-linked by antibody to CD40. The graph in FIG. 16 denotes proliferation of CD40 stimulated (CD40XL: activated) Th40 cells in the absence/presence of antibody to INFγ (αIFNγ) and non-stimulated controls (UN). Additionally, by blocking IFNγ, activated Th40 cells do not proliferate.

Example 9

This example demonstrates that $KGYY_{15}$ (15-mer-SEQ ID NO:7) and $KGYY_6$ (6-mer-SEQ ID NO:29) abrogates atherosclerosis.

ApoE deficient mice on a normal chow diet were selected to receive a dose of 1 mg/kg of the 15-mer peptide (SEQ ID NO: 7) by IV tail injection, three times a week over a period of 26 weeks, beginning at 9 weeks of age and also utilized a control. At 25 weeks, the animals were euthanized, weighed, and then had blood, spleen, and pancreas removed for analysis. The subjects were then perfused through cardiac puncture with 4% paraformaldehyde. Aortic arches were dissected, dehydrated in sucrose gradient and then flash frozen.

Figure 17:
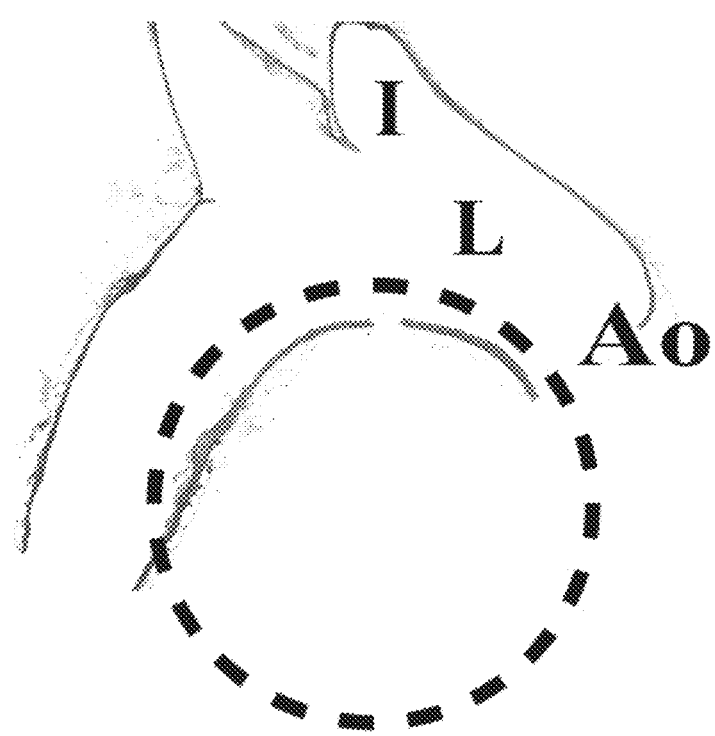
FIG. 17 is a sample of stains of aortic arch of the lesser curvature of the aortic arch.

FIG. 17 provides an example of the lesser curvature of the aortic arch, defined proximally from the aortic outflow (AO). Of the segments seen in the trichrome stain, an intimal distance of 2.4 mm was measured distally. The aortic-arch wall area subtended by this 2.5 mm stretch of the intima was calculated for each section of all mice, with maximal area of the inner-aortic-arch wall of each mouse used to compute averages per group. The luminal surface (L), aortic arch (AO), and innominate artery (I) are labelled in this FIG. 17.

Figure 18:
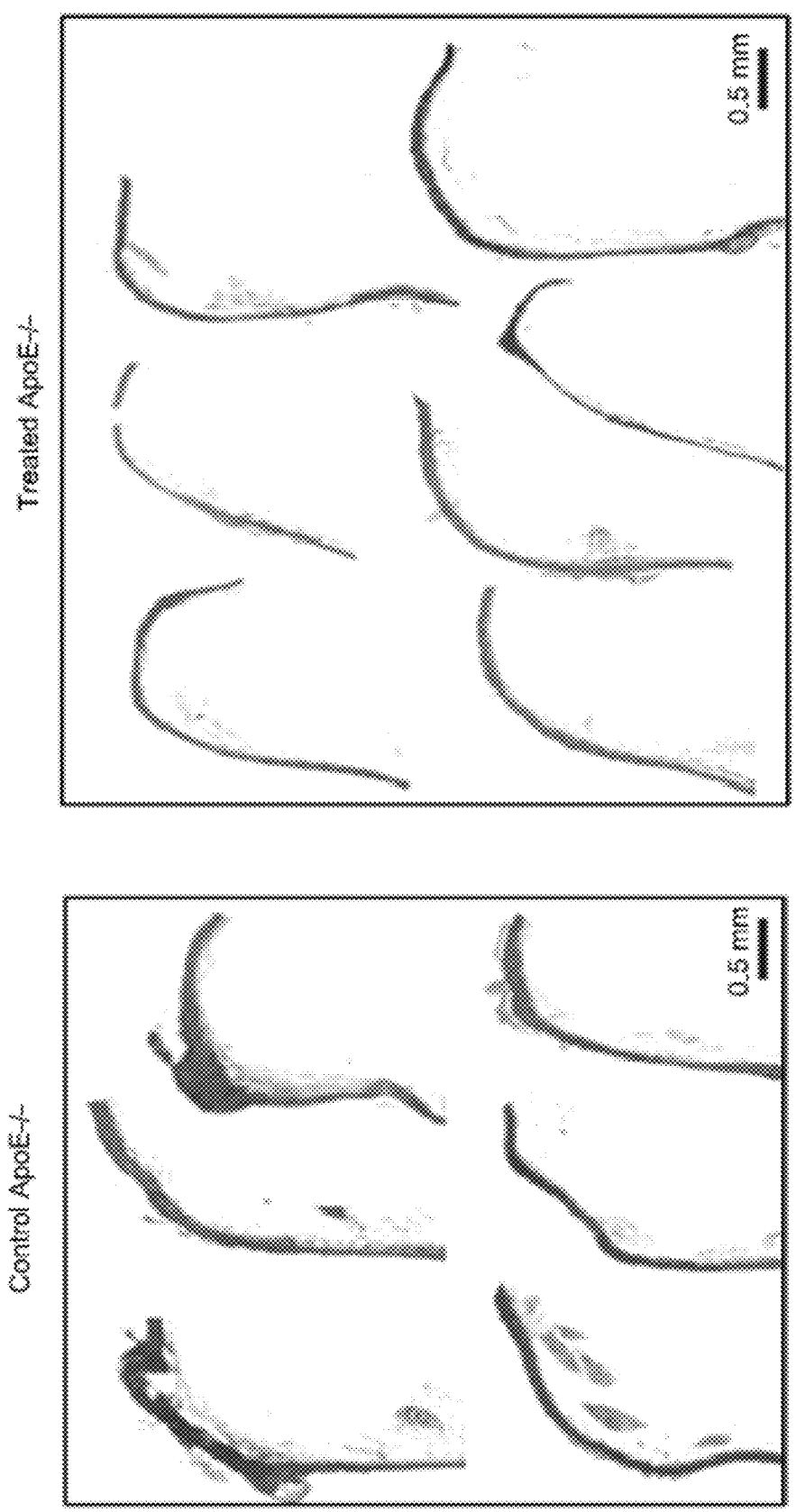
FIG. 18 is a stain of lesser curvature of aortic arch in control and treated subjects.

FIG. 18 demonstrates the lesser curvature of the aortic arch of the control ApoE mice compared to the lesser curvature of the aortic arch of mice treated with the 15-mer peptide, in accordance with the steps outlined in this example.

Figure 19:
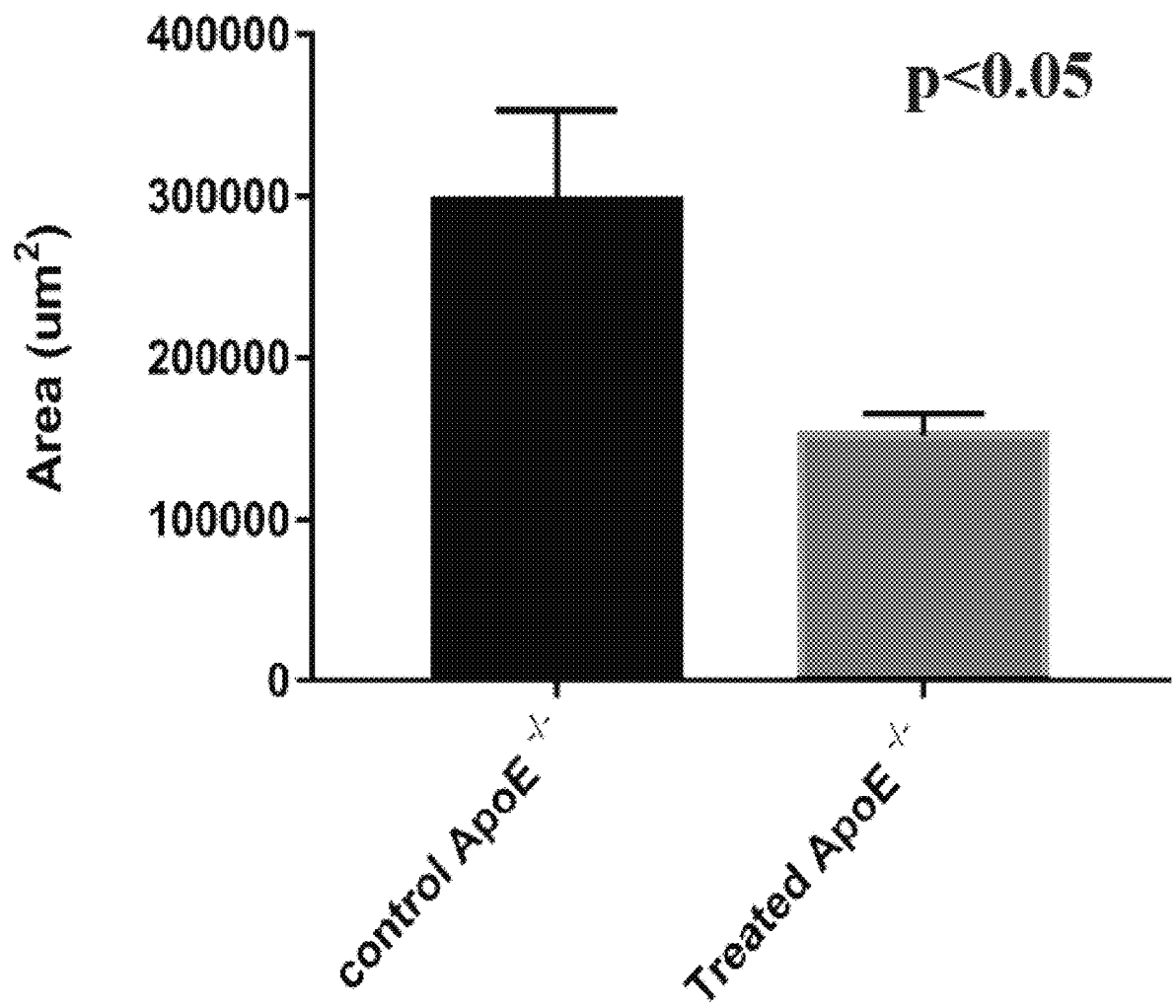
FIG. 19 is a chart of area measurements of the lesser curvature of aortic arches and plaques.

FIG. 19 demonstrates the reduction of the total area achieved by peptide treatment. The total area of the 2.5 mm segment (as described in FIG. 17) was substantially reduced.

FIG. 20 demonstrates the reduction of number of plaque, including early lesions and advanced plaque. The total number of plaque was significantly decreased in the treatment group.

Plaque was subdivided based on morphology of early lesions (observable as fatty streaks containing macrophage derived foam cells with varying degrees of lipid accumulation) compared with more advanced fibroatheromas (containing varying degrees of lipid or necrotic core and fibrous caps). All plaque within the designated 2.5 mm segment were included. Both the total number and type of plaque were significantly decreased in those subjects treated with the peptide.

This study demonstrates that administration of the peptide abrogates atherosclerosis.

Example 10

This example demonstrates administration of the $KGYY_{15}$ (15-mer-SEQ ID NO:7) augments cap formation while reducing advancement of existing disease.

In this study, six ApoE-/- mice received a normal chow diet from 0 to 20 weeks of age. At 20 weeks of age, three mice were randomly assigned to receive dose of 1 mg/kg of $KGYY_{15}$ (15-mer-SEQ ID NO:7) by IV tail injection, once a week for a period of 4 weeks. Control mice received vehicle only. After 4 weeks of treatment, animals were euthanized then perfused through cardiac puncture with 4% paraformaldehyde. Aortic arches were dissected in surcrose gradient and flash frozen. Approximately fifty, 8 um longitudinal sections were obtained per mouse. Slides were treated with trichrome stain and analyzed using cellSens software for measurements. Total plaque was measured including 2.5 mm lesser curvature and innominate artery.

FIG. 20 shows the number of individual early plaques and advanced plaques were reduced in the treated subjects compared to the control subjects.

Figure 21:
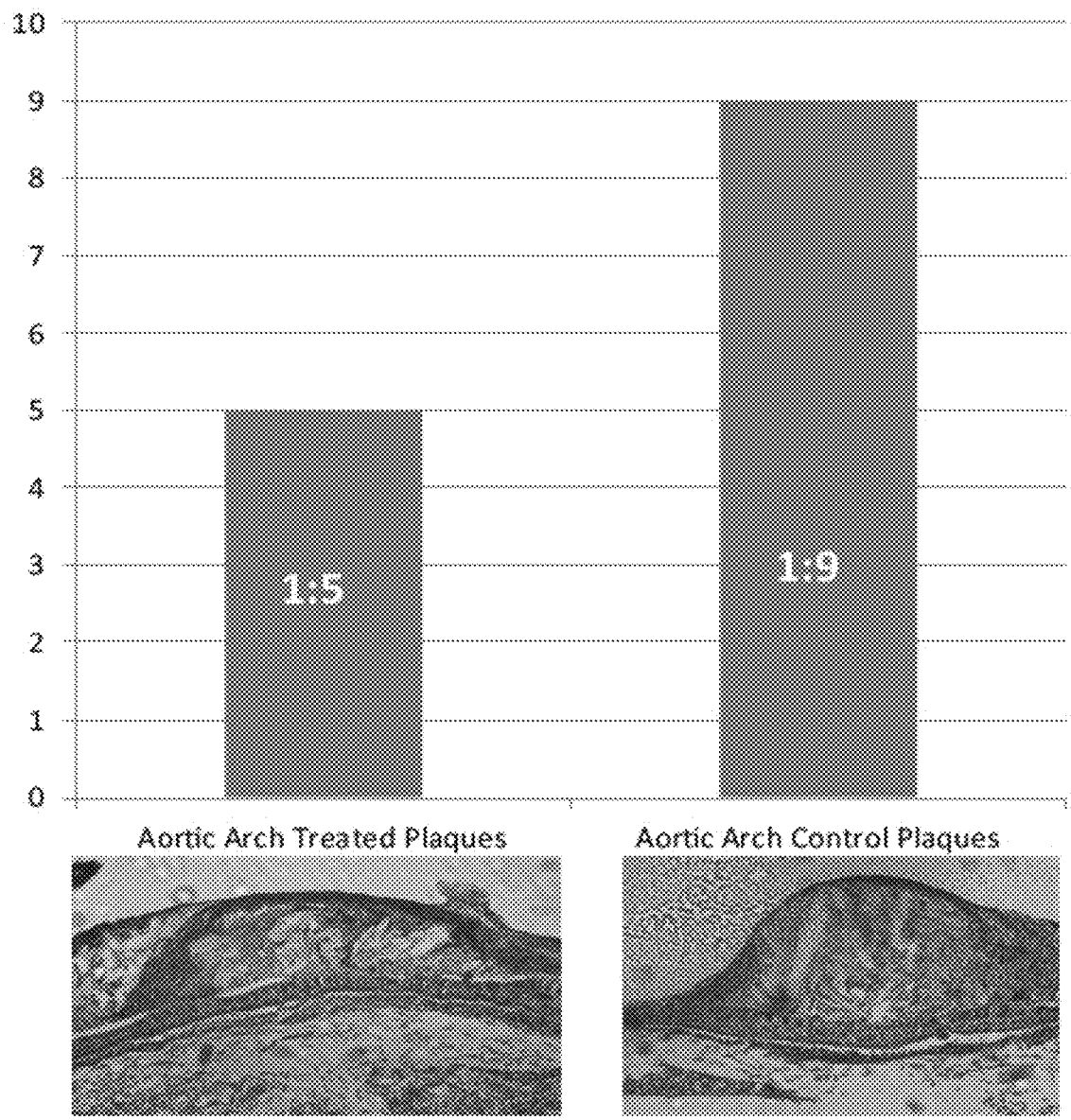

FIG. 21 shows that the cap to core ratio of advanced plaques was reduced in the treated subjects compared to the control subjects.

Figure 22:
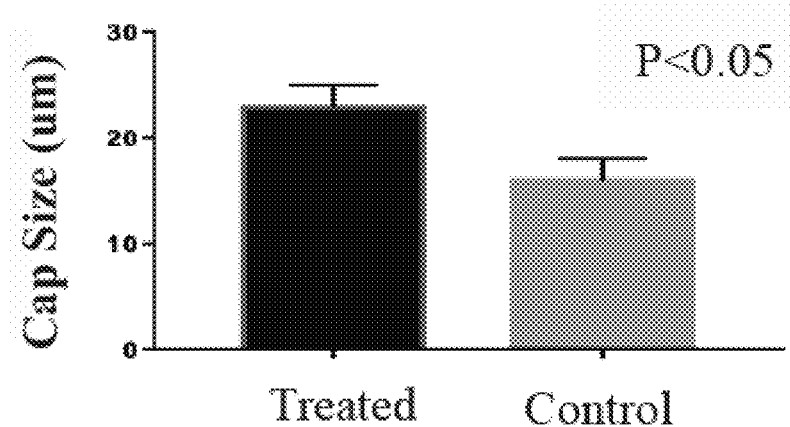

FIG. 22 shows the average cap width (cap size) was greater in the treated subjects compared to the control subjects.

Figure 23:
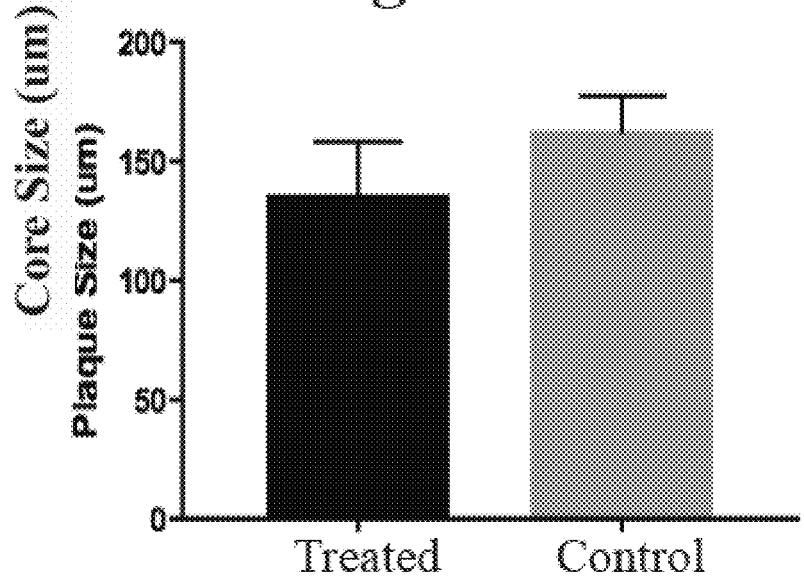

FIG. 23 shows the average core width (core size/plaque size) was decreased in the subjects treated with the peptide compared to the control subjects.

This example demonstrates that administration of the $KGYY_{15}$ (15-mer-SEQ ID NO:7) augments cap formation while reducing advancement of existing disease. Moreover, this study further demonstrates that administration of the $KGYY_{15}$ peptide trends toward results of plaque stability.

From the foregoing, it is readily apparent that T1D shares with atherosclerosis the CD40-CD154 dyad which drives autoimmune inflammation. There are increased Th40 cell levels in peripheral blood of NOD mice, human T1D patients, and ApoE-/- mice. Th40 cells infiltrate the aortic wall and are found within the plaque of ApoE-/- mice. Th40 cells produce the inflammatory cytokine IFNγ at a level greater than that of other cells and this drives inflammation. The $KGYY_{15}$ peptide targets Th40 cells. The specified peptide furthermore abrogates and modulates atherosclerosis which may be due to Th40 blockade or general blockade of CD40. Moreover, the administration of the specified peptide trends toward more stable plaque types.

Example 11

Whole human blood was administered the peptide in accordance with similar dosing levels to those used for murine studies.

FIG. 24 provides the results of clot studies observed in humans.

This study demonstrates that the KGYY v; peptide when administered to humans does not modify or change the clotting of whole human blood significantly outside of normally recognized levels.

Example 12

This example demonstrates that ApoE mice that have been genetically modified to obtain atherosclerosis and fed a high fat diet and treated with the 6-mer peptide may have the levels of LDL cholesterol values decreased compared to untreated subjects.

In this study, six ApoE-/- mice received a normal chow diet from 0 to 20 weeks of age. At 20 weeks of age, three mice were randomly assigned to receive dose of 1 mg/kg of $KGYY_6$ (6-mer-SEQ ID NO:29) by IV tail injection, once a week for a period of 4 weeks. Control mice received vehicle only.

Figure 27:
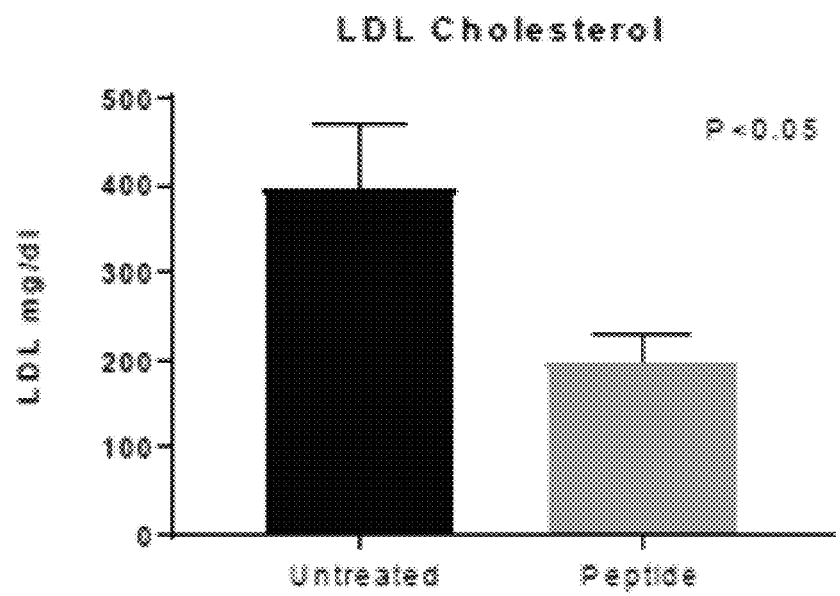
FIG. 27 is a graph of LDL cholesterol measured in treated and untreated subjects.

Data obtained from untreated mice and compared to those in treated mice showed statistically significant reduction (>50%) in LDL cholesterol values. This data is provided in FIG. 27.

Example 13

Figures 28A, 28B:
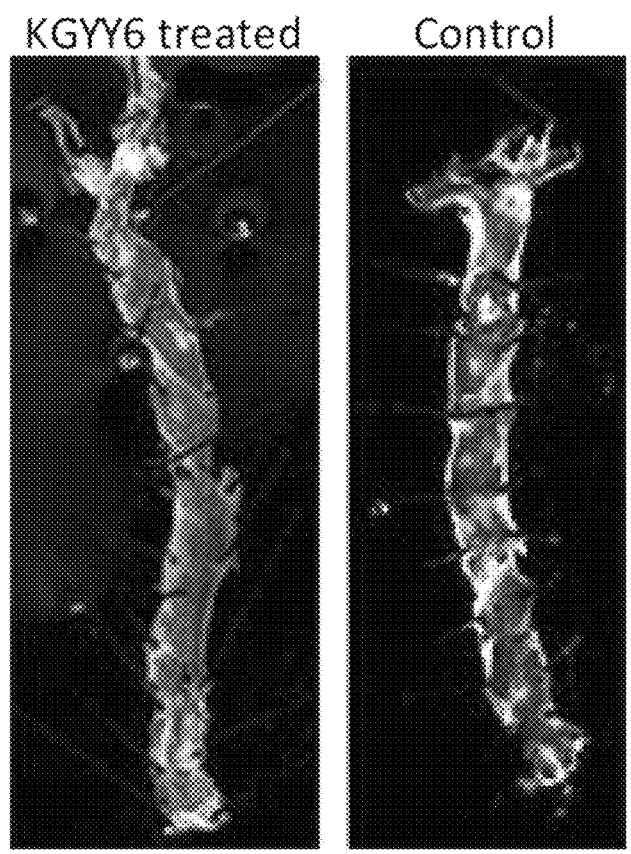
FIG. 28A is an image of KGYY6 treated aortic en-face Sudan IV staining.
FIG. 28B is an image of control aortic en-face Sudan IV staining.
Figure 29:
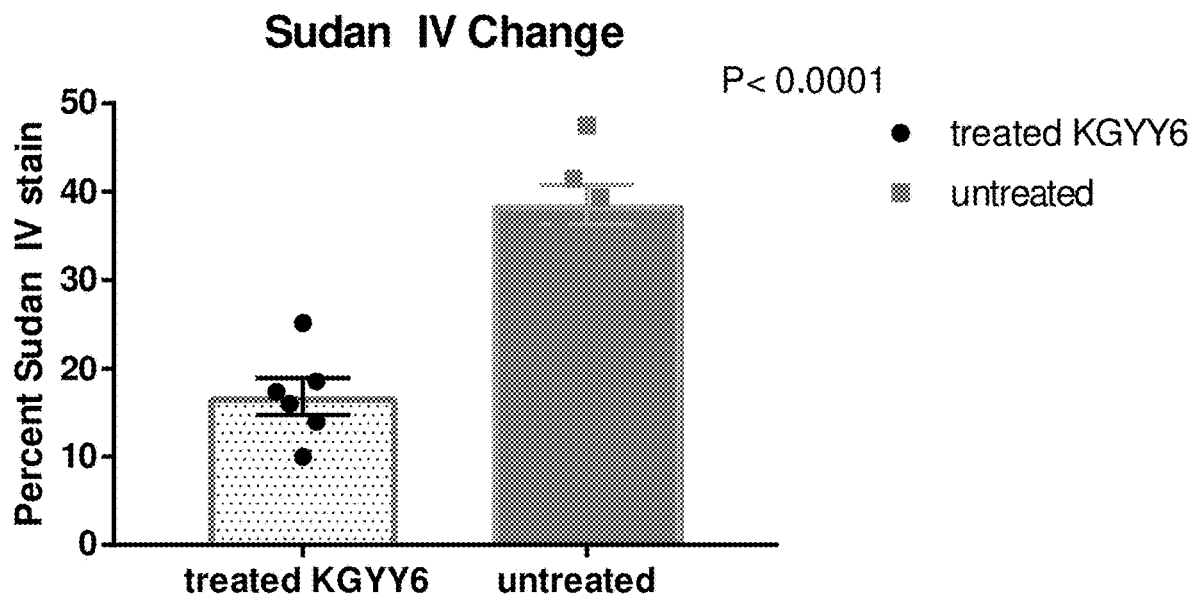
FIG. 29 is a graph demonstrating the reduction of lesion areas of Sudan IV staining.

This example demonstrates atherosclerotic changes that ApoE-/- mice experienced when treated with $KGYY_6$ (6-mer-SEQ ID NO: 29). ApoE-/- mice were fed a high fat diet for 16 weeks. Mice were randomly assigned to receive dose of 1 mg/kg of $KGYY_6$ (6-mer-SEQ ID NO:29) by IV tail injection, once a week for a period of 4 weeks. Control mice received vehicle only. Atherosclerosis was investigated by several methods. En-face analysis utilizing Sudan IV stain (lipid stain) demonstrated a significant reduction in lesion areas. FIG. 28A is an image of KGYY6 treated aortic en-face Sudan IV staining and FIG. 28B is an image of control (untreated) aortic en-face Sudan staining. FIG. 29 is a graph demonstrating the reduction of lesion areas of Sudan IV staining.

Figure 30:
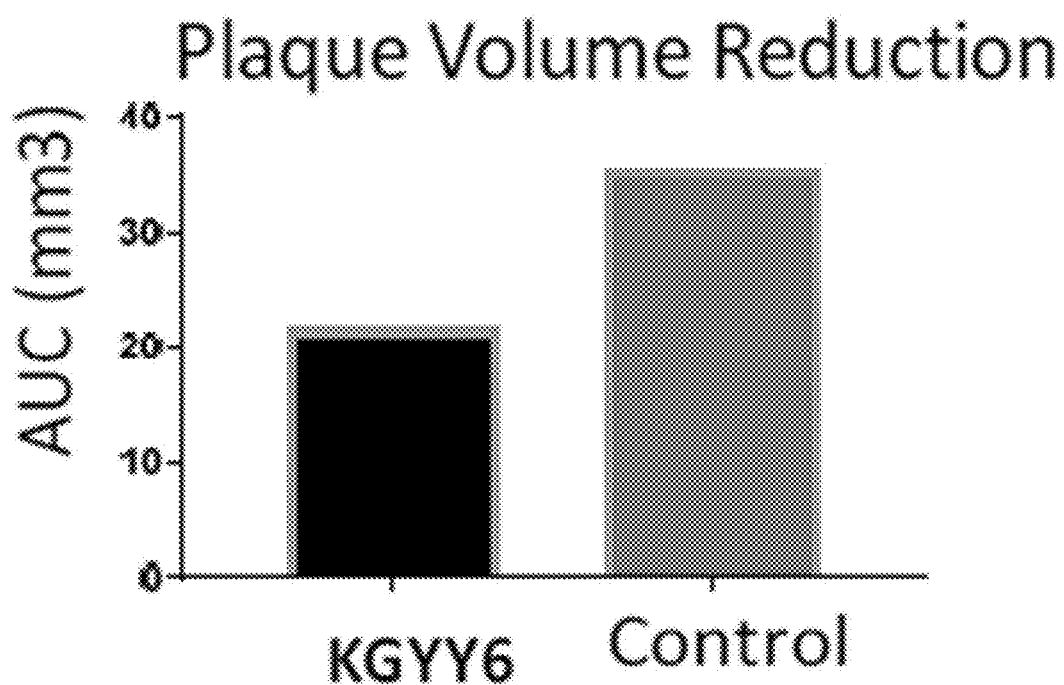
FIG. 30 is a graph of plaque volume reduction for area under the curve.

Further, measurement of plaque area and morphology was performed using the Paigen method. This method obtains sequential 5 μm aortic cross sections from the aortic root beginning at the valve leaflets into the ascending aorta. At 50 μm intervals, slides are stained after which the area of atherosclerotic lesion is measured. Individual plaque area measurements are plotted against the micrometer intervals and a curve is established, with the area under the curve (AUC) giving the total volume of plaque. These results are presented in graph format in FIG. 30, which demonstrates that mice treated with $KGYY_6$ (SEQ ID NO: 29) showed reduction in plaque volume under the curve. Moreover, characterization of plaque composition or aortic samples was performed using trichrome staining techniques and these results are presented in graph format in FIG. 31. Indeed, this FIG. 31 data, which was generated using Image Pro Plus software analysis, quantifies and shows that plaque compositional changes occurred, including increased collagen and reduced smooth muscle content.

FIG. 32A is an image of trichrome stained cells of the cross-sections of the aorta of the $KGYY_6$ treated subject. FIG. 32B is an image of trichrome stained cells of the cross-sections of the control subjects. In FIG. 32A, 50 identifies areas characteristic of plaque formation. 60 identifies aortic valve leaflets. FIG. 32B, the control (untreated)

50 areas characteristic of plaque (area under the curve) are greater than those in the subjects treated with the KGYY$_6$ peptide.

Example 15

This example demonstrates that KGYY$_6$ (6-mer-SEQ ID NO:29) results in significant improvement in glucose tolerance and insulin sensitivity.

Figure 33:
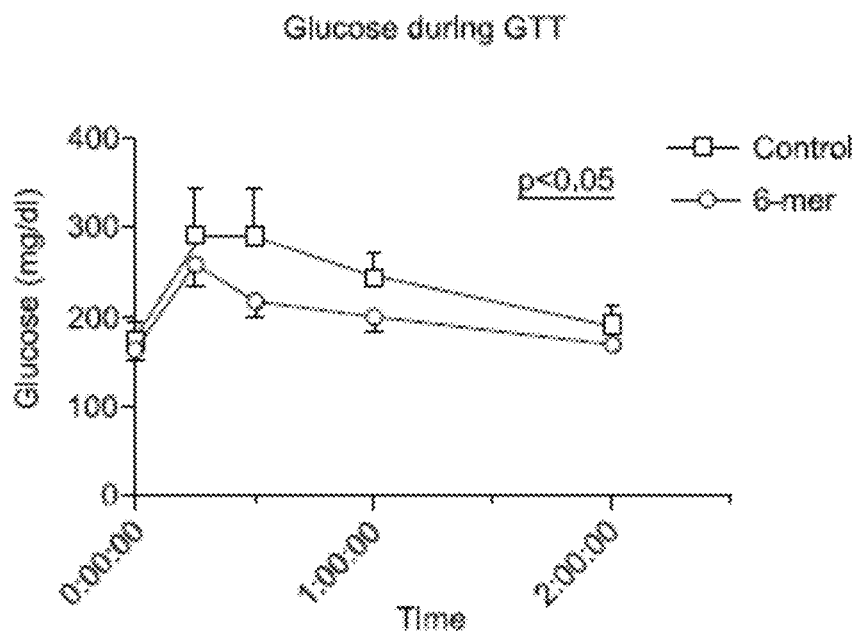
FIG. 33(a)-(b) are graphs that show a statistically significant improvement in glucose tolerance (GTT) and insulin sensitivity in response to SEQ ID NO: 29.
Figure 33:
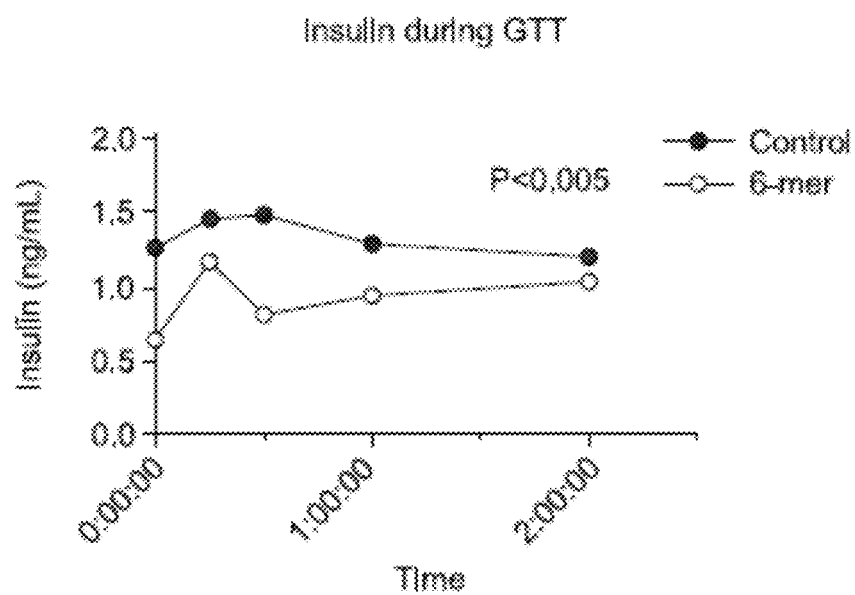

ApoE−/− mice were fed a 60% high fat diet (research diet) for 1 week. A select population of mice were then injected with 6-mer peptide at a dose of 1 mg/kg and others were untreated and tracked as controls. Glucose tolerance testing (GTT) was performed by fasting 6 hours, followed by intraperitoneal injection of 1 g/kg body weight glucose in water. Both blood glucose and blood serum insulin were measured at 0, 15 minutes, 30 minutes, 60 minutes, and 2 hours. The results of this study are shown in FIGS. 33(a) and 33(b). Peptide treated ApoE deficient mice demonstrated significantly increased glucose tolerance as well as significantly improved insulin sensitivity and lowered plasma insulin levels compared to control.

Figure 34:
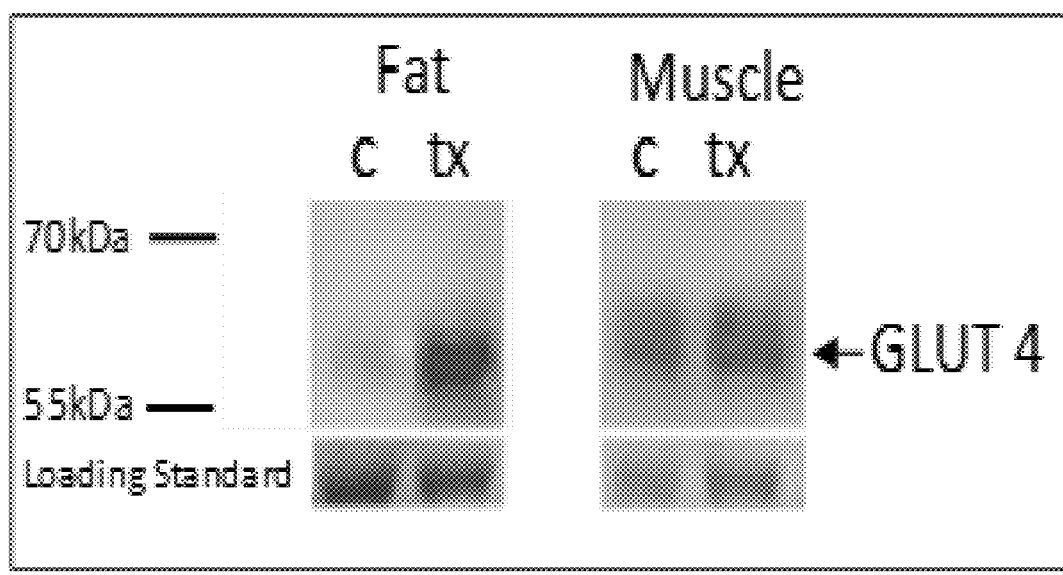
FIG. 34 is a western blot analysis of GLUT4 (insulin regulated glucose transport protein) comparing adipose and muscle tissue of treated (with SEQ ID NO: 29) and untreated mice.

Western analysis was performed on adipose and muscle tissue of the treated and untreated mice, demonstrating an increase in expression of the glucose transport protein (GLUT4) in white adipose tissue, as shown in FIG. 34. Moreover, the western analysis also demonstrated that the muscle tissue showed increased expression of the GLUT4 protein. GLUT4 is responsible for glucose uptake in response to insulin and known to have reduced expression in type 2 diabetes.

This study demonstrates that administration of the peptide affects glucose tolerance, insulin sensitivity, and GLUT4 levels, each of which may be important to treating type 2 diabetic subjects.

Example 16

This example demonstrates administration of the KGYY$_6$ (6-mer-SEQ ID NO:29) affects the inflammatory cytokine production of IL2, INFγ, and IL17a.

Figure 35:
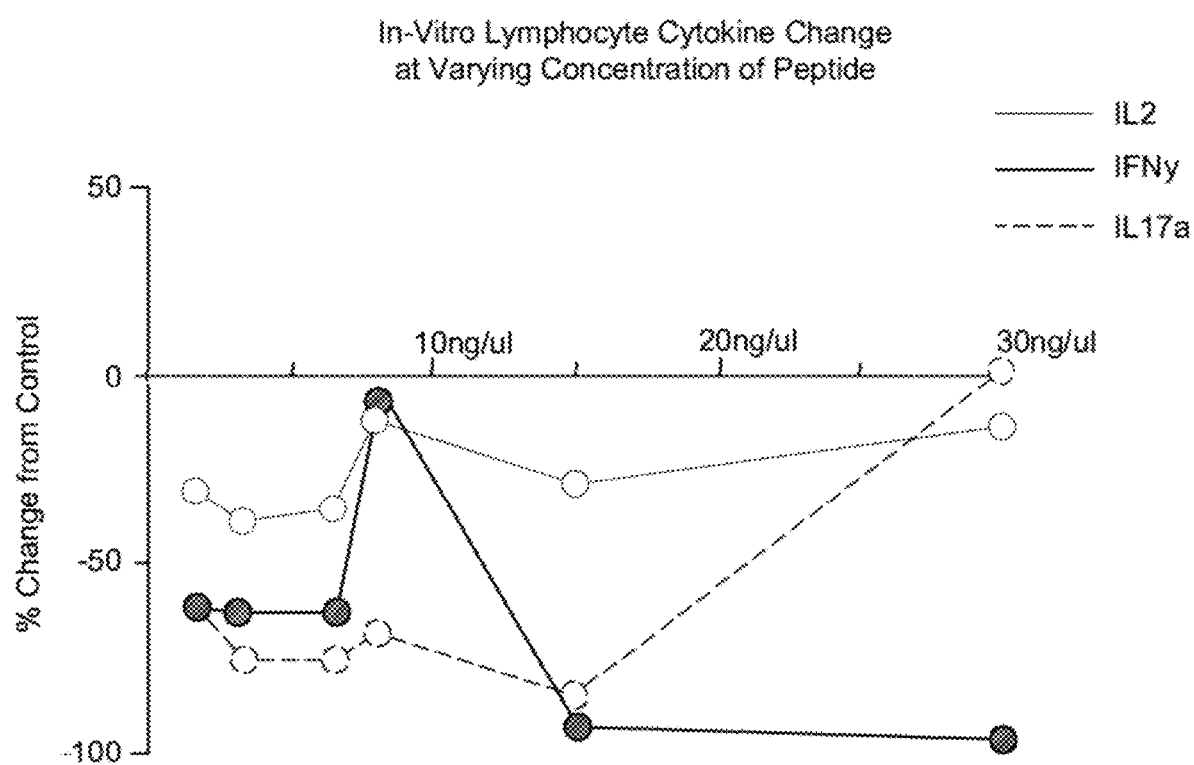
FIG. 35 is a graph of the percentage change of in-vitro lymphocyte cytokines measured in spleen cells from ApoE−/− and C57BL/6 mice as measured by flow cytometry.

Spleens from ApoE mice and C57BL/6 mice were processed for lymphocytes. ApoE−/− and C57BL/6 mice were fed a 60% high fat diet (research diet) for 1 week. Splenic lymphocytes were treated with 6-mer in vitro for 24 hours. Cells were placed in media overnight in the presence of varying concentrations of 6-mer peptides. The following morning. Brefeldin A was administered for 4 hours. All cells were stained for CD3, CD4, CD40 (Th40 cells) and measured by use of flow cytometry for their production of IL2, INFγ, and IL17a. The results of this study are shown in FIG. 35.

From the foregoing, it is readily apparent that new and useful implementations of the methods have been herein described and illustrated which fulfill numerous desiderata in remarkably unexpected fashions. It is, of course, understood that such modifications, alterations and adaptations as may readily occur to the artisan confronted with this disclosure are intended within the spirit of this disclosure, which is limited only by the scope of the claims appended hereto.

What is claimed:

1. A method for treating type 2 diabetes in a subject, the method comprising administering to the subject a therapeutically effective amount of a peptide of 6 amino acids in length and having an amino acid sequence of SEQ ID NO: 28 or 29.

2. The method of claim 1, wherein the peptide binds to a CD40 protein in the subject.

3. The method of claim 2, wherein the peptide binds to the CD40 protein with a Kd of no more than $1 \times 10^{-6}$ M.

4. The method of claim 1, wherein the peptide inhibits the binding of CD40 to CD154 in the subject.

5. The method of claim 1, wherein the peptide binds to multiple bone marrow derived cell types that express CD40 of approximately 45 kDa.

6. The method of claim 5, wherein the bone marrow derived cell types that express CD40 of approximately 45 kDa comprise splenic CD4$^+$ cells, CD8$^+$ cells, and antigen presenting cells.

7. The method of claim 1, wherein the peptide has an amino acid sequence of SEQ ID NO: 28.

8. The method of claim 1, wherein the peptide has an amino acid sequence of SEQ ID NO: 29.

9. The method of claim 1, wherein the subject is human.

10. The method of claim 1, wherein the method treats glucose intolerance and/or insulin insensitivity in the subject.

11. The method of claim 1, wherein administration of the peptide increases glucose transport protein 4 (GLUT 4) in the subject.

12. The method of claim 1, wherein administration of the peptide reduces expression of IL-2 in the subject.

13. The method of claim 1, wherein administration of the peptide reduces expression of IFNγ in the subject.

14. The method of claim 1, wherein the peptide is administered in an amount sufficient to reduce or inhibit interleukin-2 signaling in the subject.

15. The method of claim 1, wherein the peptide is administered in an amount sufficient to reduce or inhibit interleukin 17 (IL-17) signaling.

16. The method of claim 1, wherein administration of the peptide reduces expression of IL-17A in the subject.

17. A method of increasing glucose tolerance in a subject in need thereof, the method comprising administering to the subject a therapeutically effective amount of a peptide of 6 amino acids in length and having an amino acid sequence of SEQ ID NO: 28 or 29.

18. A method of increasing insulin sensitivity in a subject in need thereof, the method comprising administering to the subject a therapeutically effective amount of a peptide of 6 amino acids in length and having an amino acid sequence of SEQ ID NO: 28 or 29.

19. A method of decreasing plasma insulin levels in a subject in need thereof, the method comprising administering to the subject a therapeutically effective amount of a peptide of 6 amino acids in length and having an amino acid sequence of SEQ ID NO: 28 or 29.

20. A method of increasing expression of GLUT4 in a subject in need thereof, the method comprising administering to the subject a therapeutically effective amount of a peptide of 6 amino acids in length and having an amino acid sequence of SEQ ID NO: 28 or 29.

* * * * *